US010045947B2

(12) United States Patent
Bencherif et al.

(10) Patent No.: US 10,045,947 B2
(45) Date of Patent: *Aug. 14, 2018

(54) INJECTABLE PREFORMED MACROSCOPIC 3-DIMENSIONAL SCAFFOLDS FOR MINIMALLY INVASIVE ADMINISTRATION

(75) Inventors: Sidi A. Bencherif, Dorchester, MA (US); David J. Mooney, Sudbury, MA (US); David Edwards, Boston, MA (US); Roger Warren Sands, Chicago, IL (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/112,096

(22) PCT Filed: Apr. 27, 2012

(86) PCT No.: PCT/US2012/035505
§ 371 (c)(1),
(2), (4) Date: Dec. 27, 2013

(87) PCT Pub. No.: WO2012/149358
PCT Pub. Date: Nov. 1, 2012

(65) Prior Publication Data
US 2014/0112990 A1  Apr. 24, 2014

Related U.S. Application Data

(60) Provisional application No. 61/480,237, filed on Apr. 28, 2011.

(51) Int. Cl.
*A61K 9/70* (2006.01)
*A61K 39/00* (2006.01)
*A61L 27/20* (2006.01)
*A61L 27/50* (2006.01)
*A61L 27/52* (2006.01)
*A61L 27/54* (2006.01)
*A61L 27/56* (2006.01)

(52) U.S. Cl.
CPC ........ *A61K 9/7007* (2013.01); *A61K 39/0011* (2013.01); *A61L 27/20* (2013.01); *A61L 27/50* (2013.01); *A61L 27/52* (2013.01); *A61L 27/54* (2013.01); *A61L 27/56* (2013.01); *A61K 2039/55522* (2013.01); *A61K 2039/55561* (2013.01); *A61K 2039/64* (2013.01); *A61L 2300/252* (2013.01); *A61L 2300/258* (2013.01); *A61L 2300/64* (2013.01); *A61L 2400/06* (2013.01); *A61L 2400/16* (2013.01); *A61L 2430/34* (2013.01)

(58) Field of Classification Search
CPC ............... A61L 27/20; A61L 2300/252; A61L 2300/258; A61L 2300/64; A61L 2400/06; A61L 2400/16; A61L 27/50; A61L 27/52; A61L 27/54; A61L 27/56; C08L 5/04; A61K 2039/55522; A61K 2039/55561
See application file for complete search history.

(56) References Cited

U.S. PATENT DOCUMENTS

| | | | |
|---|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,403,374 B1 | 6/2002 | Tsien et al. |
| 6,429,199 B1 | 8/2002 | Krieg et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 6,858,222 B2 | 2/2005 | Nelson |
| 7,015,205 B1 | 3/2006 | Wallack et al. |

(Continued)

FOREIGN PATENT DOCUMENTS

| CN | 1757662 A | 4/2006 |
|---|---|---|
| CN | 101655611 A | 2/2010 |

(Continued)

OTHER PUBLICATIONS

Kathuria et al ("Synthesis and characterization of elastic and macroporous chitosan—gelatin cryogels for tissue engineering," Acta Biomaterialia 5 (2009) 406-418, Available online Jul. 25, 2008).*

(Continued)

*Primary Examiner* — Devang K Thakor

(74) *Attorney, Agent, or Firm* — McCarter & English, LLP; Marin Laccotripe Zacharakis; Briana M. Erickson

(57) ABSTRACT

The invention provides polymer compositions for cell and drug delivery.

39 Claims, 13 Drawing Sheets

(56) References Cited

U.S. PATENT DOCUMENTS

| | | | |
|---|---|---|---|
| 7,157,566 B2 | 1/2007 | Tsien et al. | |
| 7,186,413 B2 | 3/2007 | Bouhadir et al. | |
| 7,192,693 B2 | 3/2007 | Bryant et al. | |
| 7,427,602 B1 | 9/2008 | Shea et al. | |
| 7,575,759 B2 | 8/2009 | Murphy et al. | |
| 7,687,241 B2 | 3/2010 | Chen | |
| 7,790,699 B2 | 9/2010 | Melvik et al. | |
| 8,067,237 B2 | 11/2011 | Mooney et al. | |
| 8,188,058 B2 | 5/2012 | Hackam et al. | |
| 8,273,373 B2 * | 9/2012 | Alsberg et al. | 424/484 |
| 8,354,119 B2 | 1/2013 | Geistlich et al. | |
| 8,709,464 B2 | 4/2014 | Ma et al. | |
| 8,728,456 B2 | 5/2014 | Sands et al. | |
| 9,012,399 B2 | 4/2015 | Cao et al. | |
| 9,132,210 B2 | 9/2015 | Mooney et al. | |
| 9,370,558 B2 | 6/2016 | Ali et al. | |
| 2002/0131853 A1 | 9/2002 | Nagasawa | |
| 2002/0150604 A1 | 10/2002 | Yi et al. | |
| 2003/0075822 A1 | 4/2003 | Slivka et al. | |
| 2003/0082806 A1 | 5/2003 | Berenson et al. | |
| 2003/0095994 A1 | 5/2003 | Geistlich et al. | |
| 2003/0100527 A1 | 5/2003 | Krieg et al. | |
| 2003/0194397 A1 | 10/2003 | Mishra | |
| 2003/0232895 A1 | 12/2003 | Omidian et al. | |
| 2004/0058883 A1 | 3/2004 | Phillips et al. | |
| 2004/0063206 A1 | 4/2004 | Rowley et al. | |
| 2004/0136968 A1 | 7/2004 | Zheng et al. | |
| 2004/0151764 A1 | 8/2004 | Zamora | |
| 2004/0220111 A1 | 11/2004 | Kleinman et al. | |
| 2004/0242469 A1 | 12/2004 | Lee et al. | |
| 2004/0242482 A1 | 12/2004 | Gehring et al. | |
| 2005/0002915 A1 | 1/2005 | Atala et al. | |
| 2005/0037330 A1 | 2/2005 | Fischer et al. | |
| 2005/0053667 A1 | 3/2005 | Irvine et al. | |
| 2005/0079159 A1 | 4/2005 | Shastri et al. | |
| 2005/0106211 A1 | 5/2005 | Nelson et al. | |
| 2005/0154376 A1 | 7/2005 | Riviere et al. | |
| 2005/0177249 A1 | 8/2005 | Kladakis et al. | |
| 2005/0202394 A1 | 9/2005 | Dobson | |
| 2006/0083712 A1 | 4/2006 | Anversa | |
| 2006/0141018 A1 | 6/2006 | Cochrum et al. | |
| 2006/0264380 A1 | 11/2006 | Hellstrom et al. | |
| 2006/0292134 A1 | 12/2006 | Stohs | |
| 2007/0003595 A1 | 1/2007 | Wang et al. | |
| 2007/0020232 A1 | 1/2007 | Rossignol et al. | |
| 2007/0026518 A1 | 2/2007 | Healy et al. | |
| 2007/0081972 A1 | 4/2007 | Sandler et al. | |
| 2007/0116680 A1 | 5/2007 | Stegemann et al. | |
| 2007/0178159 A1 | 8/2007 | Chen et al. | |
| 2007/0190646 A1 | 8/2007 | Engler et al. | |
| 2008/0044900 A1 | 2/2008 | Mooney et al. | |
| 2008/0044990 A1 | 2/2008 | Lee | |
| 2008/0051490 A1 | 2/2008 | Williams et al. | |
| 2008/0138416 A1 | 6/2008 | Rauh et al. | |
| 2008/0152624 A1 | 6/2008 | Paludan et al. | |
| 2008/0206308 A1 | 8/2008 | Jabbari et al. | |
| 2008/0268052 A1 | 10/2008 | Voytik-Harbin et al. | |
| 2009/0017096 A1 | 1/2009 | Lowman et al. | |
| 2009/0192079 A1 | 7/2009 | Santos et al. | |
| 2009/0238853 A1 | 9/2009 | Liu et al. | |
| 2009/0297579 A1 | 12/2009 | Semino et al. | |
| 2009/0305983 A1 | 12/2009 | Ying et al. | |
| 2010/0015709 A1 | 1/2010 | Rehfeldt et al. | |
| 2010/0055186 A1 | 3/2010 | Dadsetan et al. | |
| 2010/0080816 A1 | 4/2010 | Hadeiba et al. | |
| 2010/0129422 A1 | 5/2010 | Han et al. | |
| 2010/0189760 A1 | 7/2010 | Schaffer et al. | |
| 2010/0190741 A1 | 7/2010 | Cohen et al. | |
| 2010/0272771 A1 | 10/2010 | Harlow et al. | |
| 2011/0008443 A1 | 1/2011 | Alsberg et al. | |
| 2011/0020216 A1 | 1/2011 | Mooney et al. | |
| 2011/0117170 A1 | 5/2011 | Cao et al. | |
| 2011/0223255 A1 | 9/2011 | Thiesen et al. | |
| 2011/0300186 A1 | 12/2011 | Hellstrom et al. | |
| 2012/0100182 A1 | 4/2012 | Mooney et al. | |
| 2012/0121539 A1 | 5/2012 | Sands et al. | |
| 2012/0122218 A1 | 5/2012 | Huebsch et al. | |
| 2012/0134967 A1 | 5/2012 | Mooney et al. | |
| 2012/0256336 A1 | 10/2012 | Yano et al. | |
| 2012/0264599 A1 | 10/2012 | Komatsu et al. | |
| 2012/0329791 A1 | 12/2012 | Ashwell et al. | |
| 2013/0029030 A1 | 1/2013 | Larsen | |
| 2013/0177536 A1 | 7/2013 | Mooney et al. | |
| 2013/0202707 A1 | 8/2013 | Ali et al. | |
| 2013/0302396 A1 | 11/2013 | Mooney et al. | |
| 2013/0331343 A1 | 12/2013 | Cao et al. | |
| 2014/0079752 A1 | 3/2014 | Huebsch et al. | |
| 2014/0178964 A1 | 6/2014 | Mooney et al. | |
| 2014/0193488 A1 | 7/2014 | Kim et al. | |
| 2014/0227327 A1 | 8/2014 | Bencherif et al. | |
| 2014/0234423 A1 | 8/2014 | Sands et al. | |
| 2015/0024026 A1 | 1/2015 | Mooney et al. | |
| 2015/0072009 A1 | 3/2015 | Kim et al. | |
| 2015/0366956 A1 | 12/2015 | Mooney et al. | |
| 2016/0220667 A1 | 8/2016 | Mooney et al. | |
| 2016/0220668 A1 | 8/2016 | Mooney et al. | |
| 2016/0228543 A1 | 8/2016 | Mooney et al. | |
| 2016/0271298 A1 | 9/2016 | Mooney et al. | |
| 2016/0279219 A1 | 9/2016 | Mooney et al. | |
| 2016/0279220 A1 | 9/2016 | Mooney et al. | |
| 2016/0296611 A1 | 10/2016 | Ali et al. | |
| 2017/0042995 A1 | 2/2017 | Ali et al. | |
| 2017/0182138 A1 | 6/2017 | Kim et al. | |

FOREIGN PATENT DOCUMENTS

| | | |
|---|---|---|
| EP | 0562862 A1 | 9/1993 |
| EP | 1452191 A2 | 9/2004 |
| EP | 1561481 A2 | 8/2005 |
| EP | 1975230 A1 | 1/2008 |
| JP | 2000503884 A | 4/2000 |
| JP | 2001524136 A | 11/2001 |
| JP | 2003506401 A | 2/2003 |
| JP | 2003180815 A | 7/2003 |
| JP | 2004520043 A | 7/2004 |
| JP | 2005160669 A | 6/2005 |
| JP | 2005528401 A | 9/2005 |
| JP | 2007500673 A | 1/2007 |
| JP | 2007503881 A | 3/2007 |
| JP | 2007528848 A | 10/2007 |
| JP | 2008515503 A | 5/2008 |
| JP | 2008528114 A | 7/2008 |
| JP | 2009519042 A | 5/2009 |
| JP | 2009521406 A | 6/2009 |
| JP | 2009540921 A | 11/2009 |
| JP | 2010502824 A | 1/2010 |
| JP | 2010508976 A | 3/2010 |
| JP | 2011511684 A | 4/2011 |
| WO | WO-9616086 A1 | 5/1996 |
| WO | WO-98012228 A1 | 3/1998 |
| WO | WO-9816266 A1 | 4/1998 |
| WO | WO-9951259 A2 | 10/1999 |
| WO | WO-9951259 A3 | 1/2000 |
| WO | WO-0050006 A2 | 8/2000 |
| WO | WO-2001010421 A1 | 2/2001 |
| WO | WO-0135932 A2 | 5/2001 |
| WO | WO-0216557 | 2/2002 |
| WO | WO-0240071 A1 | 5/2002 |
| WO | WO-02058723 A2 | 8/2002 |
| WO | WO-03020884 A2 | 3/2003 |
| WO | WO-04006990 A2 | 1/2004 |
| WO | WO-04030706 A2 | 4/2004 |
| WO | WO-2004029230 A2 | 4/2004 |
| WO | WO-2004031371 A2 | 4/2004 |
| WO | WO-04089413 A1 | 10/2004 |
| WO | WO-05013896 A2 | 2/2005 |
| WO | WO-05013933 A1 | 2/2005 |
| WO | WO-05026318 A2 | 3/2005 |
| WO | WO-2005020849 A2 | 3/2005 |
| WO | WO-05037190 A2 | 4/2005 |
| WO | WO-05037293 A1 | 4/2005 |
| WO | WO-05046748 | 5/2005 |
| WO | WO-05072088 A2 | 8/2005 |
| WO | WO-2006040128 A1 | 4/2006 |

(56) References Cited

FOREIGN PATENT DOCUMENTS

| WO | WO-2006078987 A2 | 7/2006 |
|---|---|---|
| WO | WO-2006113407 A2 | 10/2006 |
| WO | WO-06119619 A1 | 11/2006 |
| WO | WO-06136905 A2 | 12/2006 |
| WO | WO-07030901 A1 | 3/2007 |
| WO | WO-07063075 A1 | 6/2007 |
| WO | WO-07064152 A1 | 6/2007 |
| WO | WO-07070660 A2 | 6/2007 |
| WO | WO-2007070660 A2 | 6/2007 |
| WO | WO-07078196 A1 | 7/2007 |
| WO | WO-07107739 | 9/2007 |
| WO | WO-07150020 A1 | 12/2007 |
| WO | WO-2007149161 A2 | 12/2007 |
| WO | WO-08018707 A1 | 2/2008 |
| WO | WO-2008031525 A1 | 3/2008 |
| WO | WO 2008057600 A2 | 5/2008 |
| WO | WO-08109852 A2 | 9/2008 |
| WO | WO-08114149 A2 | 9/2008 |
| WO | WO-08148761 A1 | 12/2008 |
| WO | WO-08157394 A2 | 12/2008 |
| WO | WO-09002401 A2 | 12/2008 |
| WO | WO-09005769 A2 | 1/2009 |
| WO | WO-09018500 A1 | 2/2009 |
| WO | WO-09072767 A2 | 6/2009 |
| WO | WO-09074341 A1 | 6/2009 |
| WO | WO-09102465 A2 | 8/2009 |
| WO | WO-09146456 A1 | 12/2009 |
| WO | WO-09155583 A1 | 12/2009 |
| WO | WO-2010/78209 A2 | 7/2010 |
| WO | WO-10120749 A2 | 10/2010 |
| WO | WO-11014871 A1 | 2/2011 |
| WO | WO-11063336 A2 | 5/2011 |
| WO | WO-11109834 A2 | 9/2011 |
| WO | WO-11130753 A2 | 10/2011 |
| WO | WO-11150240 A1 | 12/2011 |
| WO | WO-11151431 A1 | 12/2011 |
| WO | WO-11163669 A2 | 12/2011 |
| WO | WO-12009611 A2 | 1/2012 |
| WO | WO-12019049 | 2/2012 |
| WO | WO-12048165 A2 | 4/2012 |
| WO | WO-12064697 A2 | 5/2012 |
| WO | WO-12148684 A1 | 11/2012 |
| WO | WO-2012149358 A1 | 11/2012 |
| WO | WO-12167230 A1 | 12/2012 |
| WO | WO-13106852 A1 | 7/2013 |
| WO | WO-13158673 A1 | 10/2013 |
| WO | WO-2015168379 A2 | 11/2015 |
| WO | WO-2016123573 A1 | 8/2016 |
| WO | WO 2016161372 A1 | 10/2016 |

OTHER PUBLICATIONS

Buonaguro et al ("Translating Tumor Antigens into Cancer Vaccines," Clinical and Vaccine Immunology, Jan. 2011. p. 23-34) [Buonaguro].*
Thornton et al ("Shape Retaining Injectable Hydrogels for Minimally Invasive Bulking," The Journal of Urology, vol. 172, 763-768, Aug. 2004).*
"Antigens and Receptors." *Immunology*. Doan et al., eds. Philadelphia: Wolters Kluwer/Lippincott Williams & Wilsons. (2008):11-23.
"Transient." Merriam-Webster Dictionary. Web. Jul. 18, 2014. www.merriam-webster.com/dictionary/transient.
"Wound Management: Past, Present, and Future." *Clinicians' Pocket Guide to Chronic Wound Repair*. Mulder et al., eds. Springhouse, PA: Springhouse Corporation. (1998):85-90.
Abrahams et al. "Expression and Secretion of Antiviral Factors by Trophoblast Cells Following Stimulation by the TLF-3 Agonist, Poly (I:C)." *Hum. Reprod*. 21.9(2006):2432-2439.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol*. 171.10(2003):4984-4989.
Akira et al. "Pathogen Recognition and Innate Immunity." *Cell*. 124.4(2006):783-801.
Akira et al. "Toll-Like Receptors: Critical Proteins Linking Innate and Acquired Immunity." *Nat. Immunol*. 2.8(2001):675-680.
Aldhous. "Print Me a Heart and a Set of Arteries." *New Scientist*. 2547(2006):19.
Ali et al. "Controlled Local Delivery of GM-CSF From Polymer-Based Vaccines Enhances Anti-Tumor Immune Responses by Priming Host Dendritic Cells." 2007 *AACR Annual Meeting*. 48(2007):652. (Abstract #2736).
Ali et al. "Converging Cell Therapy with Biomaterials." *Cell Transplantation from Laboratory to Clinic*. Burlington, MA: Elsevier, Inc. (2006):591-609.
Ali et al. "In situ Regulation of DC Subsets and T Cells Mediates Tumor Regression in Mice." *Sci. Transl. Med*. 1.8(2009):8-19.
Ali et al. "Infection-Mimicking Materials to Program Dendritic Cells in situ." *Nat. Mater*. 8.2(2009):151-158.
Ali et al. "Sustained GM-CSF and PEI Condensed pDNA Presentation Increases the Level and Duration of Gene Expression in Dendritic Cells." *J. Control. Release*. 132.3(2008):273-278.
Allen et al. "Regulation of Satellite Cells During Skeletal Muscle Growth and Development." *Proc. Soc. Exp. Biol. Med*. 194.2(1990):81-86.
Allen et al. "Regulation of Skeletal Muscle Satellite Cell Proliferation by Bovine Pituitary Fibroblast Growth Factor." *Exp. Cell Res*. 152.1(1984):154-160.
Almarza et al. "Evaluation of Three Growth Factors in Combination of Two for Temporomandibular Joint Disc Tissue Engineering." *Arch. Oral Biol*. 51.3(2006):215-221.
Alsberg et al. "Cell-Interactive Alginate Hydrogels for Bone Tissue Engineering." *J. Dent. Res*. 80.11(2001):2025-2029.
Alsberg et al. "Engineering Growing Tissues." *PNAS*. 99.18(2002):12025-12030.
Alsberg et al. "Regulating Bone Formation via Controlled Scaffold Design." *J. Dent. Res*. 82.11(2003):903-908.
Anderson et al. "Biomaterial Microarrays: Rapid, Microscale Screening of Polymer-Cell Interaction." *Biomaterials*. 26.23(2005):4892-4897.
Anderson et al. "Nanoliter-Scale Synthesis of Arrayed Biomaterials and Application to Human Embryonic Stem Cells." *Nat. Biotechnol*. 22.7(2004):863-866.
Anderson et al. "The NOD Mouse: A Model of Immune Dysregulation." *Annu. Rev. Immunol*. 23(2005):447-485.
Anderson. "A Role for Nitric Oxide in Muscle Repair: Nitric Oxide-Mediated Activation of Muscle Satellite Cells." *Mol. Biol. Cell*. 11(2000):1859-1874.
Arany et al. "At the Edge of Translation—Materials to Program Cells for Directed Differentiation." *Oral Dis*. 17.3(2011):241-251.
Atala et al. "Endoscopic Treatment of Vesicoureteral Reflux with a Chondrocyte-Alginate Suspension." *J. Urol*. 152(1994):641-643.
Augst et al. "Alginate Hydrogels as Biomaterials." *Macromol. Biosci*. 6(2006):623-633.
Bachelder et al. "Acid-Degradable Polyurethane Particles for Protein-Based Vaccines: Biological Evaluation and in Vitro Analysis of Particle Degradation Products." *Mol. Pharm*. 5.5(2008):876-884.
Bachem et al. "Superior Antigen Cross-Presentation and XCR1 Expression Define Human CD11c+CD141+ Cells as Homologues of Mouse CD8+ Dendritic Cells." *J. Exp. Med*. 207.6(2010):1273-1281.
Badovinac et al. "Regulation of CD8 T+ Cells Undergoing Primary and Secondary Responses to Infection in the Same Host." *J. Immunol*. 170(2003):4933-4942.
Bakri et al. "Pharmacokinetics of Intravitreal Bevacizumab (Avastin)." *Ophthalmology*. 114.5(2007):855-859.
Balakrishna et al. "Structural Correlates of Antibacterial and Membrane-Permeabilizing Activities in Acylpolyamines." *Antimicrob. Agents Chemother*. 50.3(2006):852-861.
Banchereau et al. "Dendritic Cells and the Control of Immunity." *Nature*. 392.6673(1998):245-252.
Bar-Cohen et al. "Electroactive Polymer Actuators and Sensors." *MRS Bullet*. 33.3(2008):173-181.

(56) References Cited

OTHER PUBLICATIONS

Bar-Or et al. "Induction of Antigen-Specific Tolerance in Multiple Sclerosis after Immunization with DNA Encoding Myelin Basic Protein in a Randomized, Placebo-Controlled Phase 1/2 Trial." *Arch. Neurol.* 64.10(2007):1407-1415.
Barbero et al. "Growth Factor Supplemented Matrigel Improves Ectopic Skeletal Muscle Formation—A Cell Therapy Approach." *J. Cell. Physiol.* 186(2001):183-192.
Barrio et al. "A Two-Dimensional Numerical Study of Spatial Pattern Formation in Interacting Turing Systems." *Bull. Math. Biol.* 61.3(1999):483-505.
Bates. "Improved Muscle Regeneration by Combining VEGF With IGF1." *Regen. Med.* 5.6(2010):853-854.
Beaucage et al. "The Functionalization of Oligonucleotides Via Phosphoramidite Derivatives." *Tetrahedron.* 49.10(1993):1925-1963.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.
Beebe et al. "Functional Hydrogel Structures for Autonomous Flow Control Inside Microfluidic Channels." *Nature.* 404(2000):588-590.
Bekiari et al. "Study of Poly(N,N-dimethylacrylamide)/CdS Nanocomposite Organic/Inorganic Gels." *Langmuir.* 20.19(2004):7972-7975.
Bischoff. "Proliferation of Muscle Satellite Cells on Intact Myofibers in Culture." *Dev. Biol.* 115.1(1986):129-139.
Blanas et al. "Induction of Autoimmune Diabetes by Oral Administration of Autoantigen." *Science.* 274.5293(1996):1707-1709.
Blumenthal et al. "Polyurethane Scaffolds Seeded with Genetically Engineered Skeletal Myoblasts: A Promising Tool to Regenerate Myocardial Function." *Artificial Organs.* 34.2(2010):E46-E54.
Bohl et al. "Role of Synthetic Extracellular Matrix in Development of Engineered Dental Pulp." *J. Biomater. Sci. Polym. Ed.* 9.7(1998):749-764.
Bonauer et al. "MicroRNA-92a Controls Angiogenesis and Functional Recovery of Ischemic Tissues in Mice." *Science.* 324.5935(2009):1710-1713.
Boontheekul et al. "Controlling Alginate Gel Degradation Utilizing Partial Oxidation and Bimodal Molecular Weight Distribution." *Biomaterials.* 26.15(2005):2455-2465.
Boontheekul et al. "Regulating Myoblast Phenotype Through Controlled Gel Stiffness and Degradation." *Tissue Engin.* 13.7(2007):1431-1442.
Borselli et al. "Functional Muscle Regeneration with Combined Delivery of Angiogenesis and Myogenesis Factors." *PNAS.* 107.8(2010):3287-3292.
Bouhadir et al. "Degradation of Partially Oxidized Alginate and its Potential Application for Tissue Engineering." *Biotechnol. Prog.* 17.5(2001):945-950.
Bouhadir et al. "Synthesis of Cross-Linked Poly(aldehyde guluronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brinkmann et al. "Neutrophil Extracellular Traps Kill Bacteria." *Science.* 303.5663(2004):1532-1535.
Brouwers et al. "Can the Growth Factors PTHrP, Ihh and VEGF, Together Regulate the Development of a Long Bone?" *J. Biomech.* 39.15(2006):2774-2782.
Bryant et al. "Photo-Patterning of Porous Hydrogels for Tissue Engineering." *Biomater.* 28.19(2007):2978-2986.
Burdick et al. "Stimulation of Neurite Outgrowth by Neurotrophins Delivered From Degradable Hydrogels." *Biomater.* 27.3(2006):452-459.

Calvert. "Electroactive Polymer Gels." *Electroactive Polymer (EAP) Acutators as Artificial Muscle: Reality, Potential, and Challenges.* Bar-Cohen, ed. Bellingham, WA: Spie Press. (2004):151-170.
Calvert. "Gel Sensors and Actuators." *MRS Bullet.* 33.3(2008):207-212.
Cao et al. "Promoting Angiogenesis via Manipulation of VEGF Responsiveness with Notch Signaling." *Biomater.* 30.25(2009):4085-4093.
Carlson et al. "Notch Signaling Pathway and Tissue Engineering." *Front. Biosci.* 12(2007):5143-5156.
Carmeliet et al. "Angiogenesis in Cancer and Other Diseases." *Nature.* 407.6801(2000):249-257.
Carmeliet. "Mechanisms of Angiogenesis and Arteriogenesis." *Nat. Med.* 6.3(2000):389-395.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chen et al. "Adipogenic Differentiation of Adipose Tissue-Derived Human Mesenchymal Stem Cells: Effects of Gastric Bypass Surgery." *Surg. Endosc.* 26(2012):3449-3456.
Chen et al. "Integrated Approach to Designing Growth Factor Delivery Systems." *FASEB J.* 21.14(2007):3896-3903.
Chen et al. "Polymeric Growth Factor Delivery Strategies for Tissue Engineering." *Pharm. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.
Choi et al. "In Vitro Mineralization by Preosteoblasts in Poly(DL-lactide-co-glycolide) Inverse Opal Scaffolds Reinforced with Hydrozyapatite Nanoparticles." *Langmuir.* 26.14(2010):12126-12131.
Choi et al. "Three-Dimentional Scaffolds for Tissue Engineering: The Importance of Uniformity in Pore Size and Structure." *Langmuir.* 26.24(2010):19001-19006.
Choi. "Replacement Organs, Hot Off the Press." *New Scientist.* 177.2379(2003):16.
Chou et al. "Characterization of Photocross Linked Alginate Hydrogels for Nucleus Pulposus Cell Encapsulation." *J. Biomed. Mater. Res. A.* 91A.1(2009):187-194.
Chromiak et al. "Bioreactor Perfusion System for the Long-Term Maintenance of Tissue-Engineered Skeletal Muscle Organoids." *In Vitro Cell Dev. Biol. Anim.* 34.9(1998):694-703.
Clauss et al. "Interstitial Transport of Rabbit and Sheep Antibodies in Normal and Neoplastic Tissues." *Cancer Res.* 50.12(1990):3487-3492.
Cohen et al. "Controlled Delivery Systems for Proteins Based on Poly(Lactic/Glycolic Acid) Microspheres." *Pharm. Res.* 8.6(1991):713-720.
Comisar et al. "Engineering RGD Nanopatterned Hydrogels to Control Preosteoblast Behavior: A Combined Computational and Experimental Approach." *Biomaterials.* 28(2007):4409-4417.
Conboy et al. "The Regulation of Notch Signaling Controls Satellite Cell Activation and Cell Fate Determination in Postnatal Myogenesis." *Dev. Cell.* 3.3(2002):397-409.
Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." *J. Biomed. Mater. Res.* 89A.2(2009):304-316.
Conn et al. "Purification of a Glycoprotein Vascular Endothelial Cell Mitogen From a Rat Glioma-Derived Cell Line." *PNAS.* 87.4(1990):1323-1327.
Cooper et al. "Extended Amplification In Vitro and Replicative Senescence: Key Factors Implicated in the Success of Human Myoblast Transplantation." *Hum. Gene Ther.* 14(2003):1169-1179.
Cornelison et al. "Single-Cell Analysis of Regulatory Gene Expression in Quiescent and Activated Mouse Skeletal Muscle Satellite Cells." *Dev. Biol.* 191.2(1997):270-283.

(56) References Cited

OTHER PUBLICATIONS

Cornelison et al. "Syndecan-3 and Syndecan-4 Specifically Mark Skeletal Muscle Satellite Cells and Are Implicated in Satellite Cell Maintenance and Muscle Regeneration." *Dev. Biol.* 239.1(2001):79-94.
Coulson et al. "Flow of Fluids through Granular Beds and Packed Columns." *Chemical Engineering.* New York: Pergamon Press. 2(1978):125-171.
Crameri et al. "Improved Green Fluorescent Protein by Molecular Evolution Using DNA Shuffling." *Nat. Biotechnol.* 14.3(1996):315-319.
Cullen et al. "Investigation of Vascular Endothelial Growth Factor Effects on Pulmonary Endothelial Monolayer Permeability and Neutrophil Transmigration." *Gen. Pharmacol.* 35.3(2000):149-157.
Curiel et al. "Tumor Immunotherapy: Inching Toward the Finish Line." *J. Clin. Invest.* 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." *J. Exp. Med.* 198.2(2003):293-303.
Dar et al. "Optimization of Cardiac Cell Seeding and Distribution in 3D Porous Alginate Scaffolds." *Biotechnol. Bioeng.* 80(2002):305-312.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol.* 165.1(2000):49-58.
De Temmerman et al. "Particulate Vaccines: On the Quest for Optimal Delivery and Immune Response." *Drug Disc. Today.* 16.13/14(2011):569-582.
Den Haan et al. "CD8+ by not CD8− Dendritic Cells Cross-Prime Cytotoxic T Cells In Vivo." *J. Exp. Med.* 192.12(2000):1685-1696.
Dennis et al. "Excitability and Contractility of Skeletal Muscle Engineered From Primary Cultures and Cell Lines." *Am. J. Physiol. Cell Physiol.* 280(2001):C288-C295.
Dennis et al. "Excitability and Isometric Contractile Properties of Mammalian Skeletal Muscle Constructs Engineered in vitro." *In Vitro Cell Dev. Biol. Anim.* 36.5(2000):327-335.
Dieu et al. "Selective Recruitment of Immature and Mature Dendritic Cells by Distinct Chemokines Expressed in Different Anatomic Sites." *J. Exp. Med.* 188.2(1988):373-386.
Doan et al. "Subcellular Localization of a Sporulation Membrane Protein is Achieved Through a Network of Interactions Along and Across the Septum." *Mol. Microbiol.* 55.6(2005):1767-1781.
Dor et al. "Making Vascular Networks in the Adult: Branching Morphogenesis Without a Roadmap." *Trends Cell Biol.* 13.3(2003):131-136.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS.* 90.8(1993):3539-3543.
Dranoff. "Cyotkines in Cancer Pathogenesis and Cancer Therapy." *Nat. Rev. Cancer.* 4.1(2004):11-22.
Dudley et al. "Adoptive Cell Transfer Therapy Following Non-Myeloablative by Lymphodepleting Chemotherapy for the Treatment of Patients with Refractory Metastatic Melanoma." *J. Clin. Oncol.* 23.10(2005):2346-2357.
Egholm et al. "Peptide Nucleic Acids (PNA). Oligonucleotide Analogues with an Achiral Peptide Backbone." *J. Am. Chem. Soc.* 114.5(1992):1895-1897.
Egholm et al. "PNA Hybridizes to Complementary Oligonucleotides Obeying the Watson-Crick Hydrogen-Bonding Rules." *Nature.* 365.6446(1993):566-568.
Ehrbar et al. "Endothelial Cell Proliferation and Progenitor Maturation by Fibrin-Bound VEGF Variants with Differential Susceptibilities to Local Cellular Activity." *J. Control. Release.* 101(2004):93-109.
Eiselt et al. "Porous Carriers for Biomedical Applications Based on Alginate Hydrogels." *Biomat.* 21.19(2000):1921-1927.
El-Backly et al. "Regeneration of Dentine/Pulp-Like Tissue Using a Dental Pulp Stem Cell/Poly(Lactic-Co-Glycolic) Acid Scaffold Construct in New Zealand White Rabbits." *Aust. Endod. J.* 34.2(2008):52-67.
Eldar et al. "Elucidating Mechanisms Underlying Robustness of Morphogen Gradients." *Curr. Opin. Genet. Dev.* 14.4(2004):435-439.
Eldar et al. "Robustness of the BMP Morphogen Gradient in *Drosophila* Embryonic Patterning." *Nature.* 419.6904(2002):304-308.
Eldar et al. "Self-Enhanced Ligand Degradation Underlies Robustness of Morphogen Gradients." *Dev. Cell.* 5.4(2003):635-646.
Engler et al. "Matrix Elasticity Directs Stem Cell Lineage Specification." *Cell.* 126.4(2006):677-689.
Ennett et al. "Temporally Regulated Delivery of VEGF in vitro and in vivo." *J. Biomed. Mater. Res. A.* 79.1(2006):176-184.
Faissner et al. "Boundaries and Inhibitory Molecules in Developing Neural Tissues." *Glia.* 13.4(1995):233-254.
Falsey et al. "Peptide and Small Molecule Microarray for High Throughput Cell Adhesion and Functional Assays." *Bioconjug. Chem.* 12.3(2001):346-353.
Farrar et al. "T Helper Subset Development: Roles of Instruction, Selection, and Transcription." *J. Clin. Invest.* 109.4(2002):431-435.
Ferrara et al. "Angiogenesis as a Therapeutic Target." *Nature.* 438.7070(2005):967-974.
Ferrara et al. "Discovery and Development of Bevacizumab, an Anti-VEGF Antibody for Treating Cancer." *Nat. Rev. Drug Discov.* 3.5(2004):391-400.
Fischer et al. "A Brilliant Monomeric Red Fluorescent Protein to Visualize Cytoskeleton Dynamics in *Dictyostelium*." *FEBS Lett.* 577.1-2(2004):227-232.
Fischer et al. "Visualizing Cytoskeleton Dynamics in Mammalian Cells Using a Humanized Variant of Monomeric Red Fluorescent Protein." *FEBS Lett.* 580.10(2006):2495-2502.
Folkman. "Angiogenesis." *Annu. Rev. Med.* 57(2006):1-18.
Fonseca et al. "Capitalizing on the Immunogenicity of Dying Tumor Cells." *Clin. Cancer Res.* 14.16(2008):1603-1608.
Fontaine et al. "Surgical Treatment of Peripheral Circulation Disorders." *Helv. Chir. Acta.* 21.56(1954):499-533. (German Original, No English Translation Available).
Fox. "Management of Worsening Multiple Sclerosis with Mitoxantrone: A Review." *Clin. Ther.* 28.4(2006):461-474.
Friedrich et al. "Promoter Traps in Embryonic Stem Cells: A Genetic Screen to Identify and Mutate Developmental Genes in Mice." *Genes Dev.* 5(1991):1513-1523.
Fukushima et al. "The Use of an Antifibrosis Agent to Improve Muscle Recovery After Laceration." *Am. J. Sports Med.* 29.4(2001):394-402.
Gamvrellis et al. "Vaccines that Facilitate Antigen Entry into Dendritic Cells." *Immunol. Cell Biol.* 82(2004):506-516.
GenBank Accession No. A32848.1, Jul. 5, 2002.
GenBank Accession No. AAA35789.1, Apr. 27, 1993.
GenBank Accession No. AAA56738.1, Dec. 7, 1994.
GenBank Accession No. AAA60552.1, Nov. 24, 2003.
GenBank Accession No. AAA64297.1, Mar. 24, 1995.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAI44040, Mar. 18, 2009.
GenBank Accession No. ABC86910, Jan. 3, 2011.
GenBank Accession No. CAA01954.1, Jun. 15, 1995.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. EF064765.1, Nov. 13, 2006.

(56) References Cited

OTHER PUBLICATIONS

GenBank Accession No. EU826563.1, Jul. 23, 2008.
GenBank Accession No. NM_000230.2, Dec. 17, 2012.
GenBank Accession No. NM_000514.3, Aug. 19, 2012.
GenBank Accession No. NM_000601.4, Nov. 25, 2012.
GenBank Accession No. NM_000614.3, Sep. 9, 2012.
GenBank Accession No. NM_000660.4, Dec. 9, 2012.
GenBank Accession No. NM_000800.3, Mar. 4, 2012.
GenBank Accession No. NM_ 001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_002506.2, Dec. 9, 2012.
GenBank Accession No. NM_002632.4, May 4, 2011.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_006068.4, Oct. 28, 2012.
GenBank Accession No. NM_016562.3, Jan. 6, 2013.
GenBank Accession No. NM_030956.3, Oct. 28, 2012.
GenBank Accession No. Nm 033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_ 001096124.1, Dec. 16, 2012.
GenBank Accession No. NP_002010.2, Dec. 9, 2012.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_006059.2, Oct. 28, 2012.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Glasbey et al. "Image Analysis and Three-Dimensional Modelling of Pores in Soil Aggregates." *Eur. J. Soil Sci.* 42.2(1991):479-486.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngol. Head Neck Surg.*130.10(2004):1191-1196.
Gros et al. "A Common Somitic Origin for Embryonic Muscle Progenitors and Satellite Cells." *Nature.* 435(2005):954-958.
Gullberg et al. "Extracellular Matrix and Its Receptors During Development." *Int. J. Dev. Biol.* 39(1995):845-854.

Gupta et al. "Magnetically Controlled Targeted Micro-Carrier Systems." *Life Sci.* 44.3(1989):175-186.
Gussoni et al. "Dystrophin Expression and in the mdx Mouse Restored by Stem Cell Transplantation." *Nature.* 401(1999):390-394.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.
Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *PNAS.* 96(1999):9305-9310.
Hashimoto et al. "Development of Alginate Wound Dressings Linked with Hybrid Peptides Derived from Laminin and Elastin." *Biomaterials.* 25.7-8(2004):1407-1414.
Hawke et al. "Myogenic Satellite Cells: Physiology to Molecular Biology." *J. Appl. Physiol.* 91(2001):534-551.
Heath. "Cells for Tissue Engineering." *Trends Biotechnol.* 18.1(2006):17-19.
Helm et al. "Synergy Between Interstitial Flow and VEGF Directs Capillary Morphogenesis in vitro Through a Gradient Amplification Mechanism." *PNAS.* 102.44(2005):15779-15784.
Henry et al. "The VIVA Trial: Vascular Endothelial Growth Factor in lschemia for Vascular Angiogenesis." *Circulation.* 107.10(2003):1359-1365.
Hermanson. *Bioconjugate Techniques*. New York: Academic Press. (1996):152-185.
Heslop et al. "Transplanted Primary Neonatal Myoblasts can Give Rise to Functional Satellite Cells as Identified Using the Myf5nlacZl+ Mouse." *Gene Ther.* 8(2001):778-783.
Hildner et al. "Batf3 Deficiency Reveals a Critical Role for CD8α+ Dendritic Cells in Cytotoxic T Cell Immunity." *Science.* 322.5904(2008):1097-1100.
Hill et al. "Designing Scaffolds to Enhance Transplanted Myoblast Survival and Migration." *Tissue Engin.* 12.5(2006):1295-1304.
Hill et al. "Muscle Satellite (Stem) Cell Activation During Local Tissue Injury and Repair." *J. Anat.* 203.1(2003):89-99.
Hill. "Macroporous Scaffold Architecture, Peptide, HGF/FGF and Myoblast Incorporation Enhance Myogenesis." *IADR/AADR/CADR 83rd General Session.* (Mar. 9-12, 2005). Poster #2829.
Hirano et al. "Peptide and Protein Presenting Materials for Tissue Engineering." *Adv. Mat.* 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." *PNAS.* 95.23(1998):13806-13811.
Hodi et al. "Immunologic and Clinical Effects of Antibody Blockade of Cytotoxic T Lymphocyte-Associated Antigen 4 in Previously Vaccinated Cancer Patients." *PNAS.* 105.8(2008):3005-3010.
Horsley et al. "IL-4 Acts as a Myoblast Recruitment Factor During Mammalian Muscle Growth." *Cell.* 113.4(2003):483-494.

(56) References Cited

OTHER PUBLICATIONS

Hsiong et al. "Differentiation Stage Alters Matrix Control of Stem Cells." *J. Biomed. Mater. Res. Part A.* 8(2007):145-156.
Huang et al. "Fabrication and in vitro Testing of Polymeric Delivery Systems for Condensed DNA." *J. Biomed. Mater. Res.* 67(2003):1384-1392.
Huang et al. "Long-Term In Vivo Gene Expression via Delivery of PEI-DNA Condensates From Porous Polymer Scaffolds." *Hum. Gene Ther.* 16.5(2005):609-617.
Hubbell et al. "Materials Engineering for Immunomodulation." *Nature.* 462(2009):449-460.
Hubbell. "Biomaterials in Tissue Engineering." *Bio/Tech.* 13(1995):565-576.
Huebsch et al. "Harnessing Traction-Mediated Manipulation of the Cell/Matrix Interface to Control Stem-Cell Fate." *Nat. Mater.* 9.6(2010):518-526.
Hwang et al. "Fabrication of Three-Dimensional Porous Cell-Laden Hydrogel for Tissue Engineering." *Biofabrication.* 2.3(2010):035003.
Ishihara et al. "Roles of Bradykinin in Vascular Permeability and Angiogenesis in Solid Tumor." *Int. Immunopharmacol.* 2.4(2002):499-509.
Iwamoto et al. "Preparation of an Ionic Polymer Gel Microactuator and Measurement of its Periodic Motions." *Nippon Kagaku Kaishi.* 9(1997):609-614. (Japanese Original and English Abstract).
Jain. "Molecular Regulation of Vessel Maturation." *Nat. Med.* 9.6(2003):685-693.
Jain. "The Manufacturing Techniques of Various Drug Loaded Biodegradable Poly(lactide-co-glycolide) (PLGA) Devices." *Biomater.* 21.23(2000):2475-2490.
Jankovic et al. "In the Absence of Il-12, CD4+ T Cell Responses to Intracellular Pathogens Fail to Default to a Th2 Pattern and are Host Protective in an IL-10-/- Setting." *Immunity.* 16.3(2002):429-439.
Jego et al. "Plasmacytoid Dendritic Cells Induce Plasma Cell Differenetiation Through Type I Interferon and Interleukin 6." *Immunity.* 19.2(2003):225-234.
Jiang et al. "Self-Organization of Periodic Patterns by Dissociated Feather Mesenchymal Cells and the Regulation of Size, No. And Spacing of Primordia." *Development.* 126.22(1999):4997-5009.
Jinushi et al. "Enhancing the Clinical Activity of Granulocyte-Macrophage Colony-Stimulating Factor-Secreting Tumor Cell Vaccines." *Immunol. Rev.* 222(2008):287-298.
Jinushi et al. "MFG-E8-Mediated Uptake of Apoptotic Cells by APCs Links the Pro- and Antiinflammatory Activities of GM-CSF." *J. Clin. Invest.* 117.7(2007):1902-1913.
Johnson et al. "Activation of Skeletal Muscle Satellite Cells and the Role of Fibroblast Growth Factor Receptors." *Exp. Cell Res.* 219.2(1995):449-453.
Juntanon et al. "Electrically Controlled Release of Sulfosalicylic Acid from Crosslinked Poly(Vinyl Alcohol) Hydrogel." *Int. J. Pharm.* 356(2008):1-11.
Kanzler et al. "Therapeutic Targeting of Innate Immunity with Toll-Like Receptor Agaonists and Antagonists." *Nat. Med.* 13.5(2007):552-559.
Kawai et al. "Innate Immune Recognition of Viral Infection." *Nat. Immunol.* 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release.* 62.12(1999):279-287.
Khownium et al. "Novel Endotoxin-Compounds with Terephthalaldehyde-bis-guanylhydrazone Scaffolds." *Bioorg. Med. Chem. Lett.* 16(2006):1305-1308.
Kim et al. "An Overview of Cartilage Tissue Engineering." *Yonsei Med. J.* 41.6(2000):766-773.
Kim et al. "Multifunctional Capsule-in-Capsules for Immunoprotection and Trimodal Imaging." *Angew. Chem. Int. Ed.* 50.10(2011):2317-2321.
Kim et al. "The Effect of VEGF on the Myogenic Differentiation of Adipose Tissue Derived Stem Cells Within Thermosensitive Hydrogel Matrices." *Biomaterials.* 31.6(2010):1213-1218.

Kinoshita et al. "Successive Injections in MDX Mice of Myoblasts Grown with bFGF." *Neuromusc. Disord.* 6.3(1996):187-193.
Kisak et al. "The Vesosome—A Multicompartment Drug Delivery Vehicle." *Curr. Med. Chem.* 11.2(2004):199-219.
Klebanoff et al. "CD8+ T-Cell Memory in Tumor Immunology and Immunotherapy." *Immunol. Rev.* 211(2006):214-224.
Klinman. "Immunotherapeutic Uses of CpG Oligodeoxynucleotides." *Nat. Rev. Immunol.* 4.4(2004):249-258.
Kondo et al. "A Reaction-Diffusion Wave on the Skin of the Marine Angelfish Pomacanthus." *Nature.* 376(2002):765-768.
Kong et al. "Controlling Degradation of Hydrogels via the Size of Crosslinked Junctions." *Adv. Mater.* 16.21(2004):1917-1921.
Kong et al. "Controlling Rigidity and Degradation of Alginate Hydrogels via Molecular Weight Distribution." *Biomacromolec.* 5.5(2004):1720-1727.
Kong et al. "Decoupling the Dependence of Rheological/Mechanical Properties of Hydrogels from Solids Concentration." *Polymer.* 43(2002):6239-6246.
Kong et al. "Design of Biodegradable Hydrogel for the Local and Sustained Delivery of Angiogenic Plasmid DNA." *Pharma. Res.* 25.5(2008):1230-1238.
Kong et al. "Designing Alginate Hydrogels to Maintain Viability of Immobilized Cells." *Biomat.* 24.22(2003):4023-4029.
Kong et al. "Non-Viral Gene Delivery Regulated by Stiffness of Cell Adhesion Substrates." *Nat. Mater.* 4(2005):406-410.
Krieg. "Development of TLR9 Agonists for Cancer Therapy." *J. Clin. Invest.* 117.5(2007):1184-1194.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kumamoto et al. "Induction of Tumor-Specific Protective Immunity by in situ Langerhans Cell Vaccine." *Nat. BioTechnol.* 20.1(2002):64-69.
Kumar et al. "Toll-Like Receptors and Innate Immunity." *Biochem. Biophys. Res. Commun.* 388.4(2009):621-625.
Kurts et al. "CD8 T Cell Ignorance or Tolerance to Islet Antigens Depends on Antigen Dose." *PNAS.* 96.22(1999):12703-12707.
Kwon et al. "Electrically Erodible Polymer Gel for Controlled Release of Drugs." *Nature.* 354(1991):291-293.
Kwon et al. "In vivo Targeting Dendritic Cells for Activation of Cellular Immunity Using Vaccine Carriers Based on pH-Responsive Microparticles." *PNAS.* 102.51(2005):18264-18268.
Langenkamp et al. "Kinetics of Dendritic Cell Activation: Impact on Priming of TH1, TH2 and Nonpolarized T Cells." *Nat. Immunol.* 1.4(2000):311-316.
Langer et al. "Tissue Engineering." *Science.* 260(1993):920-926.
Lanzavecchia et al. "Regulation of T Cell Immunity by Dendritic Cells." *Cell.* 106.3(2001):263-266.
Lao et al. "Magnetic and Hydrogel Composite Materials for Hyperthermia Applications." *J. Mater. Sci. Mater. Med.* 15.10(2004):1061-1064.
Lauterbach et al. "Mouse CD8α+ DCs and Human BDCA3+ DCs are Major Producers of IFN-γ in Response to Poly IC." J. Exp. Med. 207.12(2010):2703-2717.
Leach et al. "Coating of VEGF-Releasing Scaffolds with Bioactive Glass for Angiogenesis and Bone Regeneration." *Biomater.* 27.17(2006):3249-3255.
Lee et al. "Engineering Liver Tissue Spheroids with Inverted Colloidal Crystal Scaffolds." *Biomater.* 30.27(2009):4687-4694.
Lee et al. "Hydrogel Formation via Vell Crosslinking." *Adv. Mat.* 15.21(2003):1828-1832.
Lee et al. "Hydrogels for Tissue Engineering." *Chem. Rev.* 101. 7(2001):1869-1879.
Lefaucheur et al. "The Cellular Events of Injured Muscle Regeneration Depend on the Nature of the Injury." *Neuromusc. Disorders.* 5.6(1995):501-509.
Lensch et al. "Scientific and Clinical Opportunities for Modeling Blood Disorders With Embryonic Stem Cells." *Blood.* 107. 7(2006):2605-2612.

(56) References Cited

OTHER PUBLICATIONS

Leor et al. "Cells, Scaffolds, and Molecules for Myocardial Tissue Engineering." *Pharmacol. Therapeutics.* 105(2005):151-163.
Leshem et al. "Hepatocyte Growth Factor (HGF) Inhibits Skeletal Muscle Cell Differentiation: A Role for the bHLH Protein Twist and the cdk Inhibitor p27." *J. Cell. Physiol.* 184(2000):101-109.
Letsinger et al. "Phosphoramidate Analogs of Oligonucleotides." *J. Org. Chem.* 35.11(1970):3800-3803.
Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Effects of Three-Dimensional Scaffolds on Cell Organization and Tissue Development." *Biotech. Bioprocess Eng.* 6.5(2001):311-325.
Li. "TNF-α is a Mitogen is Skeletal Muscle." *Am. J. Physiol. Cell Physiol.* 285(2003):C370-C376.
Lipton et al. "Developmental Fate of Skeletal Satellite Cells." *Science.* 205(1979):1292-1294.
Liu et al. "Nanostructured Materials Designed for Cell Binding and Transduction." *Biomacromolecules.* 2.2(2001):362-368.
Liu. "Dendritic Cell Subsets and Lineages, and Their Functions in Innate and Adaptive Immunity." *Cell.* 106.3(2001):259-262.
Lu et al. "Muscle-Derived Stem Cells Seeded Into Acellular Scaffolds Develop Calcium-Dependent Contractile Activity That is Modulated by Nicotinic Receptors." *Urology.* 61.6(2003):1285-1291.
Lubeck. "The Costs of Musculoskeletal Disease: Health Needs Assessment and Health Economics." *Best Pract. Res. Clin. Rheumatol.* 17.3(2003):529-539.
Lumelsky et al. "Differentiation of Embryonic Stem Cells to Insulin-Secreting Structures Similar to Pancreatic Islets." *Science.* 292. 5520(2001):1389-1394.
Lutolf et al. "Repair of Bone Defects Using Synthetic Mimetics of Collagenous Extracellular Matrices." *Nat. Biotechnol.* 21.5(2003):513-518.
López et al. "Magnetic Applications of Polymer Gels." *Macromol. Symp.* 166.1(2001):173-178.
Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N. Y. Acad. Sci.* 795(1996):60-70.
Maini. "Spatial and Spatio-Temporal Patterns in a Cell-Haptotaxis Model." *J. Math. Biol.* 27.5(1989):507-522.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219. 1(1995):169-179.
Martinsen et al. "Alginate as Immobilization Material." *Biotech. Bioeng.* 33.1(1989):79-89.
Marui et al. "Simultaneous Application of Basic Fibroblast Growth Factor and Hepatocyte Growth Factor to Enhance the Blood Vessels Formation." *J. Vasc. Surg.* 41.1(2005):82-90.
Massia et al. "An RGD Spacing of 440 nm is Sufficient for Integrin αvβ3-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McKinney-Freeman et al. "Muscle-Derived Hematopoietic Stem Cells are Hematopoietic in Origin." *PNAS.* 99.3(2002):1341-1346.
McPherron et al. "Regulation of Skeletal Muscle Mass in Mice by a New TGF-β Superfamily Member." *Nature.* 387(1997):83-90.
Meier et al. "Peptide Nucleic Acids (PNAs)—Unusual Properties of Noionic Oligonucleotide Analogues." *Angew. Chem. Int. Ed.* 31.8(1992):1008-1010.
Melero-Martin et al. "Engineering Robust and Functional Vascular Networks In Vivo With Human Adult and Cord Blood-Derived Progenitor Cells." *Circ. Res.* 103.2(2008):194-202.
Mellman et al. "Dendritic Cells: Specialized and Regulated Antigen Processing Machines." *Cell.* 106.3(2001):255-258.
Menetrey et al. "Suturing Versus Immobilization of a Muscle Laceration: A Morphological and Functional Study in a Mouse Model." *Am. J. Sports Med.* 27.2(1999):222-229.
Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).
Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Miller et al. "Lipopolysaccharide Sequestrants: Structural Correlates of Activity and Toxicity in Novel Acylhomospermines." *J. Med. Chem.* 48(2005):2589-2599.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Miyata et al. "Biomolecule-Sensitive Hydrogels." *Adv. Drug Deliv. Rev.* 54.1(2002):79-98.
Mohan et al. "Novel Porous, Polysaccharide Scaffolds for Tissue Engineering Applications." *Trends Biomater. Artif. Organs.* 18.2(2005):219-224.
Moioli et al. "Matrices and Scaffolds for Drug Delivery in Dental, Oral and Craniofacial Tissue Engineering." *Adv. Drug Deliv. Rev.* 59.4-5(2007):308-324.
Mooney et al. "Switching From Differentiation to Growth in Hepatocytes: Control by Extracellular Matrix." *J. Cell. Phys.* 151. 3(1992):497-505.
Moser et al. "Dendritic Cell Regulation of TH1-TH2 Regulation." *Nat. Immunol.* 1.3(2000):199-205.
Murdan. "Electro-Responsive Drug Delivery from Hydrogels." *J. Control. Release.* 92(2003):1-17.
Nagai et al. "A Variant of Yellow Fluorescent Protein with Fast and Efficient Maturation for Cell-Biological Applications." *Nat. Biotechnol.* 20.1(2002):87-90.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_003265, Dec. 30, 2012.
NCBI Accession No. NM_004119, Apr. 14, 2013.
NCBI Accession No. NM_006274.2, Mar. 31, 2013.
NCBI Accession No. NM_017442, Apr. 14, 2012.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_003367, Jan. 30, 2011.
NCBI Accession No. NP_059138, Apr. 14, 2012.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Niamlang et al. "Electrically Controlled Release of Salicylic Acid from poly(p-phenylene vinylene) Polyacrylamide Hydrogels." *Int. J. Pharm.* 371(2009):126-133.
Nicodemus et al. "Cell Encapsulation in Biodegradable Hydrogels for Tissue Engineering Applications." *Tissue Eng. Part B Rev.* 14.2(2008):149-165.
Noguera-Troise et al. "Blockade of Dll4 Inhibits Tumour Growth by Promoting Non-Productive Angiogenesis." *Nature.* 444. 7122(2006):1032-1037.
O'Garra et al. "Are Dendritic Cells Afraid of Commitment?" *Nat. Immunol.* 5.12(2004):1206-1208.

(56) References Cited

OTHER PUBLICATIONS

O'Shea et al. "Type 1 IFNs and Regulation of TH1 Responses: Enigmas Both Resolved and Emerge." *Nat. Immunol.* 1.1(2000):17-19.
Ohashi et al. "Surgical Excision Combined with Autologous Whole Tumor Cell Vaccination is an Effective Therapy for Murine Neuroblastoma." *J. Ped. Surg.* 41(2006):1361-1368.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell No. And Acquisition of Effector Cell Phenotype During Lethal Infection." *Immunity.* 31.5(2009):772-786.
Orner et al. "Arrays for the Combinatorial Exploration of Cell Adhesion." *J. Am. Chem. Soc.* 126.35(2004):10808-10809.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Palacio et al. "Interleukin 10 and Tumor Necrosis Factor α Gene Expression in Respiratory and Peripheral Muscles." *Arch. Bronconeumol.* 38.7(2002):311-316. (Spanish Original and English Abstract).
Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Parker et al. "Effect of Mitoxantrone on Outcome of Children with First Relapse of Acute Lymphoblastic Leukemia (ALL R3): An Open-Label Radomised Trial." *Lancet.* 376(2010):2009-2017.
Partridge et al. "Conversion of mdx Myofibres From Dystrophin-Negative to -Positive by Injection of Normal Myoblasts." *Nature.* 337.6203(1989):176-179.
Pedersen et al. "Induction of Regulatory Dendritic Cells by Desamethasone and 1α,25-Dihydroxyvitamin D3." *Immunol. Lett.* 91(2004):63-69.
Pelinkovic et al. "Tissue Engineering and Gene Therapy of the Muscoskeletal System with Muscle Cells." *Z. Orthop. Ihre Grenzgeb.* 138.5(2000):402-406. (German Original and English Abstract).
Peters et al. "Engineering Vascular Networks in Porous Polymer Matrices." *J. Biomed. Mater. Res.* 60.4(2002):668-678.
Phillippi. "Patterning of Multiple Cell Lineages from a Single Stem Cell Population." *Annual Meeting of the American Society for Cell Biology.* (Dec. 10, 2006).
Pluen et al. "Role of Tumor-Host Interactions in Interstitial Diffusion of Macromolecules: Cranial vs. Subcutaneous Tumors." *PNAS.* 98.8(2001):4628-4633.
Pooyan et al. "Conjugates Beating Multiple Formyl-Methionyl Peptides Display Enhanced Binding to, but not Activation of Phagocytic Cells." *Bioconjugate Chem.* 13.2(2002):216-223.
Pope et al. "Organ-Specific Regulation of the CD8 T Cell Response to *Listeria monocytogenes* Infection." *J. Immunol.* 166(2001):3402-3409.
Porter et al. "Separation of Natural Populations of Coliform Bacteria from Freshwater and Sewage by Magnetic-Bead Cell Sorting." *J. Microbiol. Meth.* 33.3(1998):221-226.
Pouzet et al. "Factors Affecting Functional Outcome After Autologous Skeletal Myoblast Transplantation." *Ann. Thorac. Surg.* 71(2001):844-851.
Pulendran et al. "Flt3-Ligand and Granulocyte Colony-Stimulating Factor Mobilize Distinct Human Dendritic Cell Subsets In Vivo." *J. Immunol.* 165(2000):566-572.
Qu et al. "Development of Approaches to Improve Cell Survival in Myoblast Transfer Therapy." *J. Cell Biol.* 142.5(1998):1257-1267.
Qu-Petersen et al. "Identification of a Novel Population of Muscle Stem Cells in Mice: Potential for Muscle Regeneration." *J. Cell Biol.* 157.5(2002):851-864.
Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Qui et al. "Environment-Sensitive Hydrogels for Drug Delivery." *Adv. Drug Deliv. Rev.* 53.3(2001):321-339.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation.* 108.16(2003):1933-1938.
Randolph et al. "Migration of Dendritic Cell Subsets and Their Precursors." *Annu. Rev. Immunol.* 26(2008):293-316.
Rappolee et al. "Macrophage-Derived Growth Factors." *Curr. Top. Microbiol. Immunol.* 181(1992):87-140.
Rapraeger. "Syndecan-Regulated Receptor Signaling." *J. Cell. Biol.* 149.5(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles of mdx and Control Mice." *Eur. J. Neurosci.*10(1998):366. (Abstract #153.07).
Reis e Sousa. "Activation of Dendritic Cells: Translating Innate into Adaptive Immunity." *Curr. Opin. Immunol.* 16.1(3005):21-25.
Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.
Richards Grayson et al. "Multi-Pulse Drug Delivery From a Resorbable Polymeric Microchip Device." *Nat. Mater.* 2.11(2003):767-772.
Richardson et al. "Polymeric System for Dual Growth Factor Delivery." *Nat. Biotech.* 19.11(2001):1029-1034.
Riddle et al. "Role of Poly(lactide-co-glycolide) Particle Size on Gas-Foamed Scaffolds." *J. Biomater. ScL Polym. Ed.* 15.12(2004):1561-1570.
Ridgway et al. "Inhibition of Dll4 Signalling Inhibits Tumour Growth by Deregulating Angiogenesis." *Nature.* 444.7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rizzo et al. "An Improved Cyan Fluorescent Protein Variant Useful for FRET." *Nat. Biotechnol.* 22.4(2004):445-449.
Rosenberg et al. "Cancer Immunotherapy: Moving Beyond Current Vaccines." *Nat. Med.* 10.9(2004):909-915.
Roth et al. "SC68896, a Novel Small Molecule Proteasome Inhibitor, Exerts Antiglioma Activity In vitro and In vivo." *Clin. Cancer Res.*15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol.* 295(2008):1037-1044.
Rowley et al. "Alginate Type and RGD Density Control Myoblast Phenotype." *J. Biomed. Mater. Res.* 60.2(2002):217-233.
Rowley et al. "Biomaterials to Spatially Regulate Cell Fate." *Adv. Mater.* 14.12(2002):886-889.
Rowley. "Alginate Hydrogels as Synthetic Extracellular Matrix Materials." *Biomaterials.* 20.1(1999):45-53.
Rubin et al. "Dissociation of Heparan Sulfate and Receptor Binding Domains of Hepatocyte Growth Factor Reveals That Heparan Sulfate-c-Met Interaction Factilitates Signaling." *J. Biol. Chem.* 276.35(2001):32977-32983.
Ryten et al. "ATP Regulates the Differentiation of Mammalian Skeletal Muscle by Activation of a P2X5 Receptor on Satellite Cells." *J. Cell. Biol.* 158.2(2002):345-355.

(56) References Cited

OTHER PUBLICATIONS

Ryu et al. "The Construction of Three-Dimensional Micro-Fluidic Scaffolds of Biodegradable Polymers by Solvent Vapor Based Bonding of Micro-Molded Layers." *Biomaterials*. 28.6(2007):1174-1184.
Salem et al. "Defining the Antigen-Specific T-Cell Response to Vaccination and Poly(I:C)/TLR3 Signaling." *J. Immunother.* 28.3(2005):220-228.
Salvador et al. "Combination of Immune Stimulating Adjuvants With Poly(lactide-co-glycolide) Microspheres Enhances the Immune Response of Vaccines." *Vaccine*. 30.3(2011):589-596.
Salvay et al. "Inductive Tissue Engineering with Protein and DNA-Releasing Scaffolds." *Mol. Biosyst.* 2.1(2006):36-48.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.
Sarkar et al. "Condensation of Oligonucleotides Assembled into Nicked and Gapped Duplexes: Potential Structures for Oligonucleotide Delivery." *Nucleic Acids Res*. 33.1(2005):143-151.
Saxena et al. "Skeletal Muscle Tissue Engineering Using Isolated Myoblasts on Synthetic Biodegradable Polymers: Preliminary Studies." *Tissue Eng.* 5.6(1999):525-532.
Schaefer et al. Innate mmunity in the Human Female Reproductive Tract: Antiviral Response of Uterine Epithelial Cells to TLR3 Agonist Poly(I:C). *J. Immunol.* 174(2005):992-1002.
Scheel et al. "Toll-Like Receptor-Dependent Activation of Several Human Blood Cell Types by Protamine Condensed mRNA." *Eur. J. Immunol.* 35(2005):1557-1566.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS*. 103.28(2006):10729-10734.
Schuler et al. "The Use of Dendritic Cells in Cancer Immunotherapy." *Curr. Opin. Immunol.* 15.2(2003):138-147.
Seale et al. "Pax7 Is Required for the Specification of Myogenic Satellite Cells." *Cell*. 102.6(2000):777-786.
Shakweh et al. "Design and Characterisation of Poly(lactide-co-glycolide) Small Particulate Systems for the Delivery of Immunostimulant CpG Oligonucleotide." *J. Nanosci. Nanotechnol*. 6.9-10(2006):2811-2820.
Shaner et al. "Improved Monomeric Red, Orange and Yellow Fluorescent Proteins Derived from *Discosoma* sp. Red Fluorescent Protein." *Nat. Biotechnol*. 22.12(2004):1567-1572.
Shansky et al. "Letter to the Editor: A Simplified Method for Tissue Engineering Skeletal Muscle Organoids In Vitro." *In Vitro Cell. Dev. Biol.* 33(1997):659-661.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release*. 64.1-3(2000):91-102.
Shi et al. "A Novel Toll-Like Receptor that Recognizes Vascular Stomatitis Virus." *J. Biol. Chem*. 286.6(2011):4517-4524.
Shoichet et al. "Stability of Hydrogels Used in Cell Encapsulation: An In Vitro Comparison of Alginate and Agarose." *Biotechnol. Bioeng.* 50(1996):374-381.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science*. 314. 5804(2006):1447-1450.
Silva et al. "Material-Based Deployment Enhances Efficacy of Endothelial Progenitor Cells." *PNAS*. 105.38(2008):14347-14352.
Silva et al. "Spatiotemporal Control of Vascular Endothelial Growth Factor Delivery From Injectable Hydrogels Enhances Angiogenesis." *J. Thromb. Haemost.* 5.3(2007):590-598.

Skokos et al. "CD8– DCs Induce IL-12-Independent Th1 Differentiation Through Delta 4 Notch-Like Ligand in Response to Bacterial LPS." *J. Exp. Med*. 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol*. 175. 1(2002):112-126.
Skuk et al. "Myoblast Transplantation: The Current Status of a Potential Therapeutic Tool for Myopathies." *J. Musc. Res. Cell. Motil.* 24.4-6(2003):285-300.
Smidsrød et al. "Alginate as Immobilization Matrix for Cells." *Trends Biotechnol*. 8.3(1990):71-78.
Sohier et al. "Critical Factors in the Design of Growth Factor Releasing Scaffolds for Cartilage Tissue Engineering." *Exp. Opin. Drug Deliv*. 5.5(2008):543-566.
Steinman et al. "Taking Dendritic Cells into Medicine." *Nature*. 449.7161(2007):419-426.
Storrie et al. "Sustained Delivery of Plasmid DNA From Polymeric Scaffolds for Tissue Engineering." *Adv. Drug Deliv. Rev*. 58.4(2006):500-514.
Straub et al. "Animal Models for Muscular Dystrophy Show Different Patterns of Sarcolemmal Distruption." *J. Cell Biol*. 139. 2(1997):375-385.
Sun et al. "Sustained Vascular Endothelial Growth Factor Delivery Enhances Angiogenesis and Perfusion in Ischemic Hind Limb." *Pharm. Res*. 22.7(2005):1110-1116.
Takahashi et al. "Induction of Pluripotent Stem Cells from Adult Human Fibroblasts by Defined Factors." *Cell*. 131.5(2007):861-872.
Takeshita et al. "Therapeutic Angiogenesis." *J. Clin. Invest*. 93.2(1994):662-670.
Tamura et al. "Immunotherapy of Tumors with Autologous Tumor-Derived Heat Shock Protein Preparations." *Science*. 278. 3(1997):117-120.
Tanaka et al. "Collapse of Gels in an Electric Field." *Science*. 218(1982):467-469.
Tatsumi et al. "HGF/SF Is Present in Normal Adult Skeletal Muscle and Is Capable of Activating Satellite Cells." *Dev. Biol*. 194. 1(1998):114-128.
Ten Dijke et al. "Growth Factors for Wound Healing." *Nat. Biotechnol*. 7(1989):793-798.
Thurston et al. "The Delta Paradox: DLL4 Blockade Leads to More Tumour Vessels but Less Tumour Growth." *Nat. Rev. Cancer*. 7.5(2007):327-331.
Tidball. "Inflammatory Cell Response to Acute Muscle Injury." *Med. Sci. Sports Exerc*. 27.7(1995):1022-1032.
Tomer et al. "Electrically Controlled Release of Macromolecules from Cross-Linked Hyaluronic Acid Hydrogels." *J. Control. Release*. 33.3(1995):405-413.
Tourniaire et al. "Polymer Microarrays for Cellular Adhesion." *Chem. Commun*. 20(2006):2118-2120.
Tsien. "The Green Fluorescent Protein." *Annu. Rev. Biochem*. 67(1998):509-544.
Turing. "Discussion: Turing's Theory of Morphogenesis—It's Influence on Modelling Biological Pattern and Form." *Bull. Math. Biol*. 52.1-2(1990):119-159.
Turing. "The Chemical Basis of Morphogenesis." *Philosophical Transactions of the Royal Society of London*. Series B. 237. 641(1952):37-72.
Uchida et al. "Immunization by Particle Bombardment of Antigen-Loaded poly-(DL-lactide-co-glycolide) Microspheres in Mice." *Vaccine*. 12(2006):2120-2130.
Ugarte et al. "Notch Signaling Enhances Osteogenic Differentiation While Inhibiting Adipogenesis in Primary Human Bone Marrow Stromal Cells." *Exp. Hematol*. 37(2009):867-875.
Urbanek et al. "Stem Cell Niches in the Adult Mouse Heart." *PNAS*. 103.24(2006):9226-9231.
Van Duin et al. "Triggering TLR Signaling in Vaccination." *Trends Immunol*. 27.1(2006):49-55.
Vandenburgh et al. "Tissue-Engineered Skeletal Muscle Organoids for Reversible Gene Therapy." *Hum. Gene Ther*. 17(1996):2195-2200.

(56) References Cited

OTHER PUBLICATIONS

Vieira et al. "The Bulk of Endogenously Produced IgG2a is Eliminated From the Serum of Adult C57BL/6 Mice With a Half-Life of 6-8 Days." *Eur. J. Immunol.* 16.7(1986):871-874.
Vieira et al. "The Half-Lives of Serum Immunoglobulins in Adult Mice." *Eur. J. Immunol.* 18.2(1988):313-316.
Villadangos et al. "Intrinsic and Cooperative Antigen-Presenting Functions of Dendritic-Cell Subsets in vivo." *Nat. Rev. Immunol.* 7.7(2007):543-555.
Villadangos. "Presentation of Antigens by MHC Class II Molecules: Getting the Most Out of Them." *Molec. Immunol.* 38.5(2001):329-346.
Von Dassow et al. "The Segment Polarity Network is a Robust Developmental Module." *Nature.* 406.6792(2000):188-192.
Wakim et al. "Dendritic Cell-Induced Memory T Cell Activation in Nonlymphoid Tissues." *Science.* 319(2008):198-202.
Waldron-Lynch et al. "Advances in Type 1 Diabetes Therapeutics: Immunomodulation and β-Cell Savage." *Endocrinol. Metab. Clin. North Am.* 38.2(2009):303-317.
Wan et al. "Peritoneal Macrophage Uptake, Pharmacokinetics and Biodistribution of Macrophage-Targeted PEG-fMLF (N-Formyl-Methionyl-Leucyl-Phenylalanine) Nanocarriers for Improving HIV Drug Delivery." *Pharm. Res.* 24.11(2007):2110-2119.
Wang et al. "Biological Activity of Bevacizumab, a Humanized Anti-VEGF Antibody in vitro." *Angiogenesis.* 7.4(2004):335-345.
Wang et al. "Evolution of New Nonantibody Proteins via Iterative Somatic Hypermutation." *PNAS.* 101.48(2004):16745-16749.
Wei et al. "Global Mapping of H3K4me3 and H3K27me3 Reveals Specificity in Plasticity in Lineage Fate Determination of Differentiating CD4+ T Cells." *Immunity.* 30.1(2009):155-167.
Wernig et al. "Function of Skeletal Muscle Tissue Formed After Myoblast Transplantation into Irradiated Mouse Muscles." *J. Physiol.* 522.2(2000):333-345.
White et al. "Leukemia Inhibitory Factor Enhances Regeneration in Skeletal Muscles After Myoblast Transplantation." *Musc. Nerve.* 24.5(2001):695-697.
World Health Organization. "Global Burden of Musculoskeletal Disease Revealed in new WHO Report." *Bull. World Health Organ.* 81.11(2003):853-854.
World Health Organization. "The World Health Report 2004: Changing History." *The World Health Report.* (2004):1-169.
Wright et al. "Muscle-Based Gene Therapy and Tissue Engineering for the Musculoskeletal System." *Drug Disc. Today.* 6.14(2001):728-733.
Xie et al. "Preparation and Application of Surface-Coated Superparamagnetic Nanobeads in the Isolation of Genomic DNA." *J. Magn. Magnetic Mater.* 277.1(2004):16-23.
Yancopoulos et al. "Vascular-Specific Growth Factors and Blood Vessel Formation." *Nature.* 407.6801(2000):242-248.
Yu et al. "Induced Pluripotent Stem Cell Lines Derived from Human Somatic Cells." *Science.* 318.5858(2007):1917-1920.
Yuen et al. "Mimicking Nature by Codelivery of Stimulant and Inhibitor to Create Temporally Stable and Spatially Restricted Angiogenic Zones." *PNAS.* 107.42(2010):17933-17938.
Yuk et al. "Electric Current-Sensitive Drug Delivery System Using Sodium Alginate/Polyacrylic Acid Composites." *Pharm. Res.* 9.7(1992):955-957.
Zammit et al. "Kinetics of Myoblast Proliferation Show That Resident Satellite Cells are Competent to Fully Regenerate Skeletal Muscle Fibers." *Exp. Cell Res.* 281.1(2002):39-49.
Zammit et al. "Muscle Satellite Cells Adopt Divergent Fates: A Mechanism for Self-Renewal?" *J. Cell Biol.* 166.3(2004):347-357.
Zeltinger et al. "Effect of Pore Size and Void Fraction on Cellular Adhesion, Proliferation, and Matrix Deposition." *Tissue Eng.* 7.5(2001):557-572.
Zhang et al. "A Comparative Study of the Antigen-Specific Immune Response Induced by Co-Delivery of CpG Ogn and Antigen Using Fusion Molecules or Biodegradable Microparticles." *J. Pharma. Sci.* 98.12(2007):3283-3292.
Zhao et al. "Active Scaffolds for On-Demand Drug and Cell Delivery." *PNAS.* 108.1(2011):67-72.
Zhao et al. "Directed Cell Migration via Chemoattractants Released from Degradable Microspheres." *Biomat.* 26(2005):5048-5063.
Zhou et al. "Microstructure and Mechanical Properties of Poly(L-lactide) Scaffolds Fabricated by Gelatin Particle Leaching Method." *J. Appl. Polymer Sci.* 98(2005):1373-1379.
Agache et al."Mechanical Properties and Young's Modulus of Human Skin in Vivo." *Arch. Dermatol. Res.* 269.3(1980):221-232.
Aguado et al. "Improving Viability of Stem Cells During Syringe Needle Flow Through the Design of Hydrogel Cell Carriers." *Tissue Eng. Part A.* 18.7-8(2012):806-815.
Akpalo et al. "Fibrin-Polyethylene Oxide Interpenetrating Polymer Networks: New Self-Supported Biomaterials Combining the Properties of Both Protein Gel and Synthetic Polymer." *Acta Biomater.* 7.6(2011):2418-2427.
American Diabetes Association. "Standards of Medical Care in Diabetes—2013." *Diabetes Care.* 36.S1(2013):S11-S66.
Annaidh et al. "Characterization of the Anistropic Mechanical Properties of Excised Human Skin." *J. Mech. Behav. Biomed. Mater.* 5.1(2012):139-148.
*Annual Review Meneki (Immunity).* 2007;2008:122-31.
Aschner et al. "Metabolic Memory for Vascular Disease in Diabetes." *Diabetes Technol. Ther.* 14.S1(2012):S68-S74.
Aubin et al. "Directed 3D Cell Alignment and Elongation in Microengineered Hydrogels." *Biomater.* 31.27(2010):6941-6951.
Babensee et al. "Host Response to Tissue Engineered Device." *Adv. Drug Deli. Rev.* 33.1-2(1998):111-139.
Becker et al. "Cytological Demonstration of the Clonal Nature of Spleen Colonies Derived from Transplanted Mouse Marrow Cells." *Nature.* 197(1963):452-454.
Bégué et al. "Vaccination Against Human Papillomavirus. Implementation and Efficacy Against Cervical Cancer Control." *Bull. Acad. Natl. Med.* 191.9(2007):1805-1816. (French original and English abstract).
Bell. "Models for the Specific Adhesion of Cells to Cells." *Science.* 200.4342(1978):618-627.
Bencherif et al. "Influence of Cross-Linker Chemistry on Release Kinetics of PEG-co-PGA Hydrogels." *J. Biomed. Mater. Res. A.* 90.1(2009):142-153.
Bencherif et al. "End-Group Effects on the Properties of PEG-co-PGA Hydrogels." *Acta Biomater.* 5.6(2009):1872-1883.
Bencherif et al. "Influence of the Degree of Methacrylation of Hyaluronic Acid Hydrogels Properties." *Biomater.* 29.12(2008):1739-1749.
Bencherif et al. "Nanostructured Hybrid Hydrogels Prepared by a Combination of Atom Transfer Radical Polymerization and Free Radical Polymerization." *Biomater.* 30.29(2009):5270-5278.
Bencherif et al. "Synthesis by AFET ATRP of Degradable Nanogel Precursors for in situ Formation of Nanostructured Hyaluronic Acid Hydrogel." *Biomacromol.* 10.9(2009):2499-2507.
Benton et al. "Photocrosslinking of Gelatin Macromers to Synthesize Porous Hydrogels that Promote Valvular Interstitial Cell Function." *Tissue Eng. Part A.* 15.11(2009):3221-3230.
Berg et al. "IL-10 is a Central Regulator of Cyclooxygenase-2 Expression and Prostaglandin Production." *J. Immunol.* 166.4(2001):2674-2680.
Bergstraesser et al. "Stimulation and Inhibition of Human Mammary Epithelial Cell Duct Morphogenesis in vitro." *Proc. Assoc. Am. Physicians.* 108.2(1996):140-154.
Bianco et al. "The Meaning, the Sense and the Significance: Translating the Science of Mesenchymal Stem Cells into Medicine." *Nat. Med.* 19.1(2013):35-42.
Bilodeau. "Regular Pyramid Punch Problem." *J. Appl. Mech.* 59.3(1992):519-523.
Boateng et al. "Wound Healing Dressings and Drug Delivery Systems: A Review." *J. Pharm. Sci.* 97.8(2008):2892-2923.
Boerckel et al. "Mechanical Regulation of Vascular Growth and Tissue Regeneration in vivo." *PNAS.* 108.37(2011):E674-E680.
Brignone et al. "A Phase I Phamacokinetic and Biological Correlative Study of IMP321, a Novel MHC Class II Agonist, in Patients with Advanced Renal Cell Carcinoma." *Clin. Cancer Res.* 15.19(2009):6225-6231.

(56) References Cited

OTHER PUBLICATIONS

Broxmeyer et al. "Insights into the Biology of Cord Blood Stem/Progenitor Cells." *Cell Prolif.* 44.S1(2011):55-59.
Brunner et al. Enhanced dendritic cell maturation by TNF-alpha or cytidine-phosphate-guanosine DNA drives T cell activation in vitro and therapeutic anti-tumor immune responses in vivo. J Immunol. Dec. 1, 2000;165(11):6278-86.
Buckwalter et al. "Form of Antigen Dictates Immunity: Irradiated Cell vs. Whole Cell Lysate Vaccination." *J. Immunol.* 178(2007).
Bullard et al. "Fetal Wound Healing: Current Biology." *World J. Surg.* 27.1(2003):54-61.
Buonaguro et al. "Translating Tumor Antigens into Cancer Vaccines." *Clin. Vaccine Immunol.* 18.1(2011):23-34.
Burdick et al. "Controlled Degradation and Mechanical Behavior of Photopolymerized Hyaluronic Acid Networks." *Biomacromol.* 6.1(2005):386-391.
Burdick et al. "Photoencapsulation of Osteoblasts in Injectable RGD-Modified PEG Hydrogels for Bone Tissue Engineering." *Biomater.* 23.22(2002):4315-4323.
Bürger et al. "Effect of VEGF and its Receptor Antagonist SU-5416, an Inhibitor of Angiogenesis, on Processing of the β-amyloid Precursor Protein in Primary Neuronal Cells Derived From Brain Tissue of Tg2576 Mice." *Int. J. Dev. Neurosci.* 28.7(2010):597-604.
Cameron et al. "The Influence of Substrate Creep on Mesenchymal Stem Cell Behaviour and Phenotype." *Biomater.* 32.26(2011):5979-5993.
Caulfield et al. "Regulation of Major Histocompatibility Complex Class II Antigens on Human Alveolar Macrophages by Granulocyte-Macrophage Colony-Stimulating Factor in the Presence of Glucocorticoids." *Immunol.* 98.1(1999):104-110.
Ceriello et al. "Clinical Review 2: The 'Metabolic Memory': Is more than just Tight Glucose Control Necessary to Prevent Diabetic Complications?" *J. Clin. Endocrinol. Metab.* 94.2(2009):410-415.
Ceriello et al. "The Emerging Challenge in Diabetes: The 'Metabolic Memory.'" *Vascular Pharmacol.* 57.56(2012):133-138.
Chan et al. "Traction Dynamics of Filopodia on Compliant Substrates." *Science.* 322.5908(2008):1687-1691.
Chang. "Mouse Models for Studies of Retinal Degeneration and Diseases." *Methods Mol. Biol.* 935(2013):27-39.
Chen et al. "Functional Human Vascular Network Generated in Photocrosslinkable Gelatin Methacrylate Hydrogels." *Adv. Funct. Mater.* 22.10(2012):2027-2039.
Chiang et al. "Whole Tumor Antigen Vaccines." *Semin. Immunol.* 22.3(2010):132-143.
Clark et al. "Myosin II and Mechanotransduction: A Balancing Act." *Trends Cell Biol.* 17.4(2007):178-186.
Cook et al. "A Sialomucopeptide Liberated by Trypsin from the Human Erythrocyte." *Nature.* 188(1960):1011-1012.
Cooper, "Metabolic Memory: Implications for Diabetic Vascular Complications." *Pediatr. Diabetes.* 10.5(2009):343-346.
Corcione et al. "CCL19 and CXCL12 trigger in vitro chemotaxis of human mantle cell lymphoma B cells." *Clin CancerRes.* Feb. 1, 2004;10(3):964-71.
Cuda et al. "In Vitro Actin Filament Sliding Velocities Produced by Mixtures of Different Types of Myosin." *Biophys. J.* 72.4(1997):1767-1779.
Cukierman et al. "Taking Cell-Matrix Adhesions to the Third Dimension." *Science.* 294.5547(2001):1708-1712.
David et al. "The in vitro Desensitization of Sensitive Cells by Trypsin." *J. Exp. Med.* 120(1964):1189-1200.
Davies et al. "Antibody-Antigen Complexes." *Annu. Rev. Biochem.* 59(1990):439-473.
De Jong et al. "Regulation of Notch Signaling Genes During BMP2-Induced Differentiation of Osteoblast Precursor Cells." *Biochem. Biophys. Res. Commun.*320(2004):100-107.
Dembo et al. "Stresses at the Cell-to-Substrate Interface During Locomotion of Fibroblasts." *Biophys. J.* 76.4(1999):2307-2316.
Dexter et al. "Conditions Controlling the Proliferation of Haemopoietic Stem Cells in Vitro." *J. Cell. Physiol.* 91.3(1977):335-344.
Di Nicola et al. "Human Bone Marrow Stromal Cells Suppress T-Lymphocyte Proliferation Induced by Cellular or Nonspecific Mitogenic Stimuli." *Blood.* 99.10(2002):3838-3843.
Diduch et al. "Two Cell Lines from Bone Marrow tht Differ in Terms of Collagen Synthesis, Osteogenic Characteristics, and Matrix Mineralization." *J. Bone Joint Surg. Am.* 75.1(1993):92-105.
Diridollou et al. "Skin Ageing: Changes of Physical Properties of Human Skin in vivo." *J. Cosmet. Sci.* 23.6(2001):353-362.
Discher et al. "Tissue Cells Feel and Respond to the Stiffness of their Substrate." *Science.* 310.5751(2005):1139-1143.
Disis et al. "Granulocyte-Macrophage Colony-Stimulating Factor: An Effective Adjuvant for Protein and Peptide-Based Vaccines." *Blood.* 88.1(1996):202-210.
Donati et al. "New Hypothesis on the Role of Alternating Sequences in Calcium-Alginate Gels." *Biomacromol.* 6.2(2005):1031-1040.
Douay et al. "Ex vivo Production of Human Red Blood Cells from Hematopoietic Stem Cells: What is the Future in Transfusion?" *Transfus. Med. Rev.* 21.2(2007):91-100.
Dranoff. "GM-CSF-Based Cancer Vaccines." *Immunol. Rev.* 188(2002):147-154.
DuFort et al. "Balancing Forces: Architectural Control of Mechanotransduction." *Nat. Rev. Mol. Cell Biol.* 12.5(2011):308-319.
Dupont et al. "Role of YAP/TAZ in Mechanotransduction." *Nature.* 474.7350(2011):179-183.
Edwards et al. "Evaluation of Biomechanical Properties of Human Skin." *Clin. Dermatol.* 13.4(1995):375-380.
Eming et al. "Inflammation in Wound Repair: Molecular and Cellular Mechanisms." *J. Invest. Dermatol.* 127.3(2007):514-525.
Engler et al. "Microtissue Elasticity: Measurements by Atomic Force Microscopy and its Influence on Cell Differentiation." *Methods Cell. Biol.* 83(2007):521-545.
Engler et al. "Substrate Compliance Versus Ligand Density in Cell on Gel Response." *Biophys. J.* 86.1Pt1(2004):617-628.
Exposito et al. "The Fibrallar Collagen Family." *Int. J. Mol. Sci.* 11.2(2010):407-426.
Falanga. "Wound Healing and its Impairment in the Diabetic Foot." *Lancet.* 366.9498(2005):1736-1743.
Fauquemberque et al. "HLA-A*0201-Restricted CEA-Derived Peptide CAP1 is not a Suitable Target for T-Cell-Based Immunotherapy." *J. Immunother.* 33.4(2010):402-413.
Fisher et al. "The Study of Protein Mechanics with the Atomic Force Microscope." *Trends Biochem. Sci.* 24.10(1999):379-384.
Fransen et al. "Local immunomodulation for cancer therapy: Providing treatment where needed." *Oncoimmunology.* Nov. 1, 2013;2(11):e26493.
Friedenstein et al. "Fibroblast Precursors in Normal and Irradiated Mouse Hematopoietic Organs." *Exp. Hematol.* 4.5(1976):267-274.
Gardel et al. "Traction Stress in Focal Adhesions Correlates Biphasically with Actin Retrograde Flow Speed." *J. Cell Biol.* 183.6(2008):999-1005.
Gasic et al. "Removal and Regeneration of the Cell Coating in Tumour Cells." *Nature.* 196(1962):170.
Gauthier et al. "Temporary Increase in Plasma Membrane Tension Coordinates the Activation of Exocytosis and Contraction During Cell Spreading." *PNAS.* 108.35(2011):14467-14472.
Geerligs et al. "Linear Viscoelastic Behavior of Subcutaneous Adipose Tissue." *Biorheol.* 45.6(2008):677-688.
GenBank Accession No. AAA36738.1, Aug. 3, 1993.
GenBank Accession No. AAA60022.1, Jan. 7, 1995.
GenBank Accession No. AAA64239.1, Mar. 23, 1995.
GenBank Accession No. AAB18786.3, Jul. 12, 1999.
GenBank Accession No. AAH94877.1, May 20, 2005.
GenBank Accession No. AE022039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01955.1, Nov. 14, 2006.
GenBank Accession No. D0103757.1, Jul. 25, 2005.
GenBank Accession No. JN602184.1, Sep. 17, 2011.

(56) References Cited

OTHER PUBLICATIONS

GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000572.2, May 18, 2014.
GenBank Accession No. NM_000638.3, May 4, 2014.
GenBank Accession No. NM_000758.3, May 4, 2014.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001845.4, May 3, 2014.
GenBank Accession No. NM_001901.2, May 18, 2014.
GenBank Accession No. NM_002421.3, May 11, 2014.
GenBank Accession No. NM_002982.3, May 3, 2014.
GenBank Accession No. NM_003377.4, May 5, 2014.
GenBank Accession No. NM_003392.4, May 5, 2014.
GenBank Accession No. NM_004469.4, May 25, 2014.
GenBank Accession No. NM_005429.3, Mar. 31, 2014.
GenBank Accession No. NM_015719.3, Feb. 26, 2014.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001836.2, May 3, 2014.
GenBank Accession No. NP_001892.1, May 18, 2014.
GenBank Accession No. NP_002973.1, May 3, 2014.
GenBank Accession No. NP_003239.2, Feb. 18, 2014.
GenBank Accession No. NP_003368.1, May 5, 2014.
GenBank Accession No. NP_003383.2, May 5, 2014.
GenBank Accession No. NP_004460.1, May 25, 2014.
GenBank Accession No. NP_005420.1, May 11, 2014.
GenBank Accession No. NP_056534.2, Feb. 26, 2014.
GenBank Accession No. U76381.2, Jul. 12, 1999.
Genes et al. "Effect of Substrate Mechanics on Chondrocyte Adhesion to Modified Alginate Surfaces." *Arch. Biochem. Biophys.* 422.2(2004):161-167.
Graessley. "Entangled Linear, Branched and Network Polymer Systems - Molecular Theories." *Adv. Poly. Sci.* 47(1982):67-117.
Guillaume et al. "Two Abundant Proteasome Subtypes that Uniquely Process Some Antigens Presented by HLA Class I Molecules." *PNAS.* 107.43(2010):18599-18604.
Guo et al. "Droplet Microfluidics for High-Throughput Biological Assays." *Lab Chip.* 12.12(2012):2146-2155.
Gurkan et al. "The Mechanical Environment of Bone Marrow: A Review." *Ann. Biomed. Eng.* 36.12(2008):1978-1991.
Halim et al. "Biologic and Synthetic Skin Substitutes: An Overview." *Indian J. Plast. Surg.* 43(2010):S23-S28.
Harris. "Classification, Diagnostic Criteria, and Screening for Diabetes." *Diabetes in America.* NIH Publication No. 95-1468. Chapter 2. (1995):15-36.
Holland et al. "Transforming Growth Factor-β1 Release from Oligo(poly(ethylene glycol) Fumarate) Hydrogels in Conditions that Model the Cartilage Wound Healing Environment." *J. Control. Release.* 94(2004):101-114.
Humphries et al. "Integrin Ligands ata Glance." *J. Cell. Sci.* 119.Pt19(2006):3901-3903.
Huston et al. "Protein Engineering of Antibody Binding Sites: Recovery of Specific Activity in an Anti-Digoxin Single-Chain Fv Analogue Produced in *Escherichia coli*." *PNAS.* 85.16(1988):5879-5883.
Hutson et al. "Synthesis and Characterization of Tunable Poly(Ethylene Glycol): Gelatin Methacrylate Composite Hydrogels." *Tissue Eng. Part A.* 17.13-14(2011):1713-1723.
Ihnat et al. "Hypothesis: the 'Metabolic Memory', the New Challenge of Diabetes." *Diabet. Med.* 24.6(2007)582-586.

Isern et al. "Self-Renewing Human Bone Marrow Mesenspheres Promote Hematopoietic Stem Cell Expansion." *Cell Rep.* 3.5(2013):1714-1724.
Janmey et al. "From Tissue Mechanics to Transcription Factors." *Differentiation.* 86.3(2013):112-120.
Jiang et al. "Two-Piconewton Slip Bond Between Fibronectin and the Cytoskeleton Depends on Talin." *Nature.* 424.6946(2003):334-337.
Jokinen et al. "Integrin-Mediated Cell Adhesion to Type I Collagen Fibrils." *J. Biol. Chem.* 279.30(2004):31956-31963.
Jugdutt et al. "Aging and Defective Healing, Adverse Remodeling, and Blunted Post-Conditioning in the Reperfused Wounded Heart." *J. Am. Coll. Cardiol.* 51.14(2008):1399-1403.
Kang et al. "Effect of Porous Structure on the Degradation of Freeze-Dried Gelatin Hydrogels." *J. Bioact. Compat. Poly.* 14.4(1999):331-343.
Katayama et al. "Integrated Analysis of the Genome and the Transcriptome by FANTOM." *Brief Bioinform.* 5.3(2004):249-258.
Kearney et al. "Macroscale Delivery Systems for Molecular and Cellular Payloads." *Nat. Mater.* 12.11(2013):1004-10017.
Kennedy et al. "Rapid and Extensive Collapse from Electrically Responsive Macroporous Hydrogels." *Adv. Healthc. Mater.* 3.4(2014):500-507.
Khetan et al. "Degradation-Mediated Cellular Traction Directs Stem Cell Fate in Covalently Crosslinked Three-Dimensional Hydrogels." *Nat. Mater.* 12.5(2013):458-465.
Klein et al. "Cell-Cycle Control by Physiological Matrix Elasticity and in Vivo Tissue Stiffening." *Curr. Biol.* 19.18(2009):1511-1518.
Kohane. "Microparticles and Nanoparticles for Drug Delivery." *Biotechnol. Bioeng.* 96.2(2007):203-209.
Kong et al. "FRET Measurements of Cell-Traction Forces and Nano-Scale Clustering of Adhesion Ligands Varied by Substrate Stiffness." *PNAS.* 102.12(2005):4300-4305.
Kratky et al. "Direct Activation of Antigen-Presenting Cells is Required for CD8* T-Cell Priming and Tumor Vaccination." *PNAS.* 108.42(2011):17414-17419.
Kuwahara et al. "Cell Delivery Using an Injectable and Adhesive Transglutaminase-Gelatin Gel." *Tissue Eng. Part C Methods.* 16.4(2010):609-618.
Latorre et al. "Applications of magnetic nanoparticles in medicine: magnetic fluid hyperthermia." *P R Health Sci J.* Sep. 2009;28(3):227-38.
Lee et al. "Intravenous hMSCs Improve Myocardial Infarction in Mice because Cells Embolized in Lung are Activated to Secrete the Anti-Inflammatory Protein TSG-6." *Cell Stem Cell.* 5.1(2009):54-63.
Lele et al. "Investigating Complexity of Protein-Protein Interactions in Focal Adhesions." *Biochem. Biophys. Res. Commun.* 369.3(2008):929-934.
Levental et al. "Soft Biological Materials and their Impact on Cell Function." *Soft Matter.* 3(2007):299-306.
Li et al. "A Novel Cyclohexene Derivate, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." *Mol. Pharmacol.* 69.4(2006):1288-1295.
Li et al. "Purified Hybrid Cells from Dendritic Cell and Tumor Cell Fusions are Superior Activators of Antitumor Immunity." *Cancer Immunol. Immunother.* 50.9(2001):456-462.
Lin et al. "Transdermal Regulation of Vascular Network Bioengineering Using a Photopolymerizable Methacrylated Gelatin Hydrogel." *Biomater.* 34.28(2013):6785-6796.
Liu et al. "Heterobifunctional Poly(Ethylene Glycol)—Tethered Bone Morphogenetic Protein-2-Stimulated Bone Marrow Mesenchymal Stromal Cell Differentiation and Osteogenesis." *Tissue Eng.* 13.5(2007):1113-1124.
Liu et al. "On the Viscoelastic Character of Liver Tissue: Experiments and Modelling of the Linear Behaviour." *Biorheol.* 37.3(2000):191-201.
Liu et al. Immunostimulatory CpG oligodeoxynucleotides enhance the immune response to vaccine strategies involving granulocyte-macrophage colony-stimulating factor. Blood. Nov. 15, 1998;92(10):3730-6.

(56) References Cited

OTHER PUBLICATIONS

Lo et al. "Cell Movement is Guided by the Rigidity of the Substrate." *Biophys. J.* 79.1(2000):144-152.
Lodish et al. "Collagen: The Fibrous Proteins of the Matrix." *Molecular Cell Biology.* eds. New York: W.H. Freeman. Section 22.3(2000):979-985.
Ludewig et al. "Immunotherapy with Dendritic Cells Directed Against Tumor Antigens Shared with Normal Host Cells Results in Severe Autoimmune Disease." *J. Exp. Med.* 191.5(2000):795-804.
Majeti et al. "Identification of a Hierarchy of Multipotent Hematopoietic Progenitors in Human Cord Blood." *Cell Stem Cell.* 1.6(2007):635-645.
Malhotra et al. "Use of an oncolytic virus secreting GM-CSF as combined oncolytic and immunotherapy for treatment of colorectal and hepatic adenocarcinomas." *Surgery.* Apr. 2007;141(4):520-9.
Malmqvist. "Biospecific Interaction Analysis Using Biosensor Technology." *Nature.* 361.6408(1993):186-187.
Mammoto. "Mechanical Control of Tissue and Organ Development." *Development.* 37.9(2010):1407-1420.
Manavski et al. "Vascular Niche Controls Organ Regeneration." *Circ. Res.* 114.17(2014):1077-1079.
Mansoor et al. "Engineering T Cells for Cancer Therapy." *Br. J. Cancer.* 93.10(2005):1085-1091.
Masedunskas et al. "Role for the Actomyosin Complex in Regulated Exocytosis Revealed by Intravital Microscopy." *PNAS.* 108.33(2011):13552-13557.
McDonald et al. "Early Fracture Callus Displays a Smooth Muscle-Like Viscoelastic Properties Ex Vivo: Implications for Fracture Healing." *J. Orthop. Res.* 27.11(2009):1508-1513.
McKinnon et al. "Biophysically Defined and Cytocompatible Covalently Adaptable Networks as Viscoelastic 3D Cell Culture Systems." *Adv. Mater.* 26.6(2014):865-872.
McWhorter et al. "Modulation of Macrophage Phenotype by Cell Shape." *PNAS.* 110.43(2013):17253-17258.
Melief et al. "Immunotherapy of Established (Pre)Malignant Disease by Synthetic Long Peptide Vaccines." *Nat. Rev. Cancer.* 8(2008):351-360.
Merkel et al. "Using Mechanobiological Mimicry of Red Blood Cells to Extend Circulation Times of Hydrogel Microparticles." *PNAS.* 108.2(2011):586-591.
Metters et al. "Fundamental Studies of Biodegradable Hydrogels as Cartilage Replacement Materials." *Biomed. Sci. Instrum.* 35(1999):33-38.
Miljkovic et al. "Chondrogenesis, Bone Morphogenetic Protein-4 and Mesenchymal Stem Cells." *Osteoarthritis Cartilage.* 16(2008):1121-1130.
Miller et al. "Melanoma." *N. Engl. J. Med.* 355.1(2006):51-65.
Miralles et al. "Actin Dynamics Control SRF Activity by Regulation of its Coactivator MAL." *Cell.* 113.3(2003):329-342.
Molinari et al. "Modification of Surface Membrane Antigens by Trypsin." *Proc. Soc. Exp. Biol. Med.* 148.4(1975):991-994.
Molloy et al. "Movement and Force Produced by a Single Myosin Head." *Nature.* 378.6553(1995):209-212.
Mooney et al. "Cytoskeletal Filament Assembly and the Control of Cell Spreading and Function by Extracellular Matrix." *J. Cell Sci.* 108.Pt6(1995):2311-2320.
Muralidharan-Chari et al. "ARF6-Regulated Shedding of Tumor Cell-Derived Plasma Membrane Microvesicles." *Curr. Biol.* 19.22(2009):1875-1885.
NCBI Accession No. NM_001561.5, Mar. 16, 2014.
NCBI Accession No. NM_004448.3, Apr. 23, 2014.
NCBI Accession No. NM_005018.2, Apr. 27, 2014.
NCBI Accession No. NM_181780.3, Jan. 27, 2014.
NCBI Accession No. NP_001193, May 3, 2014.
NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_005009.2, Apr. 27, 2014.
NCBI Accession No. NP_861445.3, Jan. 27, 2014.
Nestle et al. "Vaccination of melanoma patients with peptide- or tumor lysate-pulsed dendritic cells." *Nat Med.* Mar. 1998;4(3):328-32.
Nichol et al. "Cell-Laden Microengineered Gelatin Methacrylate Hydrogels." *Biomater.* 31.21(2010):5536-5544.
Niessen et al. "The $\alpha 6\beta 4$ Integrin is a Receptor for Both Lamin and Kalinin." *Exp. Cell Res.* 211.2(1994):360-367.
Osunkoya et al. "Synthesis and Fate of Immunological Surface Receptors on Cultured Burkitt Lymphoma Cells." *Int. J. Cancer.* 4.2(1969):159-165.
Page-McCaw et al. "Matrix Metalloproteinases and the Regulation of Tissue Remodelling." *Nat. Rev. Mol. Cell Biol.* 8.3(2007):221-233.
Pailler-Mattei et al. "In vivo Measurements of the Elastic Mechanical Properties of Human Skin by Indentation Tests." *Med. Eng. Phys.* 30.5(2008):599-606.
Pardoll. "The Blockade of Immune Checkpoints in Cancer Immunotherapy." *Nat. Rev. Cancer.* 12.4(2012):252-264.
Parekh et al. "Modulus-Driven Differentiation of Marrow Stromal Cells in 3D Scaffolds that is Independent of Myosin-Based Cytoskeletal Tension." *Biomater.* 32.9(2011):2256-2264.
Parekkadan et al. "Mesenchymal Stem Cell-Derived Molecules Reverse Fulminant Hepatic Failure." *PLoS One.* 2.9(2007):e941.
Park et al. "Photopolymerized Hyaluronic Acid-Based Hydrogels and Interpenetrating Networks." *Biomater.* 24.6(2003):893-900.
Pawlaczyk et al. "Age-Dependent Biomechanical Properties of the Skin." *Postepy. Dermatol. Alergol.* 30.5(2013):302-306.
Pek et al. "The Effect of Matrix Stiffness on Mesenchymal Stem Cell Differentiation in a 3D Thixotropic Gel." *Biomater.* 31.3(2010):385-391.
Pena et al. "Effects of TGF-$\beta$ and TGF-$\beta$ Neutralizing Antibodies on Fibroblast-Induced Collagen Gel Contraction: Implications for Proliferative Vitroretinpathy." *Invest. Ophthalmol. Vis. Sci.* 35.6(1994):2804-2808.
Peyton et al. "The Use of Poly(ethylene glycol) Hydrogels to Investigate the Impact of ECM Chemistry and Mechanics on Smooth Muscle Cells." *Biomater.* 27.28(2006):4881-4893.
Pinho et al. "PDGFR$\alpha$ and CD51 Mark Human Nestin+ Sphere-Forming Mesenchymal Stem Cells Capable of Hematopoietic Progenitor Cell Expansion." *J. Exp. Med.* 210.7(2013):1351-1367.
Qi et al. "Patterned Differentiation of Individual Embryoid Bodies in Spatially Organized 3D Hybrid Microgels." *Adv. Mater.* 22.46(2010):5276-5281.
Qin et al. "Soft Lithography for Micro- and Nanoscale Patterning." *Nat. Protoc.* 5.3(2010):491-502.
Raeber et al. "Molecularly Engineered PEG Hydrogels: A Novel Model System for Proteolyrically Mediated Cell Migration." *Biophys. J.* 89.2(2005):1374-1388.
Ramón-Azcón et al. "Gelatin Methacrylate as a Promising Hydrogel for 3D Microscale Organization and Proliferation of Dielectroretically Patterned Cells." *Lab on a Chip.* 12.16(2012):2959-2969.
Ranganath et al. "Harnessing the Mesenchymal Stem Cell Secretome for the Treatment of Cardiovascular Disease." *Cell Stem Cell.* 10.3(2012):244-258.
Raposo et al. "Extracellular Vesicles: Exosomes, Microvesicles, and Friends." *J. Cell. Biol.* 200.4(2013):373-383.
Roccaro et al. "BM Mesenchymal Stromal Cell-Derived Exosomes Facilitate Multiple Myeloma Progression." *J. Clin. Invest.* 123.4(2013):1542-1555.
Rodriguez et al. "Minimal "Self" Peptides that Inhibit Phagocytic Clearance and Enhance Delivery of Nanoparticles." *Science.* 339.6122(2013):971-975.
Sacchetti et al. "Self-Renewing Osteoprogenitors in Bone Marrow Sinusoids can Organize a Hematopoietic Microenvironment." *Cell.* 131.2(2007):324-336.
Sakai et al. "An Injectable, in situ Enzymatically Gellable, Gelatin Derivative for Drug Delivery and Tissue Engineering." *Biomater.* 30.20(2009):3371-3377.
Sato, "Human dendritic cells." *Biotherapy.* Nov. 2004;18(6):467-77.
Schofield. "The Relationship Between the Spleen Colony-Forming Cell and the Haemopoietic Stem Cell." *Blood. Cells.* 4.1-2(1978):7-25.

(56) References Cited

OTHER PUBLICATIONS

Schwartz. "Integrins and Extracellular Matrix in Mechanotransduction." *Cold Spring Harb. Perspect. Biol.* 2.12(2010):a005066.
Sensi et al. "Unique Tumor Antigens: Evidence for Immune Control of Genome Integrity and Immunogenic Targets for T Cell-Mediated Patient-Specific Immunotherapy." *Clin. Cancer Res.* 12.17(2006):5023-5032.
Shi et al. "Granulocyte-Macrophage Colony-Stimulating Factor (GM-CSF) and T-Cell Responses: What we do and don't know." *Cell Res.* 16.2(2006):126-133.
Shin et al. "Contractile Forces Sustain and Polarize Hematopoiesis from Stem and Progenitor Cells." *Cell Stem Cell.* 14.1(2014):81-93.
Shin et al. "Lamins Regulate Cell Trafficking and Lineage Maturation of Adult Human Hematopoetic Cells." *PNAS.* 110.47(2013):18892-18897.
Shin et al. "Myonsin-II Inhibition and Soft 2D Matrix Maximize Multinucleation and Cellular Projections Typical of Platelet-Producing Megakaryocytes." *PNAS.* 108.28(2011):11458-11463.
Siegwart et al. "Synthesis, Characterization, and in vitro Cell Culture Viability of Degradable Poly(N-isopropylacrylamide-co-5,6-benzo-2-methylene-1,3-dioxepane)-Based Polymers and Cross-linked Gels." *J. Biomed. Mater. Res. A.* 87.2(2008):345-358.
Silva et al. "Effects of VEGF Temporal and Spatial Presentation on Angiogenesis." *Biomaterials.* 31.6(2010):1235-1241.
Singer et al. "Cutaneous Wound Healing." *N. Engl. J. Med.* 341.10(1999):738-746.
Solon et al. "Fibroblast Adaptation and Stiffness Matching to Soft Elastic Substrates." *Biophys. J.* 93.12(2007):4453-4461.
Stachowiak et al. "Inverse Opal Hydrogel-Collagen Composite Scaffolds as a Supportive Microenvironment for Immune Cell Migration." *J. Biomed. Mater. Res.* 85A(2008):815-828.
Sun et al. "Biomimetic Interpenetrating Polymer Network Hydrogels Based on Methacrylated Alginate and Collagen for 3D Pre-Osteoblast Spreading and Osteogenic Differentiation." *Soft Matter.* 8(2012):2398-2404.
Sun et al. "Highly Stretchable and Tough Hydrogels." *Nature.* 489.7414(2012):133-136.
Suri et al. "Photopatterned Collagen-Hyaluronic Acid Interpenetrating Polymer Network Hydrogels." *Acta Biomater.* 5.7(2009):2385-2397.
Swift et al. "Nuclear Lamin-A Scales with Tissue Stiffness and Enhances Matrix-Directed Differentiation." *Science.* 341.6149(2013):1240104.
Syed et al. "Stem Cell Therapy Market." *Nat. Rev. Drug Discov.* 12.3(2013):185-186.
Tabata et al. "Enhanced Vascularization and Tissue Granulation by Basic Fibroblast Growth Factor Impregnated in Gelatin Hydrogels." *J. Control. Release.* 31.2(1994):189-199.
Tannous. "*Gaussia* Luciferase Reporter Assay for Monitoring Biological Processes in Culture and in vivo." *Nat. Protoc.* 4.4(2009):582-591.
Thomas et al. "Intravenous Infusion of Bone Marrow in Patients Receiving Radiation and Chemotherapy." *N. Engl. J. Med.* 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." *J. Exp. Med.* 190.11(1999):1669-1678.
Tong et al. "Engineering Interpenetrating Network Hydrogels as Biomimetic Cell Niche with Independently Tunable Biochemical and Mechanical Properties." *Biomater.* 35.6(2014):1807-1815.
Trappmann et al. "Extracelluar-Matrix Tethering Regulates Stem-Cell Fate." *Nat. Mater.* 11.7(2012):642-649.
Trappmann et al. "How Cells Sense Extracellular Matrix Stiffness: A Material's Perspective." *Curr. Opin. Biotechnol.* 24.5(2013):948-953.
Uhlenbruck. "Action of Proteolytic Enzymes on the Human Erythrocyte Surface." *Nature.* 190(1961):181.
Ulrich et al. "Probing Cellular Mechanobiology in Three-Dimensional Culture with Collagen-Agarose Matrices." *Biomater.* 31.7(2010):1875-1884.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Van der Bruggen et al. "T Cell-Defined Tumor Antigens." *Cancer Immunity.* (2013). Http:www.cancerimmunity.org/peptide.
Venturoni et al. "Investigations into the Polymorphism of Rat Tail Tendon Fibrils Using Atomic Force Microscopy." *Biochem. Biophys. Res. Commun.* 303.2(2003):508-513.
Vincent et al. "Stem Cell Differentiation: Post-Degradation Forces Kick in." *Nat. Mater.* 12.5(2013):384-386.
Vogel et al. "Local Force and Geometry Sensing Regulate Cell Functions." *Nat. Rev. Mol. Cell Biol.* 7.4(2006):265-275.
Wang et al. "Mechanotransduction at a Distance: Mechanically Coupling the Extracellular Matric with the Nucleus." *Nat. Rev. Mol. Cell. Biol.* 10.1(2009):75-82.
Wang et al. "Photothermal effects of supramolecularly assembled gold nanoparticles for the targeted treatment of cancer cells." *Angew Chem Int Ed Engl.* May 17, 2010;49(22):3777-81.
Wang-Gillam et al. "A Phase I Study of IMP321 and Gemcitabine as the Front-Line Therapy in Patients with Advanced Pancreatic Adenocarcinoma." *Invest. New Drugs.* 31.3(2013):707-713.
Warner et al. "Cyclooxygenases: New Forms, New Inhibitors, and Lessons from the Clinic." *FASEB J.* 18.7(2004):790-804.
Weisenberger et al. "Comprehensive DNA Methylation Analysis on the Illumina® Infinium® Assay Platform." Illumina, Inc. Mar. 25, 2008. Web.
Weiss et al. "The Demonstration of Rupture of Cell Surfaces by an Immunological Technique." *Exp. Cell Res.* 30(1963):331-338.
Wen et al. "Mechanically Robust Gelatin-Alginate IPN Hydrogels by a Combination of Enzymatic and Ionic Crosslinking Approaches." *Macromol. Mater. Eng.* 299(2013):504-513.
Wieland et al. "Engineering Molecular Circuits Using Synthetic Biology in Mammalian Cells." *Annu. Rev. Chem. Biomol. Eng.* 3(2012):209-234.
Wipff et al. "Myofibroblast Contraction Activates Latent TGF-β1 from the Extracellular Matrix." *J. Cell Biol.* 179.6(2007):1311-1323.
Wong et al. "Focal Adhesion Kinase Links Mechanical Force to Skin Fibrosis via Inflammatory Signaling." *Nat. Med.* 18.1(2011):148-152.
Wong et al. "Mechanical Force Prolongs Acute Inflammation via T-Cell-Dependent Pathways During Scar Formation." *FASEB. J.* 25.12(2011):4498-4510.
Wong et al. "Pushing Back: Wound Mechanotransduction in Repair and Regeneration." *J. Invest. Dermatol.* 131.11(2011):2186-2196.
Wozniak et al. "Mechanotransduction in Development: A Growing Role for Contractility." *Nat. Rev. Mol. Cell Biol.* 10.1(2009):34-43.
Yamazaki et al., *J. Immunology.* 181:6923-6933 (2008).

(56) References Cited

OTHER PUBLICATIONS

Yang et al., "The effect of incorporating RGD adhesive peptide in polyethylene glycol diacrylate hydrogel on osteogenesis of bone marrow stromal cells." *Biomaterials*. 26(2005):5991-5998.

Yeung et al. "Effects of Substrate Stiffness on Cell Morphology, Cytoskeletal Structure, and Adhesion." *Cell Motil. Cytoskeleton*. 60.1(2005):24-34.

Yoo et al. "Bio-Inspired, Bioengineered and Biomimetic Drug Delivery Carriers." *Nat. Rev. Drug Discov*. 10.7(2011):521-535.

Yoon. "Hidden Markov Models and their Applications in Biological Sequene Analysis." *Curr. Genomics*. 10.6(2009):402-415.

Young et al. "Gelatin as a Delivery Vehicle for the Controlled Release of Bioactive Molecules." *J. Control. Release*. 109.1-3(2005):256-274.

Zemel et al. "Optimal Matrix Rigidity for Stress Fibre Polarization in Stem Cells." *Nat. Phys*. 6.6(2010):468-473.

Zhang et al. "A Tension-Induced Mechanostransduction Pathway Promotes Epithelial Morphogenesis." *Nature*. 471.7336(2011):99-103.

Zhang et al. "Talin Depletion Reveals Independence of Initial Cell Spreading from Integrin Activation and Traction." *Nat. Cell Biol*. 10.9(2008):1062-1068.

Zhao et al. "Stress-Relaxation Behavior in Gels with Ionic and Covalent Crosslinks." *J. Appl. Phys*. 107.6(2010):63509.

Bencherif et al., "Injectable preformed scaffolds with shape-memory properties," *PNAS*, (2012) vol. 109, No. 48, pp. 19590-19595.

Lee et al., Controlling Mechanical and Swelling Properties of Alginate Hydrogels Independently by Cross-Linker Type and Cross-Linking Density. Macromolecules. 2000;33(11):4291-4.

Pajonk et al., From sol-gel to aerogels and cryogels. Journal of Non-Crystalline Solids. 1990;121(1-3):66-67.

Research Results of National Institute of Advanced Industrial Science and Technology, 2006, URL: [http://www.aist.go.jp/aist_j/press_release/pr2006/pr20060719. html].

Thornton et al., Shape retaining injectable hydrogels for minimally invasive bulking. J Urol. Aug. 2004;172(2):763-8.

\* cited by examiner

SEQUENCE LISTING

```
<160> NUMBER OF SEQ ID NOS: 2

<210> SEQ ID NO 1
<211> LENGTH: 128
<212> TYPE: PRT
<213> ORGANISM: Homo sapiens

<400> SEQUENCE: 1

Met Ala Pro Ala Arg Ser Pro Ser Pro Ser Thr Gln Pro Trp Glu His
1               5                   10                  15

Val Asn Ala Ile Gln Glu Ala Arg Arg Leu Leu Asn Leu Ser Arg Asp
            20                  25                  30
```

```
Thr Ala Ala Glu Met Asn Glu Thr Val Glu Val Ile Ser Glu Met Phe
        35                  40                  45

Asp Leu Gln Glu Pro Thr Cys Leu Gln Thr Arg Leu Glu Leu Tyr Lys
    50                  55                  60

Gln Gly Leu Arg Gly Ser Leu Thr Lys Leu Lys Gly Pro Leu Thr Met
65                      70                  75                  80

Met Ala Ser His Tyr Lys Gln His Cys Pro Pro Thr Pro Glu Thr Ser
                85                  90                  95

Cys Ala Thr Gln Ile Ile Thr Phe Glu Ser Phe Lys Glu Asn Leu Lys
            100                 105                 110

Asp Phe Leu Leu Val Ile Pro Phe Asp Cys Trp Glu Pro Val Gln Glu
        115                 120                 125

<210> SEQ ID NO 2
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: ACRL-PEG
<222> LOCATION: (1)..(1)

<400> SEQUENCE: 2

Gly Gly Gly Gly Arg Gly Asp Ala Ser Ser Lys Tyr
1               5                   10
```

INJECTABLE PREFORMED MACROSCOPIC 3-DIMENSIONAL SCAFFOLDS FOR MINIMALLY INVASIVE ADMINISTRATION

RELATED APPLICATIONS

This application is a national stage application, filed under 35 U.S.C. § 371, of International Application No. PCT/US2012/035505 filed Apr. 27, 2012, which claims the benefit of priority under 35 U.S.C. § 119(e) to U.S. Provisional Application No. 61/480,237 filed Apr. 28, 2011, the contents of which are incorporated herein by reference in their entireties.

INCORPORATION-BY-REFERENCE OF SEQUENCE LISTING

The contents of the text file named "29297-084N01US_ST25.txt", which was created on Dec. 20, 2013 and is 2 KB in size, is hereby incorporated by reference in their entirety.

STATEMENT AS TO FEDERALLY SPONSORED RESEARCH

This invention was made with U.S. Government support under Grant Number R01 DE013349 from the National Institutes of Health. The Government has certain rights in the invention.

FIELD OF THE INVENTION

The invention relates to polymer scaffolds for drug and cell delivery systems.

BACKGROUND

Tissue engineering is an approach for regeneration, replacement, and improvement of the functions of damaged tissues by manipulating materials according to the specific structure or function of the desired tissues. Porous and biodegradable polymer scaffolds are utilized as a structural supporting matrix or as a cell adhesive substrate for cell-based tissue engineering. A major side effect of the surgical implantation of three dimensional scaffolds is the trauma created by physicians while treating patient illness. For example, current technologies for the surgical implantation of three dimensional scaffolds involve incisions that lead to patient pain, bleeding, and bruising. As such, there is a pressing need in the art to develop less invasive structured polymer scaffolds.

SUMMARY OF THE INVENTION

The present invention provides compositions and a minimally-invasive method of injecting preformed large macroporous polymer-based hydrogels that are loaded with cargo such as cells and/or therapeutics such as small molecule compounds, proteins/peptides (e.g., antigens to which an immune response is desired), or nucleic acids. Hydrogel (also called aquagel) is a network of polymer chains that are hydrophilic, and are sometimes found as a colloidal gel in which water is the dispersion medium. Hydrogels are highly absorbent (they can contain over 99% water) natural or synthetic polymers that possess a degree of flexibility very similar to natural tissue, due to their significant water content. Unlike conventional hydrogels, a unique characteristic of these cell/scaffold constructs described here is that when an appropriate shear stress is applied, the deformable hydrogel is dramatically and reversibly compressed (up to 90% of its volume) resulting in injectable macroporous preformed scaffolds. This property allows gel/cell constructs to be delivered via syringe with high precision to target sites.

Accordingly, the invention features a cell-compatible highly crosslinked hydrogel polymer composition comprising a high density of open interconnected pores, wherein the hydrogel is characterized by shape memory following deformation by compression or dehydration. The hydrogel comprises polymers that are modified, e.g., sites on the polymer molecule are modified with a methacrylic acid group (methacrylate (MA)) or an acrylic acid group (acrylate). An exemplary modified alginate is MA-alginate (methacrylated alginate). In the case of Methacrylated-alginate, 50% corresponds to the degree of methacrylation of alginate. This means that every other repeat unit contains a methacrylated group. The degree of methacrylation can be varied from 1% to 90%. Above 90%, the chemical modification may reduce solubility of the polymer water-solubility. Polymers can also be modified with acrylated groups instead of methacrylated groups. The product would then be referred to as an acrylated-polymer. The degree of methacrylation (or acrylation) can be varied for most polymers. However, some polymers (e.g. PEG) maintain their water-solubility properties even at 100% chemical modification. After crosslinking, polymers normally reach near complete methacrylate group conversion indicating approximately 100% of cross-linking efficiency. For example, the polymers in the hydrogel are 50-100% crosslinked (covalent bonds). The extent of crosslinking correlates with the durability of the hydrogel. Thus, a high level of crosslinking (90-100%) of the modified polymers is desirable.

For example, the highly crosslinked hydrogel polymer composition is characterized by at least 50% polymer crosslinking (e.g., 75%, 80%, 85%, 90%, 95%, 98%). The high level of crosslinking confers mechanical robustness to the structure. However, the % crosslinking is generally less than 100%. The composition is formed using a free radical polymerization process and a cryogelation process.

The cryogel comprises at least 75% pores, e.g., 80%, 85, 90%, 95%, and up to 99% pores. The pores are interconnected. Interconnectivity is important to the function of the composition, as without interconnectivity, water would become trapped within the gel. Interconnectivity of the pores permits passage of water (and other compositions such as cells and compounds) in and out of the structure. In a fully hydrated state, the composition comprises between 90-99% water. In a compressed or dehydrated hydrogel, up to 50%, 60%, 70% of that water is absent.

In some examples, the composition comprises a cell adhesion composition chemically linked, e.g., covalently attached, to the polymer. For example, the cell adhesion composition comprises a peptide comprising an RGD amino acid sequence.

For cell therapy, the composition comprises a eukaryotic cell in one or more of the open interconnected pores. For example, the eukaryotic cell comprises a live attenuated cancer cell (e.g., irradiated cell acts as cancer antigen). Optionally, the composition comprises a biomolecule in one or more of the open interconnected pores. Biomolecules include small molecule compounds (e.g., less than 1000 daltons in molecular mass), nucleic acids, proteins or fragments thereof, peptides. Exemplary biomolecules include granulocyte macrophage-colony stimulating factore (GM-CSF), large nucleic acid compositions such as plasmid DNA, and smaller nucleic acid compositions such as CpG oligodeoxynucleotide (CpG-ODN).

Preferably, the cryogel compositions are injectable through a hollow needle. Upon compression or dehydration, the composition maintains structural integrity and shape memory properties, i.e., after compression or dehydration, the composition regains its shape after it is rehydrated or the shear forces of compression are removed/relieved In one example, the composition comprises an alginate-based hydrogel. Other examples of polymer compositions from which the cryogel is fabricated include hyaluronic acid, gelatin, heparin, dextran, carob gum, PEG, PEG derivatives including PEG-co-PGA and PEG-peptide conjugates. The techniques can be applied to any biocompatible polymers, e.g. collagen, chitosan, carboxymethylcellulose, pullulan, polyvinyl alcohol (PVA), Poly(2-hydroxyethyl methacrylate) (PHEMA), Poly(N-isopropylacrylamide) (PNIPAAm), Poly(acrylic acid) (PAAc), etc. The shape of the cryogel is dictated by a mold and can thus take on any shape desired by the fabricator, e.g., various sizes and shapes (disc, cylinders, squares, strings, etc.) are prepared by cryogenic polymerization. Injectable cryogels can be prepared in the micrometer-scale to millimeter-scale. Volume varies from a few hundred $\mu m^3$ to over 100 $mm^3$. An exemplary scaffold composition is between 1 $mm^3$ and 10 $mm^3$ in size. In another example, the cryogel is defined by volume. For example, the cryogel scaffold composition comprises 25 $\mu l$ in volume in a hydrated state. The gels are hydrated in an aqueous medium. Exemplary cryogel compositions are typically in the range of 10-70 $\mu l$ in volume and may be larger or smaller depending on the use and site to be treated.

The cryogel acts as a sponge. The cryogels are sterilized. In some applications, the cryogels are hydrated, loaded with cells or other compounds (e.g., small molecules and other compounds, nucleic acids, or proteins/peptides) and loaded into a syringe or other delivery apparatus. For example, the syringes are prefilled and refrigerated until use. In another example, the cryogel is dehydrated, e.g., lyophyllized, optionally with a drug or other compound loaded in the gel and stored dry or refrigerated. Prior to administration, the cryogel-loaded syringe or apparatus is contacted with a solution containing cells and/or other compounds to be delivered. For example, the barrel of the cryogel pre-loaded syringe is filled with a physiologically-compatible solution, e.g., phosphate-buffered saline (PBS). In practice, the cryogel is administered to a desired anatomical site followed by the volume of solution, optionally containing other ingredients, e.g., cells or therapeutic compounds. For example, a 25 $\mu l$ cryogel is administered with approximately 200 $\mu l$ of solution. The cryogel is then rehydrated and regains its shape integrity in situ. The volume of PBS or other physiologic solution administered following cryogel placement is generally about 10 times the volume of the cryogel itself.

Also within the invention are methods of using the cryogel compostions. For example, a method for repairing, regenerating, or restructuring a tissue comprises administering to a subject the device/cryogel composition described above. If the cryogel contains cells, the cells retain their viability after passage through the syringe or delivery apparatus, cells proliferate in the device/cryogel, then leave the cryogel composition to function outside of the gel and in the bodily tissues of the recipient subject. For example, the cryogel is administered subcutaneously as a dermal filler, thereby restructuring the tissue, e.g., dermal tissue. In another example, the cryogel device comprises a stem cell and the composition/device is administered to a damaged or diseased tissue of a subject, thereby repairing or regenerating the tissue, e.g., muscle, bone, kidney, liver, heart, bladder, ocular tissue or other anatomic structures.

In another example, the cryogel compositions are used in a method for delivering genetic material, e.g., to deliver plasmid DNA.

In yet another example, a method for eliciting an immune response, is carried out by administering to a subject a cryogel composition as described above that further contains a microbial pathogen or tumor cell to which an immune response is elicited. Such a vaccine composition is administered prophylactically or therapeutically.

Cell viability is minimally affected or unaffected by the shear thinning process, and gel/cell constructs stay fixed at the point of introduction. As such, these gels are useful for the delivery of cells and other compounds to target biological sites in therapeutic methods such as tissue regeneration (cell therapy, drug delivery) efforts.

The invention provides a device comprising an injectable scaffold composition with open, interconnected macropores. Preferably, the scaffold composition is injectable through a hollow needle. For example, the scaffold composition is injectable through a 16-gauge, an 18-gauge, a 20-gauge, a 22-gauge, a 24-gauge, a 26-gauge, a 28-gauge, a 30-gauge, a 32-gauge, or a 34-gauge needle. Upon compression, the scaffold composition maintains shape memory properties. The scaffold composition also maintains structural integrity in that it is flexible (i.e., not brittle) and does not break under sheer pressure. In one aspect, the scaffold composition is an alginate-based hydrogel. The scaffold composition is between 0.01 $mm^3$ and 100 $mm^3$. For example, the scaffold composition is between 1 $mm^3$ and 75 $mm^3$, between 5 $mm^3$ and 50 $mm^3$, between 10 $mm^3$ and 25 $mm^3$. Preferably, the scaffold composition is between 1 $mm^3$ and 10 $mm^3$ in size.

The hydrogel, if to be used to transplant cells, comprises pores to permit the structure to be seeded with cells and to allow the cells to proliferate and migrate out to the structure to relocate to bodily tissues such as the injured or diseased muscle in need of repair or regeneration. For example, cells are seeded at a concentration of about $1 \times 10^4$ to $1 \times 10^7$ cells/ml and are administered dropwise onto a dried hydrogel device. The dose of the gel/device to be delivered to the subject is scaled depending on the magnitude of the injury or diseased area, e.g., one milliliter of gel for a relatively small defect and up to 50 mls of gel for a large wound. Preferable the hydrogel comprises macropores, e.g., pores that are characterized by a diameter of 2 $\mu m$-1 mm. The average pore size comprises 200 $\mu m$. Cells can move into and out of the cryogel via the open interconnected pores as a typical cell comprises a diameter or about 20 $\mu m$. The gel delivery devices are suitable for treatment of human beings, as well as animals such as horses, cats, or dogs.

Preferably, the hydrogel is characterized by shape-memory. The polymer chains of the hydrogel are covalently crosslinked and/or oxidized. Such hydrogels are suitable for minimally-invasive delivery. Prior to delivery into the human body, such a hydrogel is lyophyllized and compressed prior to administration to a subject for the regeneration of muscle tissue. Minimally-invasive delivery is characterized by making only a small incision into the body. For example, the hydrogel is administered to a muscle of a subject using a needle or angiocatheter.

Injectable cryogels have been designed to pass through a hollow structure, e.g., very fine needles, such as 18-30G needles, as a tissue filler for applications in cosmetic surgery, for tissue augmentation, and tissue repair which may be due to injury caused by disease and external trauma. The injectable cryogels may be molded to a desired shape, in the form of rods, square, disc, spheres, cubes, fibers, foams. In some situations, the injectable cryogels can be used as scaffolds for cell incorporation. The formed cryogel is mixed with cells to provide tissue engineered products, or can be used as a bio-matrix to aid tissue repair or tissue augmentation. The incorporated cells can be any mammalian cells (e.g. stem cells, fibroblasts, osteoblasts, chrondrocytes, immune cells, etc).

Injectable cryogels can also be produced in a form in which pharmaceuticals or other bioactive substances (e.g. growth factors, DNA, enzymes, peptides, drugs, etc) are incorporated for controlled drug delivery.

Injectable cryogels may be further functionalized by addition of a functional group chosen from the group consisting of: amino, vinyl, aldehyde, thiol, silane, carboxyl, azide, alkyne. Alternatively, the cryogel may be further functionalized by the addition of a further cross-linker agent (e.g. multiple arms polymers, salts, aldehydes, etc). The solvent may be aqueous, and in particular acidic or alkaline. The aqueous solvent may comprise a water-miscible solvent (e.g. methanol, ethanol, DMF, DMSO, acetone, dioxane, etc).

The cryo-crosslinking takes place in a mold and the injectable cryogels may be degradable. The pore size can be controlled by the selection of the main solvent used, the incorporation of a porogen, the freezing temperature applied, the cross-linking conditions (e.g. polymer concentration), and also the type and molecule weight of the polymer used.

Therapeutic and cosmetic uses are described throughout the specification. Exemplary applications include use as a dermal filler, in drug delivery, as a wound dressing, for post surgical adhesion prevention, and for repair and/or regenerative medical applications such as cell therapy, gene therapy, tissue engineering, immunotherapy.

Biomolecules are purified naturally-occurring, synthetically produced, or recombinant compounds, e.g., polypeptides, nucleic acids, small molecules, or other agents. For example, the compositions include GM-CSF, pathogen-associated molecular patterns (PAMPs) such as CpG-ODN, and tumor antigens or other antigens. The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

DESCRIPTION OF THE DRAWINGS

FIG. 4A is a photograph showing alginate cryogel scaffolds (white) and rhodamine-labeled alginate scaffolds (pink). Bioluminescence B16-F10 cells were seeded on 1% RGD-modified MA-Alginate cryogels at a concentration of 200×10$^3$ cells/scaffold. Luciferase transected melanoma cells were cultured for 6 hr into rhodamine-labeled alginate cryogels before injection into mice. FIG. 4B is a photograph showing optical live imaging to demonstrate that macroporous alginate gels are suitable for homogenous encapsulation and distribution of bioluminescent B16 cells. FIG. 4C is a photograph showing scanning electron microscope (SEM) imaging to demonstrate that macroporous alginate gels are suitable for homogenous encapsulation and distribution of bioluminescent B16 cells. FIG. 4D is a photograph showing live fluorescence imaging of subcutaneous injections of gels. FIG. 4E is a photograph showing live fluorescence imaging of subcutaneous injections of gels at 2 days post-injection. FIG. 4F is a photograph showing live fluorescence imaging of subcutaneous injections of gels at 9 days post-injection. Bioluminescent B16-cells were visualized by live imaging. Arg-Gly-Asp (RGD; cell-adhering peptide)-Alginate scaffolds significantly promoted target delivery of cells compared to unmodified gels. By contrast, injection of free cells (bolus) did not promote localization of cells (bioluminescent signal absent).

DETAILED DESCRIPTION

Figure 1:
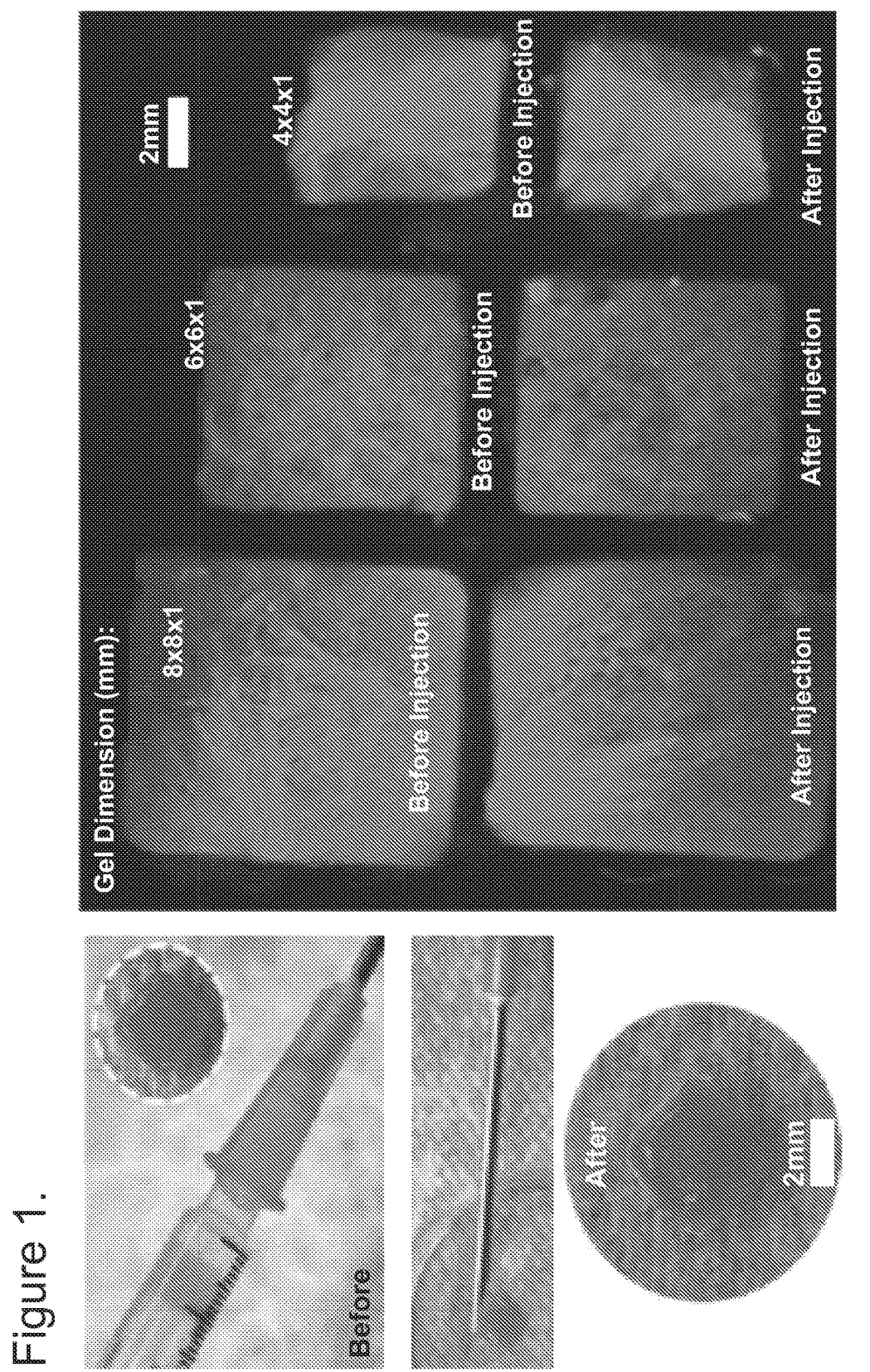
FIG. 1 is a series of photomicrographs showing injectable alginate-based hydrogel systems. Rhodamine-labeled 1% methacrylated (MA)-alginate gels with various sizes and shapes (disc, cylinders, squares, etc.) were prepared by cryogenic polymerization. Square shape injectable scaffolds are shown. Fluorescent macroscopic gels suspended in 0.2 mL of phosphate buffered saline (PBS) were injected via 16-gauge diameter needles with a complete geometric restoration as illustrated in the microscopy image before and after injection.

A major drawback in today's surgical implantation of three dimensional scaffolds is the trauma created by physicians while administering the scaffolds/devices. The compositions and methods described herein reduce the cost and invasiveness of the tissue engineering approach. Prior to the invention described herein, tissue engineering used devices and polymer scaffolds that required surgical implantation. Implantation of polymer scaffolds at a surgical site requires anesthesia and incisions, each of which treatment methods have undesirable side effects. Described herein are compositions and methods that allow tissue engineers and surgeons to engage in tissue engineering applications in a less invasive manner, thereby removing the need for surgical implantation. As described in detail below, injectable scaffolds were developed to reduce the invasiveness of a tissue engineering system, thereby eliminating the need for, or reduce the size of, any incisions required to implant the material. For a system to be injectable, it must be capable of flowing through a hollow small-bore needle. Methods of implantation of a preformed scaffold or injection of a liquid for polymerization in situ presented a number of challenges including short response time, proper gelation conditions, appropriate mechanical strength and persistence time, biocompatibility, and the likelihood to protect protein drugs or cells in some adverse environments. In order to overcome these limitations, deformable fully-crosslinked and pre-shaped porous scaffold that is easily prepared, processed, and injected through the needle of a syringe was developed.

Earlier injectable hydrogels (e.g., U.S. Pat. No. 6,129, 761) allowed for the formation of scaffolds in situ but had several major drawbacks. First, potential problems occur with in situ polymerization including heat generation and un-reacted toxic chemicals. Additionally, slow gelation kinetics and in vivo biofluid dynamics involve dispersion of pre-gel solution leading to poor cell entrapment and physical integrity of the gel. Finally, nanosized pore architecture of scaffolds impedes efficient oxygen delivery, nutrient exchange, cell-movement, and long-term survivability of tissue cells.

The invention described herein provides a minimally-invasive method of injecting preformed macroporous hydrogels that are loaded with cells and/or therapeutics. Cells are implanted and cultured onto the polymeric matrix before or after administration to a subject. FDA-approved polymer-based scaffolds that support the attachment and proliferation of cells, degradable and capable of releasing drugs (e.g., proteins) at a controlled rate in vivo are designed in any desirable size and shape, and injected in situ as a safe, preformed, fully characterized, and sterile controlled delivery device. Described in detail below are biologically active cell-seeded injectable scaffolds with structural integrity within the body that controllably deliver growth factors while providing cellular building blocks to enhance tissue formation. Seeding and organizing cells prior administration of macroscopic injectable matrices enhance in vivo cell engraftment and provide cell support and guidance in the initial tissue formation stage. This invention is useful for clinical applications including artificial extracellular matrix for tissue engineering, dermal filler in cosmetic surgery, controlled release reservoir for drug and cell delivery, and immune cell reprogramming for cancer vaccines. Additional benefits include less injection pain, less bleeding/bruising and higher levels of patient satisfaction.

The present invention describes a non invasive strategy to administer large-size macroporous biodegradable hydrogels as a 3-D scaffold and a drug delivery platform. Any biocompatible polymers or monomers undergoing cryopolymerization are utilized. Suitable polymers and monomers include naturally derived polymers (alginate, hyaluronic acid, heparin, gelatin, carob gum, collagen, etc.) and synthetic polymers (poly(ethylene glycol) (PEG), PEGylated glutaminase (PEG-PGA), PEG-poly(L-lactide; PLA), poly (2-hydroxyethyl methacrylate) (pHEMA), PAAm, poly(N-isopropylacrylamide) (PNIPAAm), etc.). This ability to use different materials is useful in different applications and adds a further degree of versatility to the compositions and methods described herein. The highly elastic macroscopic scaffolds with spongy-like morphology are prepared by cryogelation, a technique used to produce polymeric materials with large interconnected pores, high volume fraction porosity within soft, mechanically stable and high water absorbing capacity. As described below, the cryogels allow for the injectability of preformed large-size scaffolds through a needle without the need of an invasive implantation. Flowable material can fill any defect due to the sponginess of the network. Elastic deformation of cryogels by external forces (mechanical deformation) led to abrupt gel shrinkage with full shape recovery capability, which is useful in the design of injectable preformed scaffolds for cell delivery in a minimally-invasive fashion for tissue engineering and regenerative medicine.

The use of large-size preformed scaffolds (>1 mm) mimicking the extracellular matrix was evaluated. Described herein is the design of large biomaterials with various shapes and sizes ranging from 2 mm up to 8 mm that are employed as injectable cell-laden scaffold cryogels. Injectable macroscopic hydrogels are supplied in individual treatment syringes for single patient use and ready for injection (implantation). The gel, consisting of crosslinked alginate suspended in a physiologic buffer, is a sterile, biodegradable, non-pyrogenic, elastic, clear, colorless, homogenized scaffold implant. The injectable gels are packaged in proprietary luer-lock syringes that are injected via a 16-gauge or smaller diameter needle depending on the size of the gel.

The strategies described herein are for delivery of preformed biomaterials suitable for minimally invasive therapies. Injectable macroscopic biomaterials are useful as surgical tissue adhesives, space-filling injectable materials for hard and soft tissue repair, drug delivery, and tissue engineering. Described herein is an approach of pure alginate scaffolds fabrication, which resulted in the formation of, interconnected, superporous network (pore size in the range of 10 μm-600 μm). These spongy-like gels are highly flexible and squeezable, capable of releasing up to 70% of their water content without altering the gel microstructure. Optionally, the gel further includes a large range of purified polymers such as hyaluronic acid, heparin, carob gum, gelatin etc; or a cell adhesive molecule such as fibronectin, or integrin binding peptide. In addition, the hydrogel is used as a drug reservoir for the controlled delivery of one or more therapeutic agents. Alginate-based gels have excellent mechanical properties, elongation, and fast shape recovery by elasticity. The shape of the gels, which was deformed by an external force (e.g., shear stress), was recovered by swelling in a very short time (<1 s). This recovery had good persistence and repeatability. The superporous (e.g., greater than 75% porosity) scaffolds described herein offer significant advantages such as injectability and easy and efficient cell encapsulation post-polymerization. For example, the cryogels are characterized by porosities of 80-90% or more. Animal studies were performed to examine the integration of the spongy-like gels with the host tissue show that the alginate-based scaffolds are biocompatible and do not elicit an immune response or rejection when injected in mice.

Synthesis of Methacrylated-Alginate (MA-Alginate) and Other Modified Polymers

Figure 10:
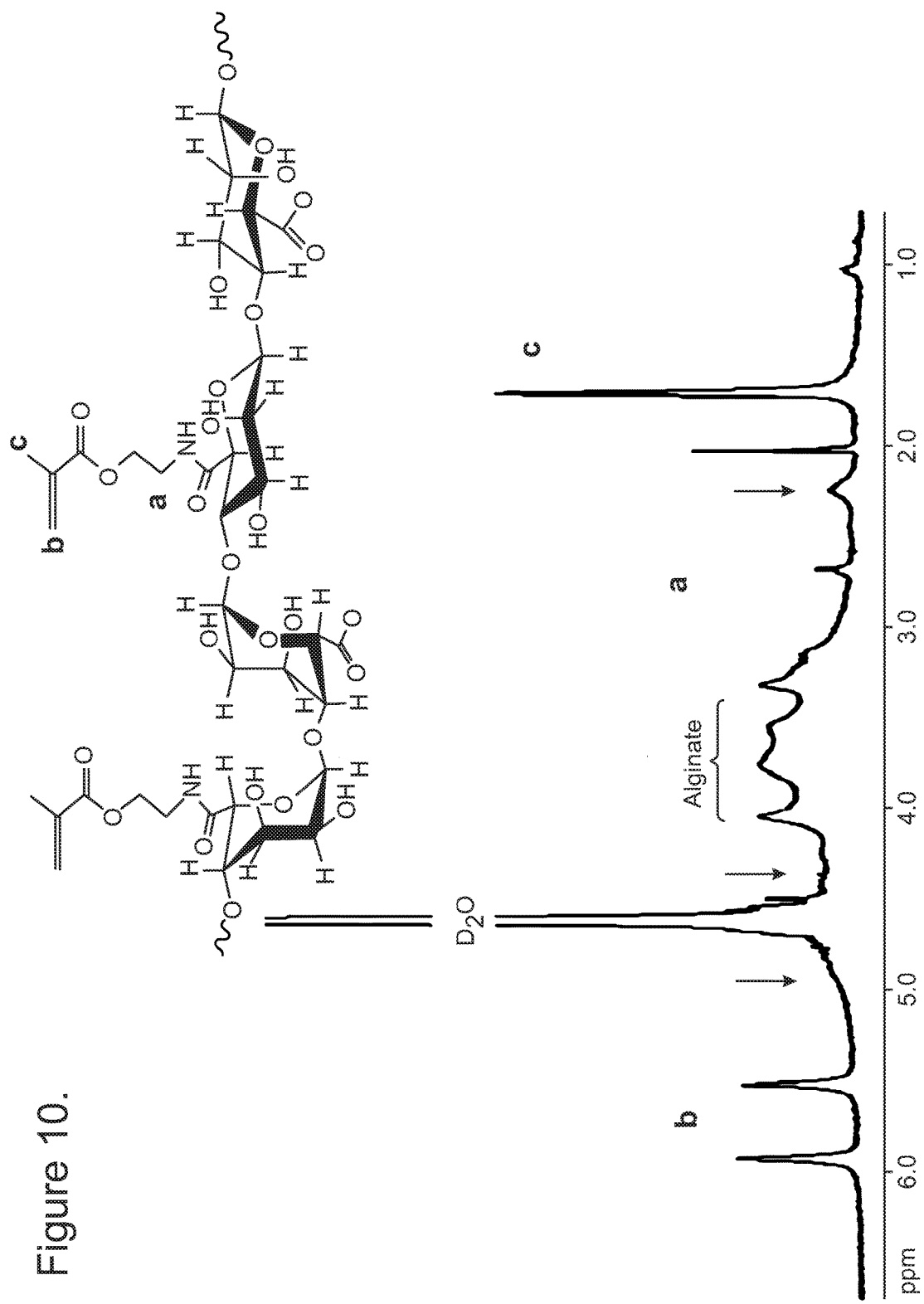
FIG. 10 is a line graph showing $^1$H NMR for MA-alginate with its characteristic vinylic peaks (~5.3-5.8 ppm). Deuterated chloroform ($D_2O$) was used as solvent, and the polymer concentration was 1% wt/v. The efficiency of alginate methacrylation was calculated based on the ratio of the integrals for alginate protons to the methylene protons of methacrylate. MA-alginate macromonomer was found to have approximately a degree of methacrylation (DM) of 49%.

Methacrylated alginate (MA-alginate) was prepared by reacting high molecular weight alginate with aminoethyl methacrylate (AEMA). To synthesize methacrylated alginate with 100% theoretical methacrylation of uronic acid carboxylate groups, high molecular weight sodium alginate (1 g) was dissolved in a buffer solution (0.6% w/v, pH~6.5) of 100 mM MES containing 0.5 M NaCl. N-Hydroxysuccinimide (NHS, 1.3 g) and N-(3-Dimethylaminopropyl)-N'-ethylcarbodiimide hydrochloride (EDC, 2.8 g) was added to the reaction mixture to activate the carboxylic acid groups of the alginate. After 5 min, AEMA (2.24 g, molar ratio of NHS:EDC:AEMA=1:1.3:1.1) was added to the product and the reaction was maintained at room temperature for 24 h. The mixture was precipitated with the addition of excess of acetone, filtered, and dried in a vacuum oven overnight at room temperature. $^1$H NMR was used to confirm the chemical modification of alginate and characterize the degree of functionalization of MA-alginate (FIG. 10).

Any biocompatible water-soluble polymer or monomer can be used to make injectable cryogels. Several monomers/polymers or a combination of polymers have been used to make the injectable cryogel devices described herein, e.g., hyaluronic acid, gelatin, heparin, dextran, carob gum, PEG, PEG derivatives including PEG-co-PGA and PEG-peptide conjugates. For example, the polymers may be a combination of degradable and nondegradable synthetic polymers and natural polymers (polysaccharides, peptides, proteins, DNA). Biocompatible synthetic polymers include Polyethylene glycol (PEG), Polyvinyl alcohol (PVA), Poly(2-hydroxyethyl methacrylate) (PHEMA), Poly(N-isopropylacrylamide) (PNIPAAm), Poly(acrylic acid) (PAAc), Polyesters (e.g. Polylactide, Polyglycolide, Polycaprolactone), and Polyanhydrides. Naturally-occurring polymers include Carbohydrates (e.g. Starch, Cellulose, Dextrose, Alginate, Hyaluronic Acid, Heparin, Dextran, Gellan Gum, etc), Proteins (e.g. Gelatin, Albumin, Collagen), Peptides, and DNA. All compositions are purified prior to fabrication of the hydrogels.

In addition to the free radical polymerization process to cross-link the polymers and make chemically cross-linked injectable cryogels (polymerization time is about 17 hr), gels are optionally polymerized using other processes. Injectable cryogels can be classified under two main groups according to the nature if their cross-linking mechanism, namely chemically and physically cross-linked gels. Covalent cross-linking processes include radical polymerization (vinyl-vinyl coupling), michael-type addition reaction (vinyl-thiol cross-linking), Condensation (carboxylic acid-alcholol and carboxylic acid-amine cross-linking), Oxidation (thiol-thiol cross-linking), Click chemistry (1,3-dipolar cycloaddition of organic azides and alkynes), Diels-Alder reaction (cycloaddition of dienes and dienophiles), Oxime, Imine and Hydrazone chemistries. Non-covalent cross-linking include Ionic cross-linking (e.g. calcium-crosslinked alginate), Self assembly (phase transition in response to external stimuli, such as Temperature, pH, ion concentration, hydrophobic interactions, light, metabolite, and electric current).

Cryogel Fabrication

Figure 2:
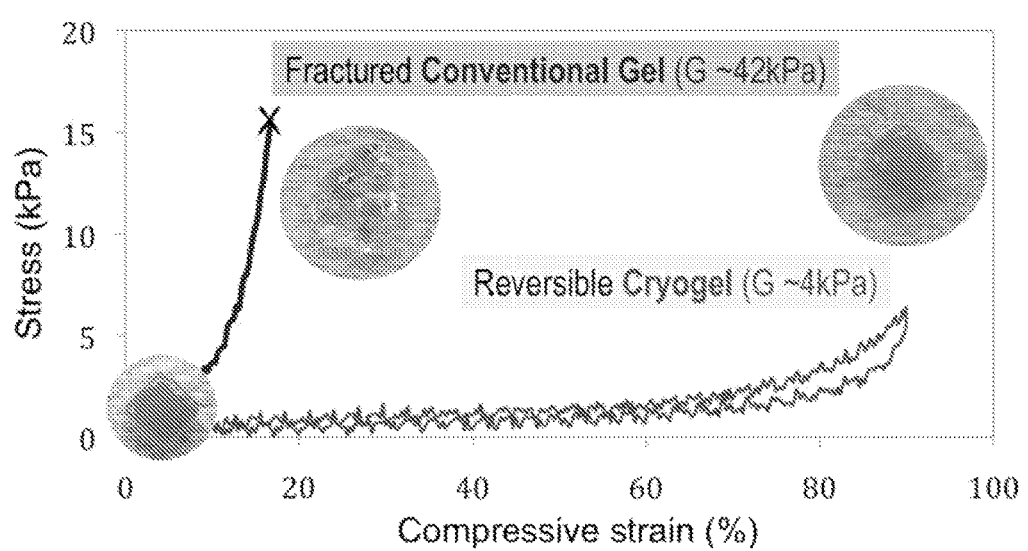
FIG. 2 is a line graph demonstrating stress vs. strain curves for conventional nanoporous and macroporous 1% rhodamine-labeled MA-alginate gels subjected to compression tests. In contrast to the brittle nature of the conventional nanoporous gels, alginate cryogels have the ability to withstand reversibly large deformation while keeping their structural integrity and shape memory properties.
Figure 11:
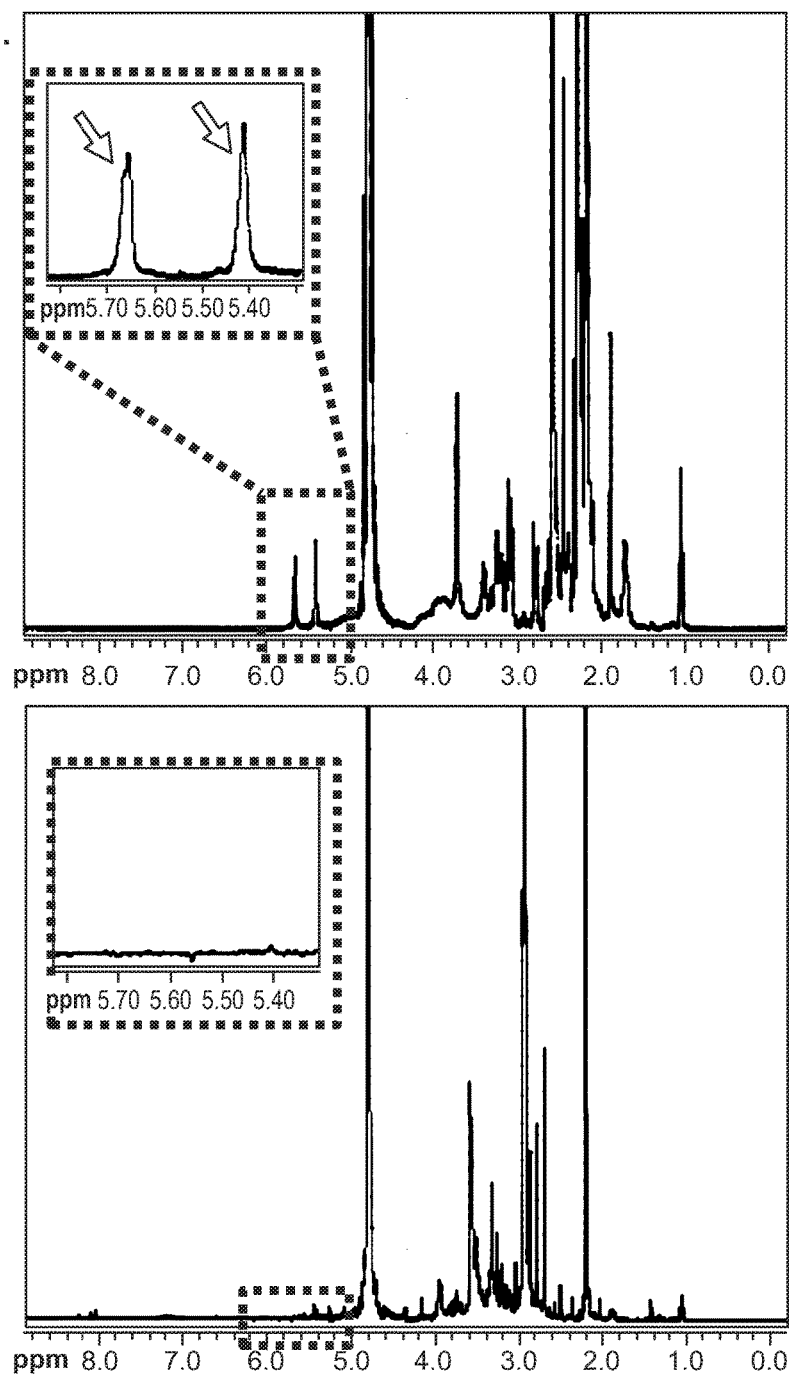
FIG. 11 is a series of line graphs showing $^1$H NMR of uncross-linked (left) and cryopolymerized (right) 1% wt/v MA-alginate in $D_2O$. Cryogelation is induced directly in an NMR tube. 1 mL of macromonomer solution containing the initiator system was transferred into the NMR tube before cryogenic treatment at −20° C. for 17 hr. The vinylic peaks (between 5.3-5.8 ppm) disappeared after cryo-crosslinking. The conversion was evaluated by comparing the relative peaks of uncross-linked and cross-linked methylene protons.

Cryogel matrices were synthesised by redox-induced free radical polymerization of MA-alginate in water. Alginate cryogels are synthesized by mixing 10 mg (1% wt/v) of MA-alginate macromonomer in deionized water with TEMED (0.5% wt/v) and APS (0.25% wt/v). The mixture is immediately poured into a pre-cooled Teflon mold and frozen at −20° C. After cryo-crosslinking has finished, gels are heated to room temperature to remove ice crystals, and washed with distilled water. Cell-adhesive cryogels were synthesized using a RGD-containing peptide composition, e.g., ACRL-PEG-G4RGDASSKY (SEQ ID NO: 2) as a comonomer (0.8% wt/v) during the polymerization. (Acryloyl is abbreviated ACRL.) By mixing the RGD-containing peptide composition (monomers) with the alginate, the RGD becomes chemically attached (covalently attached) to the polymer structure. RGD integrin-binding motif was used to promote cell-substrate interactions. NMR spectroscopy was used to characterize vinyl conversion of MA-alginate macromonomer after cryopolymerization. As shown in FIG. 2, full disappearance of methylene protons (between 5.3-5.8 ppm) for MA-alginate macromonomer (1% wt/v) was reached after the cryopolymerization process in the presence of the initiator system (APS/TEMED). This indicates that high vinyl conversions can be achieved for cryogels (see FIG. 11). Injectable cryogels can be prepared at different concentrations depending on the MW and the degree of chemical modification of the polymer itself (1% wt/v was chosen as a proof of concept).

As described above, RGD remains attached to the polymer structure by virtue of covalent bonding (co-polymerization). However, certain biomolecules are to be released following administration of the cryogel to the subject. In this case, the biomolecules are simply mixed with the polymer prior to the cryogelation process.

Cryogelation

Cryogels are a class of materials with a highly porous interconnected structure that are produced using a cryotropic gelation (or cryogelation) technique. Cryogelation is a technique in which the polymerization-crosslinking reactions are conducted in quasi-frozen reaction solution. During freezing of the macromoner (MA-alginate) solution, the macromonomers and initiator system (APS/TEMED) expelled from the ice concentrate within the channels between the ice crystals, so that the reactions only take place in these unfrozen liquid channels. After polymerization and, after melting of ice, a porous material is produced whose microstructure is a negative replica of the ice formed. Ice crystals act as porogens. Pore size is tuned by altering the temperature of the cryogelation process. For example, the cryogelation process is typically carried out by quickly freezing the solution at −20° C. Lowering the temperature to, e.g., −80° C., would result in more ice crystals and lead to smaller pores.

The advantage of these so-called "cryogels" compared to conventional macroporous hydrogels obtained by phase separation is their high mechanical stability. They are very tough, and can withstand high levels of deformations, such as elongation and torsion; they can also be squeezed under mechanical force to drain out their solvent content. The improved mechanical properties of alginate cryogels originate from the high crosslinking density (highly methacrylated alginate polymerizes into cross-linked polymer structures with a relatively high crosslink density) of the unfrozen liquid channels of the reaction system. Thus, after polymerization, the gel channels with high polymer content are perfect materials for building the pore walls.

Biomolecules, e.g., GM-CSF, CpG nucleic acids, are entrapped in the polymer structure but not chemically linked to it. Thus, these molecules are released from the cryogel by diffusion or gel degradation over time. For example, low molecular weight compositions (less than 10 kDa molecular mass), e.g., CpG oligonucleotides, are released by diffusion. Larger entrapped molecules (greater than about 10 kDa, e.g., 10-50 kDa in molecular mass), e.g., proteins, large DNAs, e.g., plasmid DNA, are released primarily by cryogel degradation. Human Recombinant GM-CSF (e.g., available from PeproTech, Catalog #300-03) is encoded by the following polypeptide sequence (SEQ ID NO:1):

```
MAPARSPSPS TQPWEHVNAI QEARRLLNLS RDTAAEMNET VEVISEMFDL QEPTCLQTRL

ELYKQGLRGS LTKLKGPLTM MASHYKQHCP PTPETSCATQ IITFESFKEN LKDFLLVIPF

DCWEPVQE
```

Injectable Hybrid Cryogels

Injectable delivery systems for therapeutic proteins (e.g., hydrogels and microspheres) have attracted wide attention. Conventional hydrogels, however, typically release their hydrophilic contents too rapidly in a large initial burst, and phagocytes may clear microspheres within a relatively short time period after administration.

Figure 12:
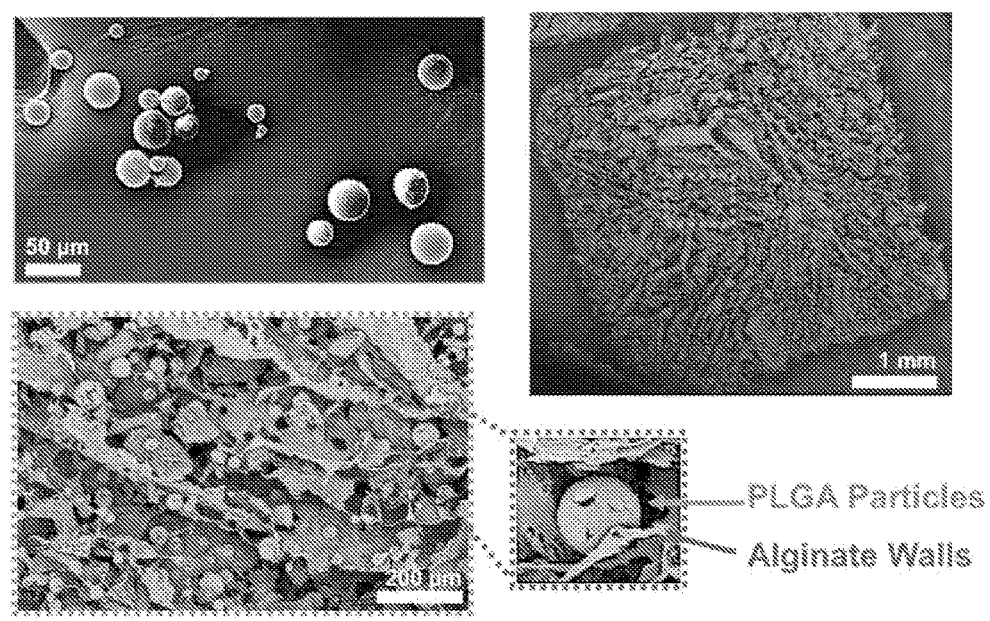
FIG. 12 is a series of photographs showing scanning electron microscopic images of free PLGA microspheres (top left) and PLGA microspheres dispersed in a alginate square-shaped cryogel (top right and bottom).

Microsphere/cryogel combination systems achieve a controlled and sustained release of proteins as an injectable delivery system. PLGA microspheres (size~10-50 μm) containing a model protein (GM-CSF) were prepared and then mixed with a MA-alginate pre-gel solution prior cryopolymerization. The mixing ratio of the components was optimized to retain injectability and shape memory properties of pure alginate cryogels. As shown in FIG. 12, PLGA microspheres were physically entrapped within the cryogel network (polymeric walls) of cryogels. Also, hybrid cryogel have been created as a carrier for controlled delivery of hydrophobic and/or low molecule weight drugs. The results not only provide a strategy for delivery drugs from an injectable 3-D preformed macroporous scaffolds as a sustained-release drug carrier but also open an avenue for the design of the hybrid injectable hydrogels.

Other examples of hybrid polymer combinations include cryo-ferrogels and polydiacetylene-based cryogels. One class of injectable porous biomaterials for on-demand drug and cell delivery comprises cryo-ferrogels. The magnetic-sensitive scaffolds based on macroporous elastic alginate-based cryo-ferrogels, were fabricated with 3-D connected macropores and coupled with magnetic particles ($Fe_3O_4$ nano- and micro-particles) and cell-binding moieties. Under applied magnetic fields, the loaded macroporous ferrogel with biological agents lead to large and prompt deformation triggering release of drugs and cells in a controlled fashion. In another example, injectable color-changing biomaterials such as polydiacetylene-based cryogels, which change in response to external stimuli such as mechanical forces. The materials contain mechanophore-molecules (e.g., Polydiacetylene Liposome) that undergo a geometric distortion when a certain amount of force is exerted upon it, leading to a color transition. Smart polymers that change color when the material becomes overstressed are very useful to identify cell-substrate interactions and to accurately measure deformations.

Administration of Injectable Cryogels

Syringes and needles are typically used to introducing the cryogels into the body. The term "syringe" technically refers to the reservoir (that holds the liquid) and the plunger (which pushes the liquid out of the reservoir). The "needle" is the part that enters the body, e.g., into a vein, under the skin, or into muscle or other tissue. The word "syringe" is also sometimes used to refer to the entire reservoir/plunger/needle combination. They come in a variety of sizes, e.g., a common reservoir size is 1 cc (1 cubic centimeter (cc)=1 milliliter), with a 25 gauge needle size or smaller.

The needle gauge refers to the size of the bore or hole in the needle. The higher the gauge, the thinner the needle (and the smaller the hole). A 28 gauge needle (abbreviated 28G) is therefore thinner than a 25 gauge needle, which is in turn thinner than an 18 gauge needle. Insulin needles are typically ½ inch in length and tuberculin needles are typically ⅝ of an inch in length. As inscribed on packaging, needle length appears after the gauge number: "28G ½" refers to a 28 gauge needle that is ½ inch long.

Larger gauge (frequently 23G or 21G), longer needles are often used for intramuscular injections. Muscle syringes are typically 1 cc in volumes, but larger volumes are sometimes, e.g., 2 to 5 ccs syringes, depending on the application. Larger volumes and larger bores are appropriate for delivery of cryogels for larger scale muscle repair or regeneration, e.g., after extensive or traumatic laceration of tissue such as injuries incurred in battle or car/plane accidents. Intravenous injectors or needles are used for fine or delicate tissue therapy, e.g., cosmetic dermal filler administration. Such applications typically use shorter needles no larger than 25G.

Survivability of Cells after Injection

Reversible compactible behavior enables pre-formed cryogels with desired physical properties, as characterized ex-vivo, to be delivered in-vivo via application of a moderate non-destructive shear stress during injection through a syringe. Studies were carried out to evaluate whether the fluid velocity, dynamic pressure, and shear stress resulting from the injection affects cell viability.

Figure 13:
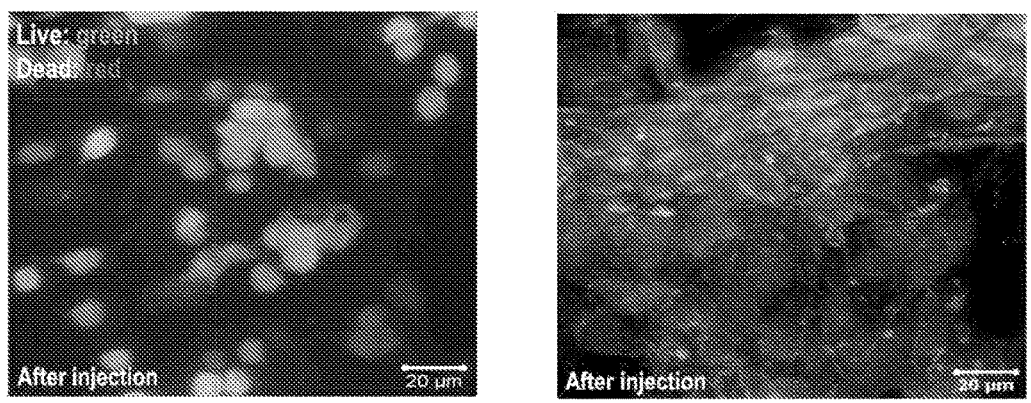
FIG. 13 is a series of photographs showing that cells injected via the cryogels have a low apoptosis and cell death. In this example, a RGD-containing peptide was chemically attached to the cryogels to improve cell adhesion to the 3D-structure alginate-based scaffolds. Cell viability, spreading, and actin cytoskeleton organization process was assessed by confocal microscopy. Cells colonize the porous structure of the alginate-based cryogel and were observed to be growing inside the pores. (Left) live/dead cell viability assay of D1 mesenchymal stem cells (MSC, 1 d incubation post-injection) and (right) confocal image showing injected D1 MSC (6 d incubation post-injection) in RGD-modified MA-alginate cryogels.

The data indicated that, during the injection, cells integrated in the RGD-modified cryogel were protected by the scaffold from mechanical damage. Although adherent cells may experience some shear stress applied during the injection, cryogels are capable of absorbing most of the energy when the scaffolds are compressed, thereby, maintaining high cell viability (92%) and their proliferative potential as shown in FIG. 13.

Thus, the shear stress (or compression) applied to cells in the cryogel as they pass through the bore of a needle or other delivery apparatus such as a catheter does not measurably hurt or damage the cells within the cryogel. Following passage through a needle or other delivery apparatus, cell viability was routinely 90% or greater.

Example 1: Injectable Biodegradable Preformed Macroscopic Geometric Gels

The compositions and methods described herein provide hydrogels for minimally invasive delivery of shape memory scaffolds for in vivo applications. This method has demonstrated highly efficient and reproducible fabrication of injectable shape-defined macroporous scaffolds. Although only one type of covalently alginate-based crosslinked gel system was evaluated herein, the material performance is readily manipulated by altering its composition, formulation, and degradation profile. The formation of specific shapes and structural stability are desirable characteristics for shape-defined materials, and the most important requirement of these types of materials for minimally invasive therapies is the ability to collapse and faithfully reform the scaffold's structure in a stimulus-responsive manner. A combination of mechanical compression and dehydration is sufficient to compress the scaffolds developed in this work, allowing minimally invasive delivery through a conventional-gauge needle.

These results described herein demonstrated that shape-defined macroporous alginate-based scaffolds were prepared with different geometric sizes and shapes, and successfully passed through a surgical needle without mechanical fracture, and all scaffolds regained their three-dimensional shape immediately (<1 s) after rehydration (FIG. 1). The fabrication method is capable to manufacture biocompatible, biodegradable and complicated macroporous tissue scaffolds efficiently and economically. In addition to the application described herein, shape memory scaffolds are especially useful in applications in which large, structurally defined implants are required.

Example 2: Structural Integrity of Injectable Macroscopic Shape-Defined Gels

The deformation of conventional (nanoporous) and macroporous 1% MA-alginate gels under mechanical compression associated with shear forces was examined. Subject to mechanical compression, the gels experience a body of force, which results in a shape change. The influence of the macropores on the gel mechanical properties was also evaluated since the stiffness of the scaffold dictate the extent of the deformation under an applied shear force. Conventional gels give a Young's modulus (i.e., the slope of the initial part of the stress vs. strain curves in FIG. 2) of 42±4 kPa in compression test. However, macroporous gels led to a dramatic reduction in the modulus to 4±2 kPa. As shown in FIG. 2, cylindrical (4 mm diameter×8 mm height) nanoporous gels reduced their heights by ~16% when subjected to a vertical load before mechanical fracture. In comparison, cylindrical macroporous gels give much larger deformation under lower mechanical stress, due to its lower modulus. Macroporous scaffolds attained 90% or more of compression strain without mechanical fracture, demonstrating their ability to maintain their structural integrity after compression, compaction, and minimally invasive delivery. Also, these results confirmed that the scaffolds displayed shape memory in vitro.

In the hydrogels described herein, the large volume change of the macroporous shape-defined gels was caused by reversible collapse of the interconnected pores. The collapsing pores force water contained in the macropores to flow out of the gel. Gel deformation and water convection enhances water transport in and out of the gel. Once the mechanical load is removed, the elastically deformed gel immediately returns to its original, undeformed shape-defined configuration in less than 1 s, as surrounding water was reabsorbed into the gel.

Example 3: Shape Memory Injectable Scaffolds as a Controlled Drug Delivery Carrier Covalently crosslinked alginate scaffolds possessing shape memory properties were successfully used as a drug delivery system in vivo. The gels having a predefined size and structure were able to exceptionally maintain their structural features after minimally invasive subcutaneously insertion in mice. Suspended gels in PBS were spontaneously hydrated with full geometric restoration after one single injection per site on the lower back of mice. Injected animals did not demonstrate abnormalities in feeding, grooming, or behavior during the time frame of the experiment, nor did they exhibit signs of distress.

Figure 3:
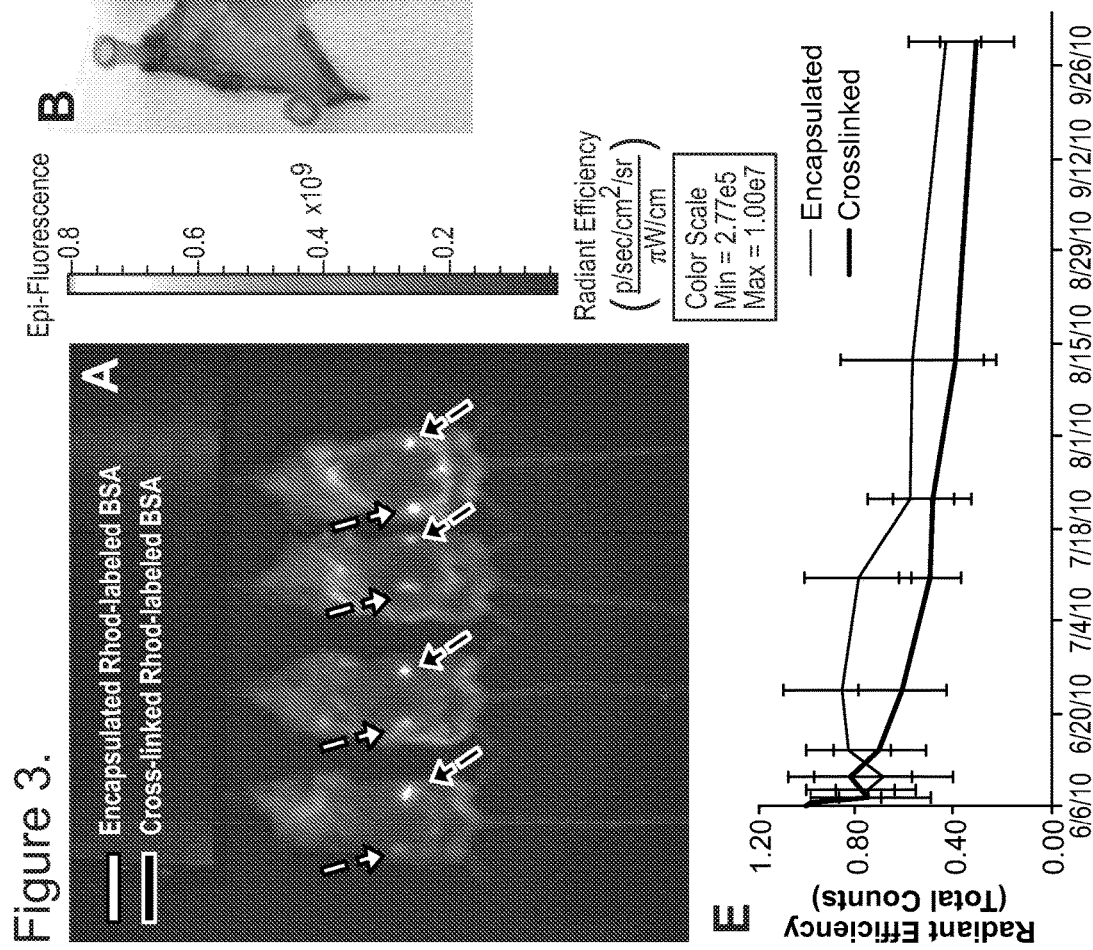
FIG. 3A is a fluorescence photograph showing minimally invasive subcutaneous injection of macroporous scaffolds into the lower back of mice.
FIG. 3B is a photograph showing hydrogel localization after subcutaneous injection of preformed rhodamine-labeled 1% MA-alginate gels (4 mm×4 mm×1 mm) in the subcutis of a mouse after 3 days.
FIG. 3C is a photograph showing merged phase-contrast and fluorescence of a subcutaneously injected rhodamine-labeled alginate macroporous scaffold with restoration of geometry after placement.
FIG. 3D is a photograph of a subcutaneously injected rhodamine-labeled alginate macroporous scaffold with restoration of geometry. Dashed lines denote square-shaped geometry restoration of inserted shape-defined scaffolds.
FIG. 3E is a line graph showing in vivo sustained release profiles of crosslinked (chemically anchored) or encapsulated (physically entrapped) rhodamine-labeled bovine serum albumin (BSA) to injected cryogels. Upon dissection 3 days post-injection, rhodamine-labeled gels recovered their square shape features, had soft consistencies, and were integrated into the surrounding tissues. Values represent mean and standard deviation (n=4).

The hydrogels maintained their hydrogel shape integrity at the site of injection. Animal studies performed to examine the integration of the spongy-like gels with the host tissue showed that the alginate-based scaffolds were biocompatible and did not elicit an immune response or rejection when injected in mice. After 3 days post-injection, rhodamine-labeled scaffolds were surgically removed from mice and analyzed. As shown in FIG. 3B, the scaffold guided in vivo tissue formation around the scaffold indicating the scaffolds could support tissue growth and integration. Furthermore, fluorescent microscopy used to visualize the rhodamine-labeled scaffold, noticeably displayed the original geometry, structural integrity, square-defined shape retention of the gels in vivo (FIG. 3C).

Rhodamine-labeled BSA was also used as a drug delivery model. By providing a drug depot at the site of injection, such devices achieve high local drug concentrations without significant systemic administration. Sustained release of BSA was achieved from the injected square-defined scaffolds as shown in FIG. 3D. Targeted and controlled delivery of rhodamine-labeled BSA in mice was quantified via real-time non-invasive live imaging (FIG. 3A). Exemplary compound, BSA, was either physically entrapped or chemically grafted to the scaffold during the cryopolymerization process. As illustrated in FIG. 3E, sustained controlled release of BSA was achieved over of period of 4 months. Surprisingly, the release profiles for both types of BSA were similar indicating that the release is mainly mediated by matrix degradation over protein diffusion.

Example 4: Cryogel Compositions Enhance Survivability and Limit Migration of Injected Cells In Vivo One application for the compositions and methods described herein is the non-invasive method of cell injection based on cell-scaffold integration. Cell transplantation is a therapeutic option for patients with impaired regional or global function due to cell death. However, the limited number of transplantation methods of cells is considered a major factor limiting the efficacy of cell therapies. As cell and bioactive molecule carriers, injectable preformed scaffolds offer the possibility of homogeneously distributing cells and molecular signals throughout the scaffold. Moreover, the scaffolds are injected directly into tissues or cavities, e.g., muscle, bone, skin, fat, organs, even of irregular shape and size, in a minimally invasive manner. The compositions and methods described herein offer significant advantages such as injectability and efficient cell encapsulation post-polymerization while allowing sufficient mechanical strength to withstand biomechanical loading and providing temporary support for the cells.

Figure 4:
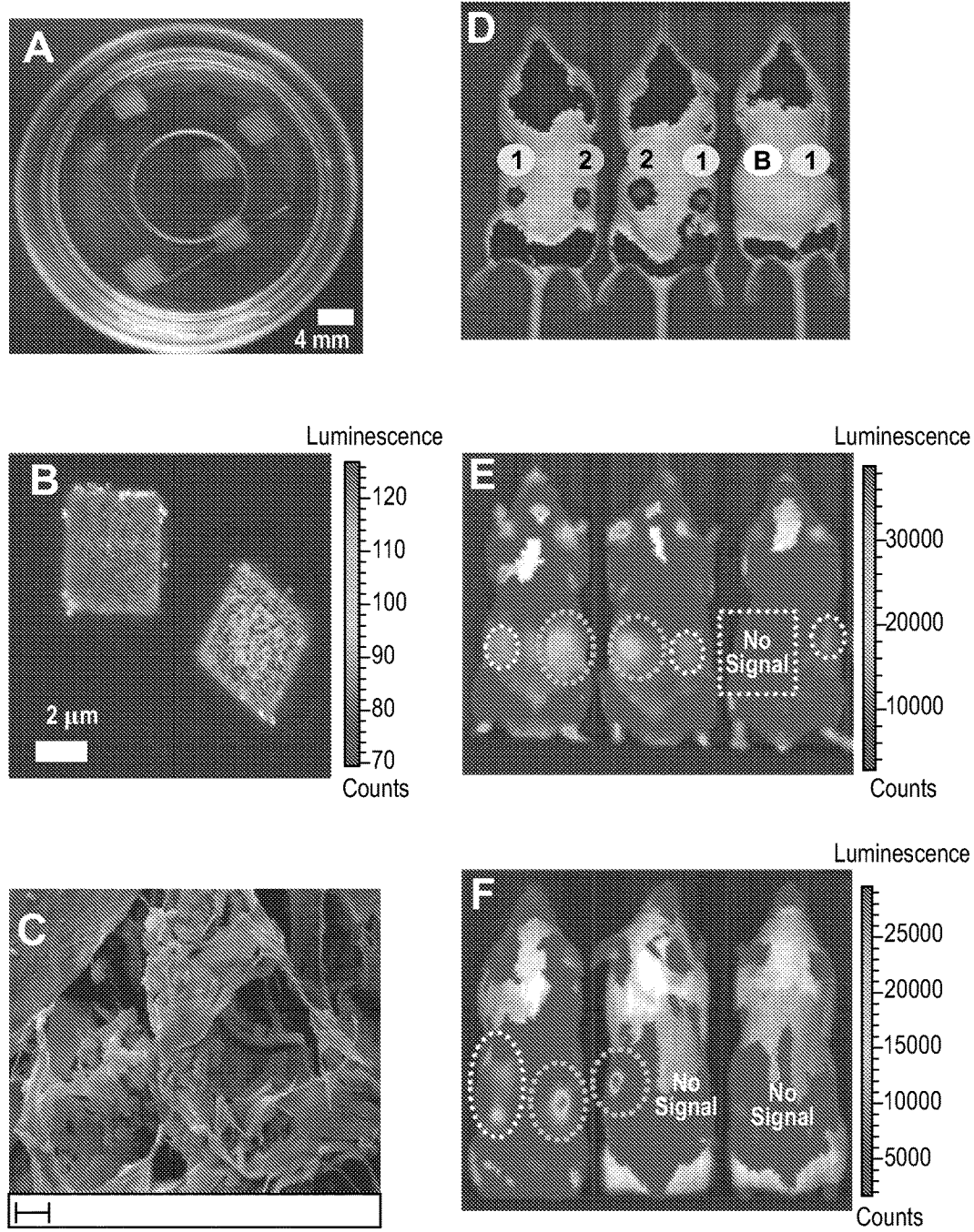
FIG. 4 is a series of photographs showing that injectable pre-seeded scaffolds promote in situ localization of bioluminescent B16 cells.

Square-shaped rhodamine-labeled RGD-containing alginate cryogels (4×4×1; units: mm) were prepared, purified, sterilized, and subsequently seeded with bioluminescent B16 cells, and maintained in culture for 6 hr in cell culture medium before animal subcutaneous injection to promote cell-scaffold integration (FIGS. 4A, 4B, and 4C). Large interconnected pores significantly enhanced cell seeding and distribution, while maintaining relatively high seeding efficiencies (>50%) and viability (>95%). To image bioluminescence of seeded B16 melanoma cells in vitro, 0.15 mg/g of luciferin was added on top of the gel, which freely diffused through the gel network, staining the cells and indicating homogeneous infiltration and depth viability of cells throughout the 3-D construct (FIG. 4B). This is due to the effective nutrient delivery into and waste removal from the inner regions of the scaffold. SEM images confirmed a homogeneous distribution and engraftment of cells within the scaffold (FIG. 4C).

A unique characteristic of these cell/scaffold constructs is that when an appropriate shear stress is applied, the deformable hydrogel is dramatically and reversibly compressed (up to 90% of its volume) resulting in injectable macroporous preformed scaffolds. This property allows gel/cell constructs to be delivered via syringe with high precision to target sites. Homogenous cellular distribution and cell viability are unaffected by the shear thinning process and gel/cell constructs stay fixed at the point of introduction, suggesting that these gels are useful for the delivery of cells to target biological sites in tissue regeneration efforts.

Subsequently, healthy C57BL/6 mice received a subcutaneous injection on their backs of $200 \times 10^3$ B16's integrated into alginate macroporous scaffolds. The resulting injected gels were delivered to a targeted site where they quickly recovered to their original mechanical rigidity with location permanency. As shown in FIG. 4D, cell-loaded rhodamine-labeled alginate scaffolds were syringe-delivered (1 cc, 16G) with high precision in the back of mice and visualized by in vivo optical live imaging. Integration of melanoma B16 cells to RGD-modified alginate cryogel scaffolds and their injections into healthy mice was investigated to demonstrate successful syringe-delivery and function of pre-cultured cells while promoting homing, survival, and engraftment of tumorigenic cells. The results presented herein demonstrate that the designed tissue-engineered scaffolds mimic the natural environment where cells normally reside, and as a result tumors are formed after every injection of tumorigenic cell-embedded matrix in healthy BALB/c mice. The inoculation of melanoma cells subcutaneously was monitored via real-time non-invasive live imaging (FIG. 4D). The incidence of tumor formation and tumor growth was examined over a period of 9 days. The success of the melanoma B16 tumor model is clearly evident as shown in FIGS. 4D-4E. As an in vivo model, the cell/scaffold construct has fulfilled several criteria: successful syringe-delivery with precision to a target site and cell survival in their current local environment resulting in tumor formation.

As described herein rhodamine-labeled (1) and rhodamine-labeled RGD-modified (2) cell-seeded alginate cryogels were administered in mice to study the effect of cell-engraftment in cell transplantation and homing. As a control, a bolus of free cells (B) was also injected. Rhodamine-labeled scaffolds were successfully injected subcutaneously as shown in FIG. 4D. Except for the bolus injection site, red-emitting rhodamine dyes show intense fluorescent red spots in each side of the mice's back indicating in vivo localization of cell-seeded scaffolds. After 2 days post-injection, bioluminescence of cell-seeded scaffolds was measured 30 min after intraperitoneal injection of luciferin. As shown in FIG. 4E, bioluminescence for injected RGD-modified cell-seeded gels was particularly brighter when compared to the plain scaffolds showing the necessity to incorporate RGD to the polymeric network to support cell-engraftment and thus efficient cell transplantation. For the injection of the cellular bolus, the absence of bioluminescence suggests minimal cell retention at the injection site, rapid cell migration, and likely limited cell transplants survival. Similarly, 9 days post-injection, bioluminescence of cell-seeded scaffolds was mainly apparent for RGD-modified scaffolds confirming the developed non-invasive method for cell injection based on cell-scaffold integration is crucial to decrease migration, promote homing, enhance survivability, and engraftment of cells in vivo (FIG. 4F).

Decreasing the rapid cell death that occurs within a few days after transplantation of graft cells is of great relevance for the success of cell transplantation therapies. The results presented herein confirm that the incorporation of the cell-adhesive peptide plays a key role in regulating interactions between cells and the scaffold and cell-fate. These gels are also suitable for use as a delivery system for the sustained delivery of proteins (e.g., growth factors) involved in cell differentiation and maturation (FIG. 3E). This technique is also a tool for enhancing stem cell survival in vivo.

Example 5: Injectable Biodegradable Cryogels for Immunotherapy Applications

A minimally invasive scaffold-based active vaccine containing host pathogens was developed for the therapeutic treatment of cancer. In the case of cancer, the immune system needs an external boost from immunotherapies to be able to become more effective in fighting cancer. The active immunotherapy system described herein was designed to stimulate the patient's immune system, with the objective of promoting an antigen-specific antitumor effect using the body's own immune cells. In addition, the cryogel-vaccine leads to a durable antitumor response that protects tumor recurrence. Dendritic cells (DCs) are antigen-presenting cells critically involved in regulating the immune system. The vaccine mediates in situ manipulation of dendritic cell recruitment, activation, and their dispersion to the lymph nodes. Cytosine-guanosine oligonucleotide (CpG-ODN) was used as an adjuvant further stimulate responses to the vaccine.

Figure 5:
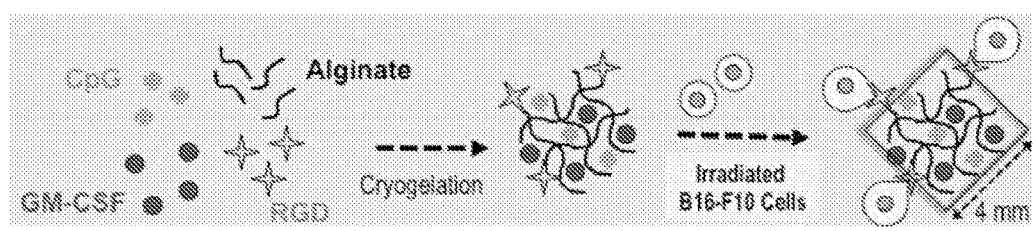
FIG. 5 is a diagram showing preparation of an autologous alginate-based active cryogel vaccine containing living attenuated B16-F10 melanoma cells for the prophylactic and therapeutic treatments of skin cancer in mice. CpG (adjuvant) & GM-CSF (cytokine) loaded RGD-modified alginate cryogels were seeded with irradiated B16-F10 cells and cultured for 6 h prior animal vaccination via subcutaneous injection.
Figure 6:
FIG. 6 is a bar graph showing immunity against B16F10 challenge induced by different vaccination protocols. Infection-mimicking microenvironment from injectable alginate-based cryogel confered potent anti-tumor immunity. A comparison of the survival time in mice treated with Cryogels; (C) antigen+GM-CSF+CpG-ODN ($0.2 \times 10^6$ irradiated B16F10 melanoma cells+3 µg GM 100 µg CpG), antigen+GM-CSF ($0.4 \times 10^6$-CSF+(D) 6 irradiated B16F10 melanoma cells+3 µg GM), (E) antigen+CpG-ODN ($0.4 \times 10^6$ irradiated B16F10 melanoma cells+100 µg CpG). Animals were also immunized using $0.4 \times 10^6$ B16F10 melanoma cells transduced with the murine GM-CSF gene (A) and bolus injections of $0.4 \times 10^6$ irradiated B16F10 melanoma cells+3 µg GM-CSF+100 µg CpG-ODN (B). Mice were challenged (Day 6) with $10^5$ B16-F10 melanoma tumor cells and monitored for the onset of tumor occurrence. Each group contained 10 mice.
Figure 7:
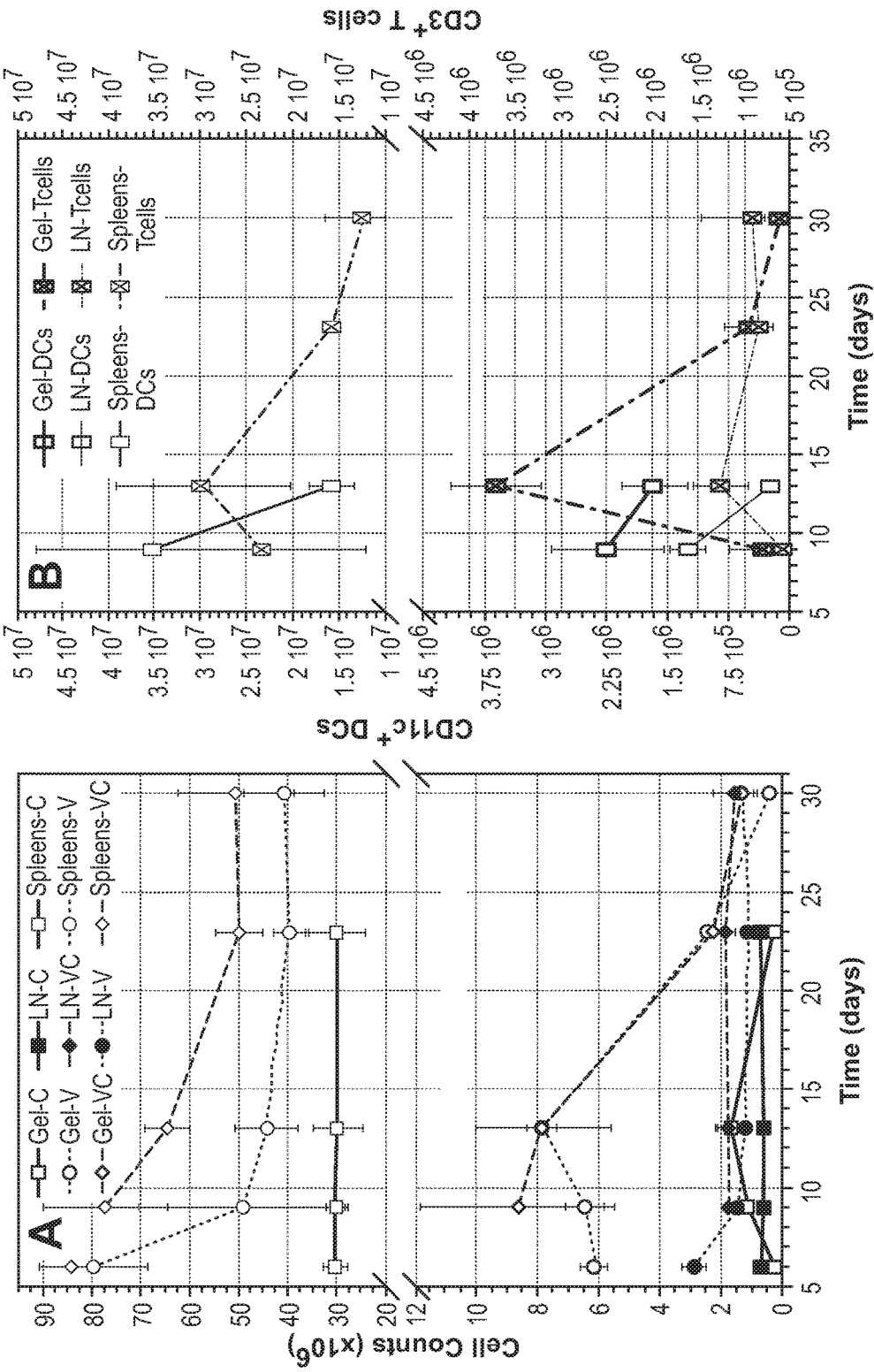
FIGS. 7A and B are line graphs showing that local delivery of cryogel vaccine promotes recruitment of CD11c (+) DCs and proliferation of CD3(+) T cells. (A) Cell recruitment and expansion at the injection site and secondary lymphoid organs (LN, spleen) in response to cryogel vaccination and challenge. The in vivo proliferative responsiveness of the cells was assessed by cell counting. (B) Cryogel matrices co-delivering GM-CSF, CpG-ODN, and presenting attenuated B16F10 melanoma cells stimulate potent local and systemic CD11$_c$(+) DCs and CD3(+) T cells in secondary lymphoid organs (LN and spleen) as well as the cryogel scaffolds. Values in (A-B) represent mean and standard deviation (n=5).

As shown in FIG. 5, both components (adjuvant and cytokine) can be easily incorporated into the cryogel matrix and released in a sustained fashion to recruit and host DCs, and subsequently present cancer antigens from the irradiated cells (or other cell-associated antigens) and danger signals to activate resident naïve DCs and promote their homing to the lymph nodes, which is necessary for a robust anti-cancer immune response. Specific and protective anti-tumor immunity was generated with our minimally invasive alginate-based active vaccine, as 80% survival was achieved in animals that otherwise die from cancer within a couple of months. The data using the cryogel-based prophylactic vaccine for melanoma was shown to induce a very strong immunologic memory, as 100% survival was achieved in the rechallenged animals following 100 days post vaccination.

Different tumor cell-associated antigens are used in the cellular cryogel-based vaccine platform, thereby permitting treatment or prophylaxis for a variety of cancers. Active specific immunotherapy involves the priming of the immune system in order to generate a T-cell response against tumor-associated antigens. One example of the active specific approach is adoptive T-cell therapy, which involves the ex vivo cultivation of T cells with demonstrated activity against a specific target cancer antigen. Cells are obtained from the subject, purified, and cultured. Such ex vivo cultivation increases the frequency of these T cells to achieve therapeutic levels. The cells are then infused back into the patient via injectable alginate-based cryogel.

Creating an infection-mimicking microenvironment by appropriately presenting exogenous cytokines (e.g., GM-CSF) and danger signals (e.g., CpG-ODN), in concert with cancer antigen provides a means to precisely control the number and timing of DC trafficking and activation, in situ. At different time points post scaffold-based vaccine injection (vax C), cells were isolated from the cryogels and surrounding tissues, spleen, and lymph nodes (LN) for cell counting and fluorescence-activated cell sorting (FACS) analysis to determine the overall number of cells and percentage of DCs (CD11c+ cells) and T cells (CD3+ cells). Cells infiltrating the vaccine site and the enlargement of spleen and LN after vaccination revealed a significant immunologic response to cancer. The increased numbers of immune system cells fighting cancer antigens made the two organs expand and become "swollen." As shown in FIG. 3A, the total numbers of cells increased dramatically for the vaccinated (V) and vaccinated/challenged (VC) mice when compared to the control groups (C) for the spleen, LN, and cryogels. The increase number of cells remained relatively high within the first 2 weeks post vaccination and started to noticeably drop by day 13 impaired with a reduction of immunologic and inflammatory responses.

Macroporous cryogel matrices were fabricated for controlled release of GM-CSF to recruit and house host DCs, and with an interconnected porous structure that allows for cell infiltration and subsequently present cancer antigens (irradiated B16F10 melanoma cells) and danger signals (CpG-ODN) to activate the resident DCs and dramatically enhance their homing to lymph nodes and proliferation. Matrices were loaded with 3 mg of GM-CSF and injected into the subcutaneous pockets of C57BL/6J mice. FIG. 3B indicates that the cryogel vaccine controls or therapeutically alters immune cell trafficking and activation in the body. Within the first 10 d post vaccination, a large number of DCs are recruited to the vaccine site. As these activated DCs may home to the inguinal lymph nodes and spleen, present antigens to naive T cells, and stimulate and expand specific T-cell populations that elicit anti-tumor responses, the total number of CD11c(+) DCs is inversely proportional to the total number of CD3(+) T cells. FACS analysis of cells infiltrating the vaccine site revealed a significant CD3(+) T cell response peaking at day 13. Local CD3(+) T cell numbers dropped sharply by day 24 and were negligible at day 30.

Figure 8:
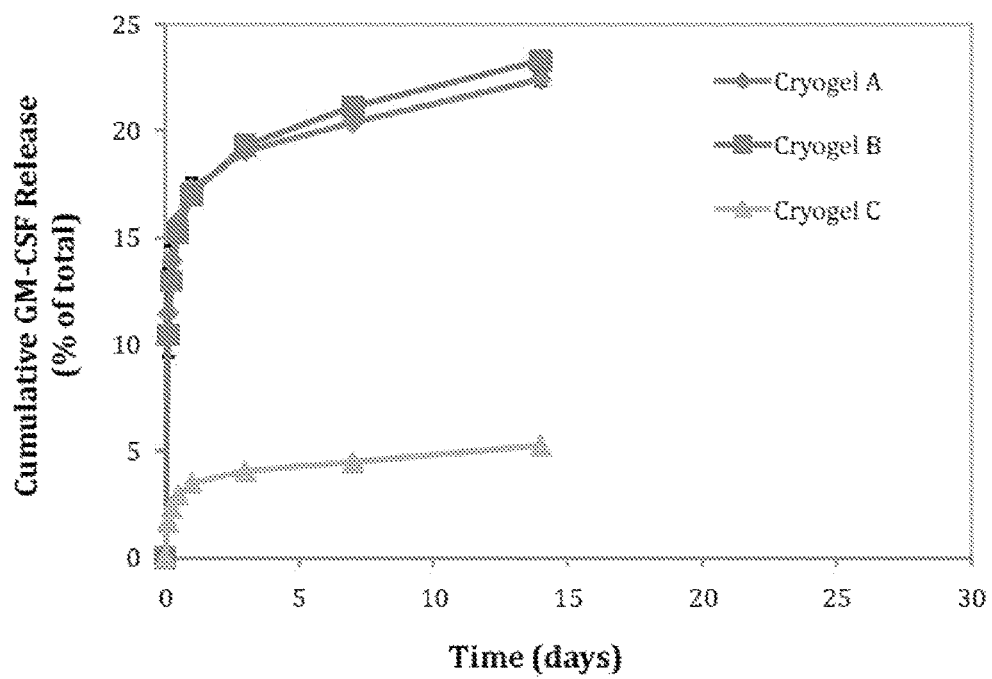
FIG. 8 is a line graph showing controlled release of GM-CSF for DC recruitment and programming. Cumulative release of GM-CSF from Alginate-based cryogel matrices over a period of 2 weeks; (A) 3 µg GM-CSF, (B) 3 µg GM-CSF+100 µg CpG-ODN, (C) PLG microsphere containing 3 µg GM-CSF. Values represent mean and standard deviation (n=5).

These cryogel matrices released approximately 20% of their bioactive GM-CSF load within the first 5 days, followed by slow and sustained release of bioactive GM-CSF over the next 10 days (FIG. 8, cryogel A); this release profile was chosen to allow diffusion of the factor through the surrounding tissue to effectively recruit resident DCs. Cryogels can be successfully used for specific spatiotemporal delivery of several drugs, as the incorporation of a second biomolecule (CpG-ODN) did not alter the release profile of GM-CSF over time (FIG. 8, cryogel B). However, slowly degrading PLG microspheres integrated in the scaffolds seem to release GM-CSF much more slowly than pure cryogels (5% vs 24% release at day 14). Hybrid cryogel have been created as a potential carrier for controlled delivery of hydrophobic and/or low molecule weight drugs. Our results not only provide a new strategy for delivery drugs from an injectable 3-D preformed macroporous scaffolds as a sustained-release drug carrier but also open an avenue for the design of new hybrid injectable hydrogels.

Example 6: Injectable Biodegradable Cryogels as a Gene Delivery System

Figure 9:
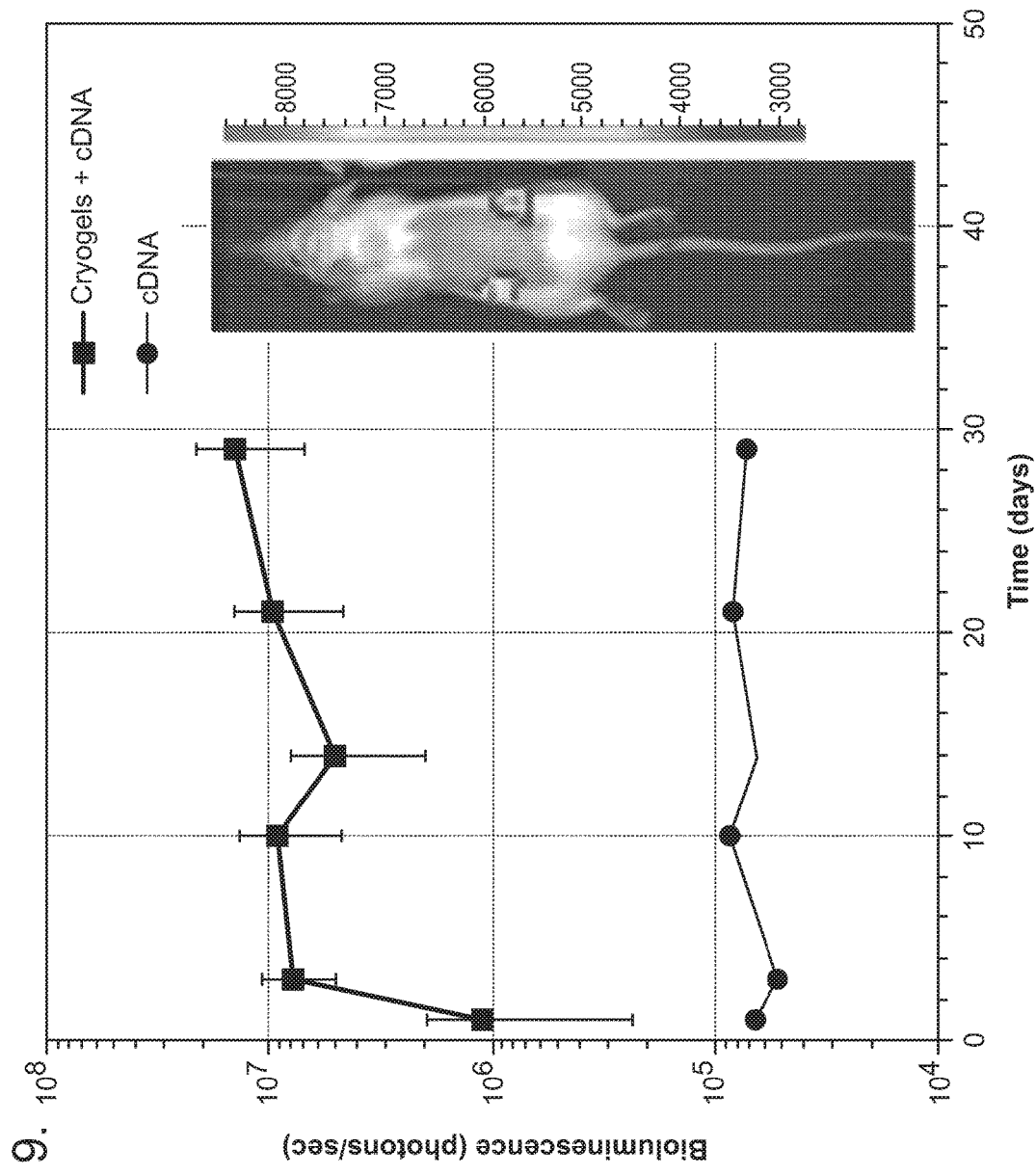
FIG. 9 is a line graph showing cryogel-enhanced plasmid DNA transfection. Relative bioluminescence over time for cells transfected with a luciferase expression plasmid (150 µg/cryogel, 2 injections/animal). Cryogels assist in efficient delivery and cell transfection of polyethylenimine (PEI)/plasmid DNA (blue) when compared to naked PEI/DNA (red). Values represent mean and standard deviation (n=5). The inset is a photograph that shows a representative localized light emission in response to application of firefly luciferin after 29 d post injection in mice inoculated with PEI/DNA-containing cryogels.

Nonviral gene delivery systems based upon polycation/plasmid DNA complexes are gaining recognition as an alternative to viral gene vectors for their potential in avoiding immunogenicity and toxicity problems inherent in viral systems. Studies were carried out to determine the feasibility of using a controlled release system based on encapsulated condensed plasmid DNA in injectable cryogels to achieve gene transfer in the surrounding tissues after injection. A unique feature of the cryogel-based gene delivery system is the biodegradability of the polymeric system, which can provide a sustained release of DNA at different rates depending on the polymer, cross-link density, mass fraction, and porosity created during the cryogelation process. Encapsulated DNA complexed with polyethylenimine (PEI), a non-degradable cationic polymer known to be an effective gene carrier, and naked PEI/DNA complexes, which were prepared at a ratio of 7:1 (PEI:DNA) were injected subcutaneously on the lower back of naïve mice using luciferase as a reporter gene (FIG. 9). At 1 day after injection, encapsulated PEI/DNA displayed strong bioluminescence providing the highest transgene expression at ~10 photons/s, about two-order of magnitude higher than that produced by naked PEI/DNA. After 10 days, the expression levels for naked PEI/DNA were about the same as day 1 but increased by 1 order of magnitude when released in a controllable fashion from the cryogels. Till 29 days, encapsulated PEI/DNA still provided a level of transgene expression at ~$10^7$ photons/s, similar to that observed at previous time points. This level was significantly higher than those offered by naked PEI/DNA.

In this study, subcutaneous gene delivery allowed gene expression on the lower back of naïve mice, although the distribution pattern and intensity was vehicle-dependent. Naked PEI/DNA complexes produced limited bioluminescence (signal nearly above background), probably because of its vulnerability to DNAses. However, encapsulated PEI/DNA complexes in cryogels used in this study provided a targeted and sustained high level of gene expression around the injection site for at least 3 weeks. These findings indicate that a 3-D macroporous scaffold may facilitate sustained release and efficient cell transfection of polymer/DNA complexes.

In summary, the present approach has demonstrated that cryogels promote gene transfection to surrounding cells in the subcutis of mice, with an efficiency superior in terms of prolonged gene expression to naked DNA. The results establish an injectable delivery system as an effective gene carrier applicable to program or treat targeted cells.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An injectable cell-compatible highly crosslinked cryogel composition comprising open interconnected pores,
   wherein said cryogel composition comprises at least 75% pores, and wherein said cryogel composition is characterized by shape memory following deformation by compression through a needle, such that said cryogel composition returns to its original undeformed three-dimensional shape less than one second after compression through the needle, and
   wherein said cryogel composition comprises a cryo-crosslinked alginate polymer, wherein said alginate is methacrylated.

2. The cryogel composition of claim 1, comprising at least 90% pores.

3. The cryogel composition of claim 1, comprising at least 90% water when water is within said pores such that said cryogel is in a fully hydrated state.

4. The cryogel composition of claim 1, comprising less than 25% water when compressed.

5. The cryogel composition of claim 1, comprising a cell adhesion composition covalently attached to said polymer.

6. The cryogel composition of claim 5, wherein said cell adhesion composition comprises a peptide comprising an RGD amino acid sequence.

7. The cryogel composition of claim 1, comprising a eukaryotic cell in one or more of said open interconnected pores.

8. The cryogel composition of claim 7, wherein said eukaryotic cell comprises a live attenuated cancer cell.

9. The cryogel composition of claim 1, comprising a biomolecule in one or more of said open interconnected pores.

10. The cryogel composition of claim 9, wherein said biomolecule comprises a small molecule, nucleic acid, or protein.

11. The cryogel composition of claim 10, wherein said protein comprises granulocyte macrophage-colony stimulating factor (GM-CSF).

12. The cryogel composition of claim 10, wherein said nucleic acid comprises a CpG nucleic acid oligonucleotide.

13. The cryogel composition of claim 1, which is injectable through a hollow needle.

14. The cryogel composition of claim 1, wherein upon compression, said cryogel composition maintains structural integrity and shape memory properties.

15. The cryogel composition of claim 1, further comprising gelatin, heparin, dextran, carob gum, PEG, a PEG derivative, collagen, chitosan, carboxymethylcellulose, pullulan, PVA, PHEMA, PNIPAAm, or PAAc.

16. The cryogel composition of claim 1, comprising the shape of a disc, cylinder, square, rectangle, or string.

17. The cryogel composition of claim 1, which is between 100 μm$^3$ to 100 mm$^3$ in size.

18. A method for delivering genetic material to a tissue, comprising administering the cryogel composition of claim 1, wherein said cryogel composition further comprises a nucleic acid.

19. The method of claim 18, wherein said nucleic acid comprises plasmid DNA.

20. A method for eliciting an immune response, comprising administering to a subject the cryogel composition of claim 8.

21. The method of claim 20, wherein said cryogel composition is administered prophylactically or therapeutically.

22. The cryogel composition of claim 1, wherein the highly crosslinked cryogel composition comprises a crosslinking density of at least 50% polymer crosslinking.

23. The cryogel composition of claim 1, wherein the highly crosslinked cryogel composition comprises a crosslinking density of at least 50-100% polymer crosslinking.

24. The cryogel composition of claim 8, wherein said live attenuated cancer cell is a live attenuated melanoma cancer cell.

25. The cryogel composition of claim 4, which returns to its original undeformed three-dimensional shape after it is compressed by up to 90% of its volume.

26. The cryogel composition of claim 1, further comprising a tumor antigen.

27. A syringe comprising (i) a needle, (ii) a reservoir that comprises the cryogel composition of claim 1, and (iii) a plunger.

28. The syringe of claim 27, comprising a 16-gauge, an 18-gauge, a 22-gauge, a 24-gauge, a 26-gauge, a 28-gauge, a 30-gauge, a 32-gauge, or a 34-gauge needle.

29. The syringe of claim 27, comprising an 18 to 30-gauge needle.

30. The syringe of claim 28, wherein the device is between 1 $mm^3$ to 50 $mm^3$ in size.

31. The syringe of claim 28, therein the cryogel composition further comprises live attenuated cancer cells, wherein 90% or more of the cancer cells survive passage of the cryogel composition through the bore of the needle.

32. The syringe of claim 27, wherein the cryogel composition is filled with a physiologically-compatible solution, wherein said cryogel composition is characterized by shape memory following deformation by compression from the reservoir through the needle, such that said cryogel composition returns to its original undeformed three-dimensional shape less than one second after compression from the reservoir through the needle.

33. The cryogel composition of claim 1, wherein said cryogel composition comprises macropores having a diameter of 10 μm to 600 μm.

34. The syringe of claim 27, wherein said cryogel composition comprises macropores having a diameter of 10 μm to 600 μm.

35. The cryogel composition of claim 9, wherein said biomolecule comprises a pathogen-associated molecular pattern (PAMP).

36. The cryogel composition of claim 1, wherein said cryogel composition is characterized by shape memory following deformation by compression from a reservoir of a syringe, in which the cryogel composition is filled with a physiologically-compatible solution, through a needle of the syringe, such that said cryogel composition returns to its original undeformed three-dimensional shape less than one second after compression from the reservoir through the needle.

37. The cryogel composition of claim 1, wherein said cryogel composition comprises a Young's modulus of 4±2 kPa.

38. The syringe of claim 27, wherein the reservoir holds a liquid.

39. The syringe of claim 38, wherein the liquid is a physiologically-compatible solution.

* * * * *

UNITED STATES PATENT AND TRADEMARK OFFICE
CERTIFICATE OF CORRECTION

PATENT NO. : 10,045,947 B2
APPLICATION NO. : 14/112096
DATED : August 14, 2018
INVENTOR(S) : Sidi A. Bencherif et al.

Page 1 of 1

It is certified that error appears in the above-identified patent and that said Letters Patent is hereby corrected as shown below:

On the Title Page

At Column 2, item (74) Attorney, Agent, or Firm, Line number 2, replace "Marin" with --Maria--.

Signed and Sealed this
Eleventh Day of June, 2019

Andrei Iancu
*Director of the United States Patent and Trademark Office*

UNITED STATES PATENT AND TRADEMARK OFFICE
CERTIFICATE OF CORRECTION

PATENT NO. : 10,045,947 B2
APPLICATION NO. : 14/112096
DATED : August 14, 2018
INVENTOR(S) : Sidi A. Bencherif et al.

It is certified that error appears in the above-identified patent and that said Letters Patent is hereby corrected as shown below:

In the Specification

At Column 1, Lines 26-29, please replace "This invention was made with U.S. Government support under Grant Number R01 DE013349 from the National Institutes of Health. The Government has certain rights in the invention." with --This invention was made with government support under DE013349 and DE019917 and EB015498 awarded by National Institutes of Health (NIH) and under 0335765 awarded by National Science Foundation (NSF). The Government has certain rights in this invention.--

Signed and Sealed this
Fourth Day of October, 2022

Katherine Kelly Vidal
*Director of the United States Patent and Trademark Office*